(12) United States Patent
Negrete et al.

(10) Patent No.: US 11,661,599 B1
(45) Date of Patent: May 30, 2023

(54) CRISPR-CAS BASED SYSTEM FOR TARGETING SINGLE-STRANDED SEQUENCES

(71) Applicants: National Technology & Engineering Solutions of Sandia, LLC, Albuquerque, NM (US); The Regents of the University of California, Oakland, CA (US)

(72) Inventors: Oscar Negrete, Livermore, CA (US); Jennifer A. Doudna, Berkeley, CA (US); Steven C. Strutt, Berkeley, CA (US)

(73) Assignees: National Technology & Engineering Solutions of Sandia, LLC, Albuquerque, NM (US); The Regents of the University of California, Oakland, CA (US)

( * ) Notice: Subject to any disclaimer, the term of this patent is extended or adjusted under 35 U.S.C. 154(b) by 824 days.

(21) Appl. No.: 16/219,779

(22) Filed: Dec. 13, 2018

Related U.S. Application Data

(60) Provisional application No. 62/598,888, filed on Dec. 14, 2017.

(51) Int. Cl.
| | | |
|---|---|---|
| *C12N 15/11* | (2006.01) | |
| *C12N 9/22* | (2006.01) | |
| *C12Q 1/6888* | (2018.01) | |
| *A61K 31/7088* | (2006.01) | |
| *A61K 38/46* | (2006.01) | |

(52) U.S. Cl.
CPC .......... *C12N 15/11* (2013.01); *A61K 31/7088* (2013.01); *A61K 38/465* (2013.01); *C12N 9/22* (2013.01); *C12Q 1/6888* (2013.01); *C12N 2310/20* (2017.05); *C12N 2800/80* (2013.01)

(58) Field of Classification Search
CPC ...... C12N 15/11; C12N 2310/20; C12N 9/22; C12N 2800/80; C12Q 1/6888
See application file for complete search history.

(56) References Cited

U.S. PATENT DOCUMENTS

| | | | |
|---|---|---|---|
| 7,494,786 B2 | 2/2009 | Doudna et al. | |
| 8,206,968 B2 | 6/2012 | Doudna et al. | |
| 8,440,430 B2 | 5/2013 | Doudna et al. | |
| 8,470,575 B2 | 6/2013 | Doudna et al. | |
| 8,828,736 B2 | 9/2014 | Perroud et al. | |
| 8,852,911 B2 | 10/2014 | Doudna et al. | |
| 8,969,062 B2 | 3/2015 | Doudna et al. | |
| 9,115,348 B2 | 8/2015 | Haurwitz et al. | |
| 9,260,752 B1 | 2/2016 | May et al. | |
| 9,410,198 B2 | 8/2016 | May et al. | |
| 9,434,930 B2 | 9/2016 | Doudna et al. | |
| 9,549,976 B1 | 1/2017 | Peabody et al. | |
| 9,605,246 B2 | 3/2017 | Haurwitz et al. | |
| 9,688,971 B2 | 6/2017 | Doudna et al. | |
| 9,708,646 B2 | 7/2017 | Haurwitz et al. | |
| 9,725,714 B2 | 8/2017 | May et al. | |
| 9,745,610 B2 | 8/2017 | Doudna et al. | |
| 9,803,194 B2 | 10/2017 | May et al. | |
| 9,809,814 B1 | 11/2017 | May et al. | |
| 9,909,122 B2 | 3/2018 | May et al. | |
| 9,963,689 B2 | 5/2018 | Doudna et al. | |
| 9,994,831 B2 * | 6/2018 | Doudna | C12Q 1/6874 |
| 10,000,772 B2 | 6/2018 | Doudna et al. | |
| 10,087,431 B2 | 10/2018 | Wiedenheft et al. | |
| 10,113,167 B2 | 10/2018 | Doudna et al. | |
| 10,125,361 B2 | 11/2018 | May et al. | |
| 2004/0072179 A1 | 4/2004 | Doudna et al. | |
| 2008/0318273 A1 | 12/2008 | Doudna et al. | |
| 2011/0117610 A1 | 5/2011 | Doudna et al. | |
| 2011/0223638 A1 | 9/2011 | Wiedenheft et al. | |
| 2012/0252096 A1 | 10/2012 | Doudna et al. | |
| 2013/0130248 A1 | 5/2013 | Haurwitz et al. | |
| 2013/0196383 A1 | 8/2013 | Doudna et al. | |
| 2013/0337503 A1 | 12/2013 | Doudna et al. | |
| 2014/0068797 A1 | 3/2014 | Doudna et al. | |
| 2014/0302563 A1 | 10/2014 | Doudna et al. | |
| 2014/0315985 A1 | 10/2014 | May et al. | |
| 2015/0152398 A1 | 6/2015 | Doudna et al. | |
| 2015/0152403 A1 | 6/2015 | Doudna et al. | |
| 2015/0272885 A1 | 10/2015 | Ashley et al. | |
| 2015/0284697 A1 | 10/2015 | Haurwitz et al. | |
| 2015/0361406 A1 | 12/2015 | Doudna et al. | |
| 2016/0024568 A1 | 1/2016 | May et al. | |
| 2016/0046949 A1 | 2/2016 | May et al. | |
| 2016/0046961 A1 | 2/2016 | Jinek et al. | |
| 2016/0046962 A1 | 2/2016 | May et al. | |
| 2016/0046963 A1 | 2/2016 | May et al. | |
| 2016/0046978 A1 | 2/2016 | May et al. | |
| 2016/0060653 A1 | 3/2016 | Doudna et al. | |
| 2016/0060654 A1 | 3/2016 | Doudna et al. | |
| 2016/0068864 A1 | 3/2016 | Doudna et al. | |
| 2016/0068887 A1 | 3/2016 | May et al. | |
| 2016/0076020 A1 | 3/2016 | May et al. | |
| 2016/0108470 A1 | 4/2016 | May et al. | |

(Continued)

FOREIGN PATENT DOCUMENTS

WO    WO 2018-107129 A1    6/2018

OTHER PUBLICATIONS

Leenay et al., 2016. Identifying and Visualizing Functional PAM Diversity across CRISPR-Cas Systems. Molecular Cell 62, 137-147 (Year: 2016).*

(Continued)

*Primary Examiner* — Samuel C Woolwine
*Assistant Examiner* — Catherine Konopka
(74) *Attorney, Agent, or Firm* — Helen S. Baca; Madelynne J. Farber; Samantha Updegraff

(57) ABSTRACT

The present invention relates to a CRISPR-Cas based system for targeting nucleic acid sequences. In part, the invention relates to synthetic guiding components for targeting single-stranded sequences, as well as design principles for constructing such components. Also described herein are methods of employing such components, e.g., to repress or activate a desired target within the subject.

33 Claims, 51 Drawing Sheets

Specification includes a Sequence Listing.

(56) References Cited

U.S. PATENT DOCUMENTS

| | | |
|---|---|---|
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0251640 A1 | 9/2016 | May et al. |
| 2016/0289659 A1* | 10/2016 | Doudna ............... C12N 15/113 |
| 2016/0312280 A1 | 10/2016 | May et al. |
| 2016/0319262 A1 | 11/2016 | Doudna et al. |
| 2016/0319349 A1 | 11/2016 | May et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0137801 A1 | 5/2017 | Liras et al. |
| 2017/0166893 A1 | 6/2017 | Doudna et al. |
| 2017/0166958 A1 | 6/2017 | Haurwitz et al. |
| 2017/0175104 A1 | 6/2017 | Doudna et al. |
| 2017/0232115 A1 | 8/2017 | Ashley et al. |
| 2017/0327820 A1 | 11/2017 | May et al. |
| 2017/0360048 A1 | 12/2017 | Nunez et al. |
| 2017/0362644 A1 | 12/2017 | Doudna et al. |
| 2018/0002682 A1 | 1/2018 | Sternberg et al. |
| 2018/0002736 A1 | 1/2018 | O'Connell et al. |
| 2018/0044700 A1 | 2/2018 | Doudna et al. |
| 2018/0142222 A1 | 5/2018 | Sternberg et al. |
| 2018/0208931 A1 | 7/2018 | Doudna et al. |
| 2018/0208976 A1 | 7/2018 | Doudna et al. |
| 2018/0208977 A1 | 7/2018 | Doudna et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237770 A1 | 8/2018 | May et al. |
| 2018/0237801 A1 | 8/2018 | Doudna et al. |
| 2018/0245100 A1 | 8/2018 | Doudna et al. |
| 2018/0245101 A1 | 8/2018 | Doudna et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0273922 A1 | 9/2018 | Doudna et al. |
| 2018/0273981 A1 | 9/2018 | Doudna et al. |
| 2018/0274017 A1 | 9/2018 | Abudayyeh et al. |
| 2018/0282764 A1 | 10/2018 | Jinek et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0298445 A1 | 10/2018 | Abudayyeh et al. |
| 2018/0305773 A1 | 10/2018 | Abudayyeh et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0340218 A1 | 11/2018 | Abudayyeh et al. |
| 2018/0340219 A1 | 11/2018 | Abudayyeh et al. |
| 2018/0346927 A1 | 12/2018 | Doudna et al. |

OTHER PUBLICATIONS

Kleinstiver et al., 2015. Engineered CRISPR-Cas9 nucleases with altered PAM specificities. Nature 523, 481-485 (Year: 2015).*
Mohanraju et al., Diverse evolutionary roots and mechanistic variations of the CRISPR-Cas systems. Science (2016); 353(6299): aad5147 1-12 (Year: 2016).*
Ma et al., Single-Stranded DNA Cleavage by Divergent CRISPR-Cas9 Enzymes. Mol. Cell Nov. 5, 2015;60(3):398-407. And Supplemental Figures. (Year: 2015).*
BLAST (NCBI BLAST alignment, https://blast.ncbi.nlm.nih.gov/Blast.cgi, retrieved from internet [retrieved Jan. 7, 2021]) (Year: 2021).*
The Baltimore classification clusters viruses into families depending on their type of genome. Swiss Institute of Bioinformatics, https://viralzone.expasy.org/254. Available Jun. 11, 2017. Retrieved from the internet [retrieved Jan. 7, 2022] (Year: 2017).*
Chylinski et al.,Classification and evolution of type II CRISPR-Cas systems Nucl Acids Res, 2014, 42(10): 6091-6105 (Year: 2014).*
Ran et al., In vivo genome editing using *Staphylococcus aureus* Cas9. Nature (2015), 250: 186-191 (Year: 2015).*
BLAST alignment of SEQ ID Nos. 100 (SauCas9) and 111 (CjeCas9) https://blast.ncbi.nlm.nih.gov/Blast.cgi?PROGRAM=blastp&PAGE_TYPE=BlastSearch&LINK_LOC=blasthome, retrieved from internet Jul. 31, 2022 (Year: 2022).*
U.S. Appl. No. 15/204,804, filed Jul. 7, 2016, Negrete et al.
U.S. Appl. No. 15/994,711, filed May 31, 2018, Bird et al.
U.S. Appl. No. 16/141,725, filed Sep. 25, 2018, Sasaki et al.
Abudayyeh OO et al., "C2c2 is a single-component programmable RNA-guided RNA-targeting CRISPR effector," *Science* 2016;353(6299):aaf5573 (23 pp.).
Anders C et al., "Structural basis of PAM-dependent target DNA recognition by the Cas9 endonuclease," *Nature* 2014;513(7519):569-73.
Anders S et al., "HTSeq—a Python framework to work with high-throughput sequencing data," *Bioinformatics* 2015;31(2):166-9.
Batra R et al., "Elimination of toxic microsatellite repeat expansion RNA by RNA-targeting Cas9," *Cell* 2017; 170(5):899-912.
Bercy M et al., "Hairpins under tension: RNA versus DNA," *Nucleic Acids Res.* 2015;43(20):9928-36.
Bisaria N et al., "Lessons from enzyme kinetics reveal specificity principles for RNA-guided nucleases in RNA interference and CRISPR-based genome editing," *Cell Syst.* 2017;4(1):21-9.
Chylinski K et al., "Classification and evolution of type II CRISPR-Cas systems," *Nucleic Acids Res.* 2014;42(10):6091-105.
Chylinski K et al., "The tracrRNA and Cas9 families of type II CRISPR-Cas immunity systems," *RNA Biol.* 2013;10(5):726-37.
Cong L et al., "Multiplex genome engineering using CRISPR/Cas systems," *Science* 2013;339(6121):819-23.
Crooks GE et al., "WebLogo: a sequence logo generator," *Genome Res.* 2004;14(6):1188-90.
Dai X et al., "In situ structures of the genome and genome-delivery apparatus in a single-stranded RNA virus," *Nature* 2017;541(7635):112-6.
Deveau H et al., "Phage response to CRISPR-encoded resistance in *Streptococcus thermophilus*" *J. Bacteriol.* 2008;190:1390-400.
East-Seletsky A et al., "Two distinct RNase activities of CRISPR-C2c2 enable guide-RNA processing and RNA detection," *Nature* 2016;538:270-3.
Freier SM et al., "The ups and downs of nucleic acid duplex stability: structure-stability studies on chemically-modified DNA:RNA duplexes," *Nucleic Acids Res.* 1997;25(22):4429-43.
Friedland AE et al., "Characterization of *Staphylococcus aureus* Cas9: a smaller Cas9 for all-in-one adeno-associated virus delivery and paired nickase applications," *Genome Biol.* 2015;16:257 (10 pp.).
Fu BXH et al., "Distinct patterns of Cas9 mismatch tolerance in vitro and in vivo" *Nucleic Acids Res.* 2016;44(11):5365-77.
Fu Y et al., "Improving CRISPR-Cas nuclease specificity using truncated guide RNAs," *Nat. Biotechnol.* 2014;32(3):279-84.
Garneau JE et al., "The CRISPR/Cas bacterial immune system cleaves bacteriophage and plasmid DNA," *Nature* 2010;468(7320):67-71.
Gasiunas G et al., "Cas9-crRNA ribonucleoprotein complex mediates specific DNA cleavage for adaptive immunity in bacteria," *Proc. Nat'l Acad. Sci. USA* 2012;109(39):E2579-86.
Gilbert LA et al., "Genome-scale CRISPR-mediated control of gene repression and activation," *Cell* 2014;159(3):647-61.
Gorski SA et al., "RNA-based recognition and targeting: sowing the seeds of specificity," *Nat. Rev. Mol. Cell Biol.* 2017;18(4):215-28.
Guindon S et al., "New algorithms and methods to estimate maximum-likelihood phylogenies assessing the performance of PhyML 3.0," *Syst. Biol.* 2010;59(3):307-21.
Hirano H et al., "Structure and engineering of *Francisella novicida* Cas9," *Cell* 2016;164(5):950-61.
Hsu PD et al., "DNA targeting specificity of RNA-guided Cas9 nucleases," *Nat. Biotechnol.* 2013;31(9):827-32.
Jiang F et al., "A Cas9-guide RNA complex preorganized for target DNA recognition," *Science* 2015;348:1477-81.
Jiang F et al., "CRISPR-Cas9 structures and mechanisms," *Annu. Rev. Biophys.* 2017;46:505-29.

(56) References Cited

OTHER PUBLICATIONS

Jiang W et al., "RNA-guided editing of bacterial genomes using CRISPR-Cas systems," *Nat. Biotechnol.* 2013;31(3):233-9.
Jinek M et al., "A programmable dual-RNA-guided DNA endonuclease in adaptive bacterial immunity," *Science* 2012;337(6096):816-21.
Kerpedjiev P et al., "Foma (force-directed RNA): simple and effective online RNA secondary structure diagrams," *Bioinformatics* 2015;31(20):3377-9.
Kim E et al., "In vivo genome editing with a small Cas9 orthologue derived from *Campylobacter jejuni,*" *Nat. Commun.* 2017;8:14500 (12 pp.).
Kleinstiver BP et al., "Broadening the targeting range of *Staphylococcus aureus* CRISPR-Cas9 by modifying PAM recognition," *Nat. Biotechnol.* 2015;33(12):1293-8.
Kou R et al., "Benefits and challenges with applying unique molecular identifiers in next generation sequencing to detect low frequency mutations," *PLoS One* 2016;11(1):e0146638 (15 pp.).
Langmead B et al., "Fast gapped-read alignment with Bowtie 2," *Nat. Methods* 2012;9(4):357-9.
Liu Y et al., "Targeting cellular mRNAs translation by CRISPR-Cas9," *Sci. Rep.* 2016;6:29652 (9 pp.).
Loughrey D et al., "SHAPE—Seq 2.0: systematic optimization and extension of high-throughput chemical probing of RNA secondary structure with next generation sequencing," *Nucleic Acids Res.* 2014;42(21):e165 (10 pp.).
Ma E et al., "Single-stranded DNA cleavage by divergent CRISPR-Cas9 enzymes," *Mol. Cell* Nov. 5, 2015;60(3):398-407.
Makarova KS et al., "Evolution and classification of the CRISPR-Cas systems," *Nat. Rev. Microbiol.* 2011;9:467-77.
Martin M, "Cutadapt removes adapter sequences from high-throughput sequencing reads," *EMBnet.journal* 2011;17(1):10-2.
Masella AP et al., "PANDAseq: PAired-eND Assembler for Illumina sequences," *BMC Bioinformatics* 2012;13:31 (7 pp.).
McCarthy DJ et al., "Differential expression analysis of multifactor RNA-Seq experiments with respect to biological variation," *Nucleic Acids Res.* 2012;40(10):4288-97.
Mohanraju P et al., "Diverse evolutionary roots and mechanistic variations of the CRISPR-Cas systems," *Science* 2016;353(6299):aad5147 (14 pp.).
Mout R et al., "Direct cytosolic delivery of CRISPR/Cas9-ribonucleoprotein for efficient gene editing," *ACS Nano* 2017;11(3):2452-8.
Murovec J et al., "New variants of CRISPR RNA-guided genome editing enzymes," *Plant Biotechnol. J.* 2017;15:917-26.
Myhrvold C et al., "Field-deployable viral diagnostics using CRISPR-Cas13," *Science* 2018;360:444-8.
Nelles DA et al., "Applications of Cas9 as an RNA-programmed RNA-binding protein," *Bioessays* 2015;37(7):732-9.
Nelles DA et al., "Programmable RNA tracking in live cells with CRISPR/Cas9," *Cell* 2016;165(2):488-96.
Nishimasu H et al., "Crystal structure of Cas9 in complex with guide RNA and target DNA," *Cell 2014*;156(5):935-49.
Nishimasu H et al., "Crystal structure of *Staphylococcus aureus* Cas9," *Cell* 2015;162(5):1113-26.
O'Connell MR et al., "Programmable RNA recognition and cleavage by CRISPR/Cas9," *Nature* 2014;516(7530):263-6.
Oakes BL et al., "Profiling of engineering hotspots identifies an allosteric CRISPR-Cas9 switch," *Nat. Biotechnol.* 2016;34(6):646-51.
Pei J et al., "PROMALS3D: a tool for multiple protein sequence and structure alignments," *Nucleic Acids Res.* 2008;36(7):2295-300.
Phanstiel DH et al., "Sushi.R: flexible, quantitative and integrative genomic visualizations for publication-quality multi-panel figures," *Bioinformatics* 2014;30(19):2808-10.
Qi LS et al., "Repurposing CRISPR as an RNA-guided platform for sequence-specific control of gene expression," *Cell* 2013;152(5):1173-83.
Ran FA et al., "In vivo genome editing using *Staphylococcus aureus* Cas9," *Nature* 2015;520(7546):186-91.
Rehmsmeier M et al., "Fast and effective prediction of microRNA/target duplexes," *RNA* 2004;10(10):1507-17.
Rio DC, "Filter-binding assay for analysis of RNA-protein interactions," *Cold Spring Harb. Protoc.* 2012;2012(10):1078-81.
Robinson MD et al., "edgeR: a bioconductor package for differential expression analysis of digital gene expression data," *Bioinformatics* 2010;26(1):139-40.
Sampson TR et al., "A CRISPR/Cas system mediates bacterial innate immune evasion and virulence," *Nature* 2013;497(7448):254-7.
Shmakov S et al., "Discovery and functional characterization of diverse class 2 CRISPR-Cas systems," *Mol. Cell.* 2015;60:385-97.
Smargon AA et al., "Cas13b is a type VI-B CRISPR-associated RNA-guided RNase differentially regulated by accessory proteins Csx27 and Csx28," *Mol. Cell*2017;65(4):618-30.
Smith T et al., "UMI-tools: modeling sequencing errors in Unique Molecular Identifiers to improve quantification accuracy," *Genome Res.* 2017;27(3):491-499.
Sternberg SH et al., "DNA interrogation by the CRISPR RNA-guided endonuclease Cas9," *Nature* 2014;507(7490):62-7.
Sternberg SH et al., "Mechanism of substrate selection by a highly specific CRISPR endoribonuclease," *RNA* 2012;18(4):661-72.
Strutt SC et al., "RNA-dependent RNA targeting by CRISPR-Cas9," *eLife* 2018;7:e32724 (17 pp.).
Szczelkun MD et al., "Direct observation of R-loop formation by single RNA-guided Cas9 and Cascade effector complexes," *Proc. Nat'l Acad. Sci. USA* 2014;111(27):9798-803.
Wang AH et al., "Molecular structure of r(GCG)d(TATACGC): a DNA-RNA hybrid helix joined to double helical DNA," *Nature* 1982;299(5884):601-4.
Wright AV et al., "Biology and applications of CRISPR systems: harnessing nature's toolbox for genome engineering," *Cell* 2016;164(1-2):29-44.
Yamada M et al., "Crystal structure of the minimal Cas9 from *Campylobacter jejuni* reveals the molecular diversity in the CRISPR-Cas9 systems," *Mol. Cell.* 2017;65(6):1109-21.
Zhang Y et al., "DNase H activity of *Neisseria meningitidis* Cas9," *Mol. Cell.* 2015;60(2):242-55.
Zuker M, "Mfold web server for nucleic acid folding and hybridization prediction," *Nucleic Acids Res.* 2003;31(13):3406-15.
Zuris JA et al., "Cationic lipid-mediated delivery of proteins enables efficient protein-based genome editing in vitro and in vivo," *Nat. Biotechnol.* 2015;33(1):73-80.

* cited by examiner

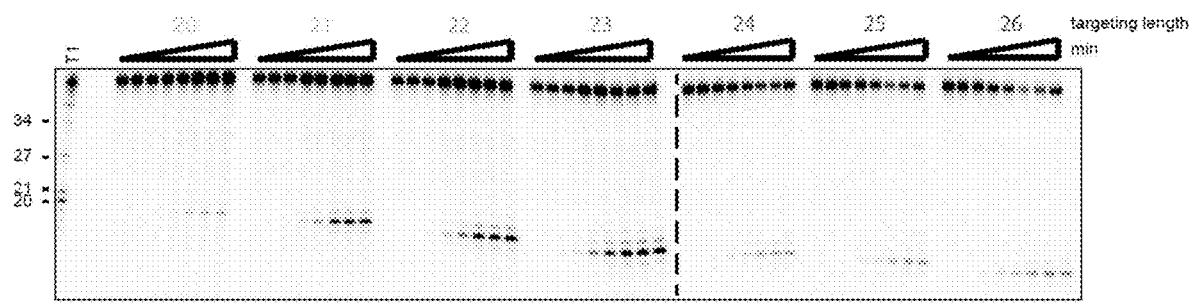
FIG. 7A
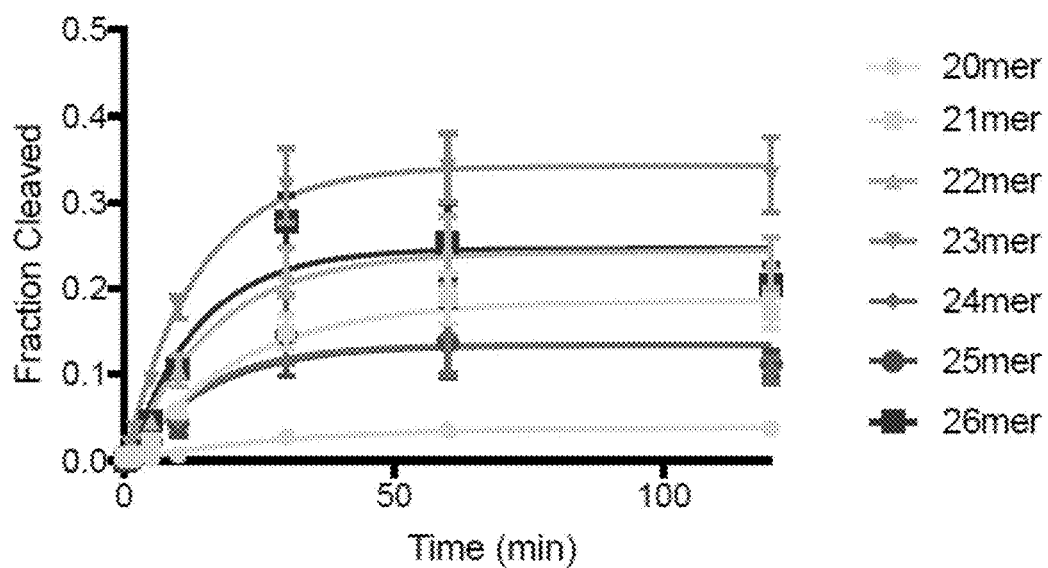
FIG. 7B
FIG. 7C

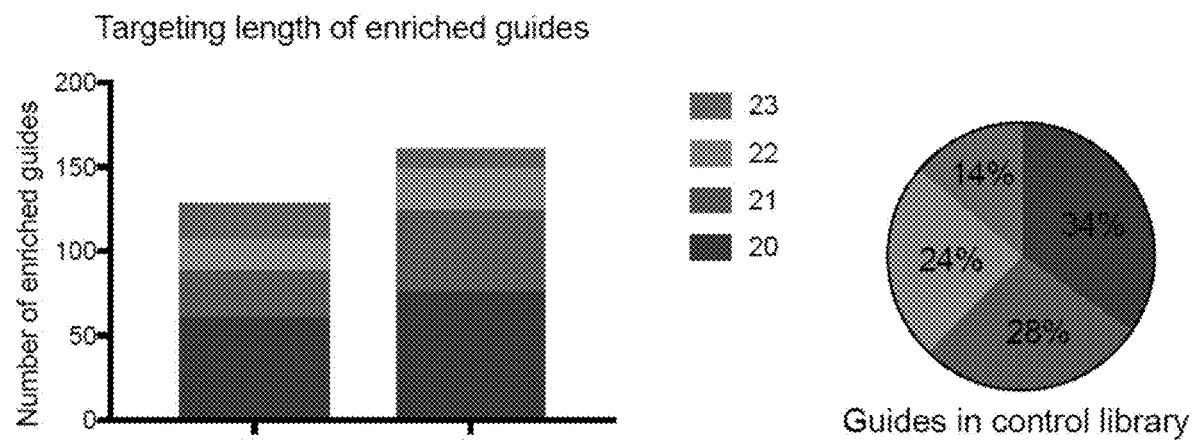
FIG. 11A
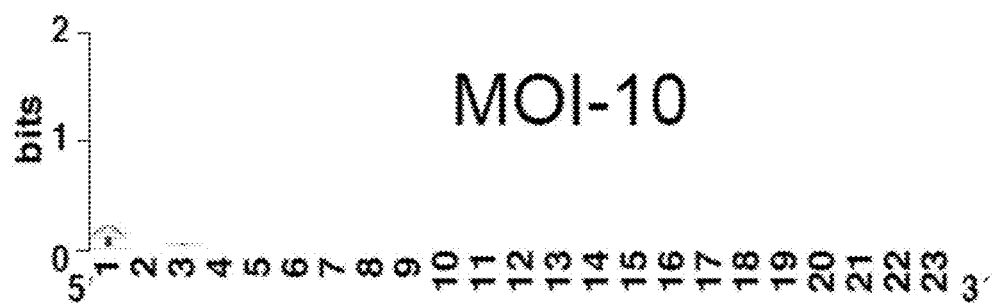
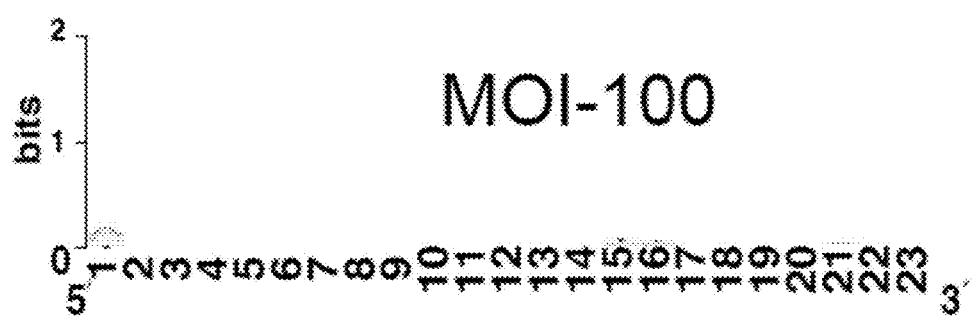
FIG. 11B

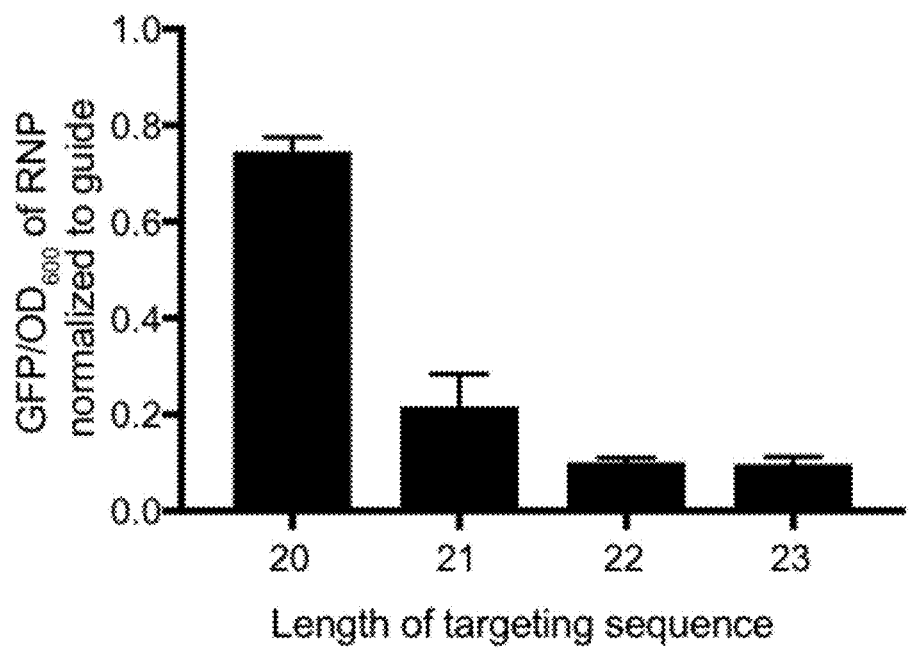
FIG. 15B
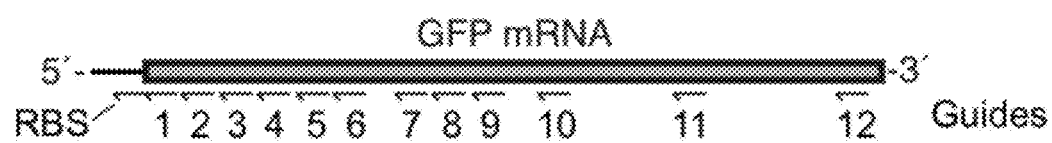
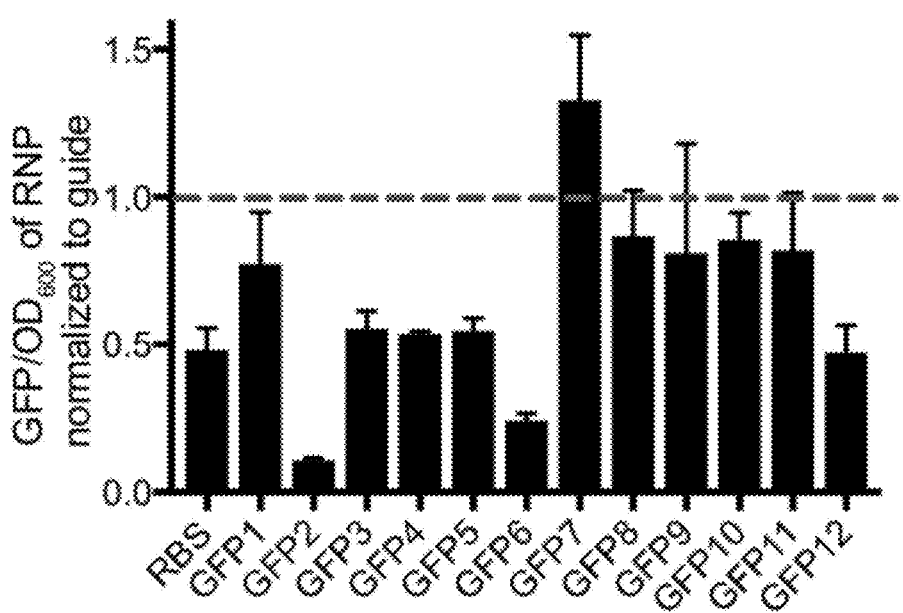
FIG. 15C

```
Wt SauCas9 (SEQ ID NO:100)
   1 MGKRNYILGL DIGITSVGYG IIDYETRDVI DAGVRLFKEA NVENNEGRRS KRGARRLKRR
  61 RRHRIQRVKK LLFDYNLLTD HSELSGINPY EARVKGLSQK LSEEEFSAAL LHLAKRRGVH
 121 NVNEVEEDTG NELSTKEQIS RNSKALEEKY VAELQLERLK KDGEVRGSIN RFKTSDYVKE
 181 AKQLLKVQKA YHQLDQSFID TYIDLLETRR TYYEGPGEGS PFGWKDIKEW YEMLMGHCTY
 241 FPEELRSVKY AYNADLYNAL NDLNNLVITR DENEKLEYYE KFQIIENVFK QKKKPTLKQI
 301 AKEILVNEED IKGYRVTSTG KPEFTNLKVY HDIKDITARK EIIENAELLD QIAKILTIYQ
 361 SSEDIQEELT NLNSELTQEE IEQISNLKGY TGTHNLSLKA INLILDELWH TNDNQIAIFN
 421 RLKLVPKKVD LSQQKEIPTT LVDDFILSPV VKRSFIQSIK VINAIIKKYG LPNDIIIELA
 481 REKNSKDAQK MINEMQKRNR QTNERIEEII RTTGKENAKY LIEKIKLHDM QEGKCLYSLE
 541 AIPLEDLLNN PFNYEVDHII PRSVSFDNSF NNKVLVKQEE NSKKGNRTPF QYLSSSDSKI
 601 SYETFKKHIL NLAKGKGRIS KTKKEYLLEE RDINRFSVQK DFINRNLVDT RYATRGLMNL
 661 LRSYFRVNNL DVKVKSINGG FTSFLRRKWK FKKERNKGYK HHAEDALIIA NADFIFKEWK
 721 KLDKAKKVME NQMFEEKQAE SMPEIETEQE YKEIFITPHQ IKHIKDFKDY KYSHRVDKKP
 781 NRELINDTLY STRKDDKGNT LIVNNLNGLY DKDNDKLKKL INKSPEKLLM YHHDPQTYQK
 841 LKLIMEQYGD EKNPLYKYYE ETGNYLTKYS KKDNGPVIKK IKYYGNKLNA HLDITDDYPN
 901 SRNKVVKLSL KPYRFDVYLD NGVYKFVTVK NLDVIKKENY YEVNSKCYEE AKKLKKISNQ
 961 AEFIASFYNN DLIKINGELY RVIGVNNDLL NRIEVNMIDI TYREYLENMN DKRPPRIIKT
1021 IASKTQSIKK YSTDILGNLY EVKSKKHPQI IKKG
```

FIG. 17A

```
dSauCas9 (SEQ ID NO:101)
   1 MGKRNYILGL AIGITSVGYG IIDYETRDVI DAGVRLFKEA NVENNEGRRS KRGARRLKRR
  61 RRHRIQRVKK LLFDYNLLTD HSELSGINPY EARVKGLSQK LSEEEFSAAL LHLAKRRGVH
 121 NVNEVEEDTG NELSTKEQIS RNSKALEEKY VAELQLERLK KDGEVRGSIN RFKTSDYVKE
 181 AKQLLKVQKA YHQLDQSFID TYIDLLETRR TYYEGPGEGS PFGWKDIKEW YEMLMGHCTY
 241 FPEELRSVKY AYNADLYNAL NDLNNLVITR DENEKLEYYE KFQIIENVFK QKKKPTLKQI
 301 AKEILVNEED IKGYRVTSTG KPEFTNLKVY HDIKDITARK EIIENAELLD QIAKILTIYQ
 361 SSEDIQEELT NLNSELTQEE IEQISNLKGY TGTHNLSLKA INLILDELWH TNDNQIAIFN
 421 RLKLVPKKVD LSQQKEIPTT LVDDFILSPV VKRSFIQSIK VINAIIKKYG LPNDIIIELA
 481 REKNSKDAQK MINEMQKRNR QTNERIEEII RTTGKENAKY LIEKIKLHDM QEGKCLYSLE
 541 AIPLEDLLNN PFNYEVDHII PRSVSFDNSF NNKVLVKQEE ASKKGNRTPF QYLSSSDSKI
 601 SYETFKKHIL NLAKGKGRIS KTKKEYLLEE RDINRFSVQK DFINRNLVDT RYATRGLMNL
 661 LRSYFRVNNL DVKVKSINGG FTSFLRRKWK FKKERNKGYK HHAEDALIIA NADFIFKEWK
 721 KLDKAKKVME NQMFEEKQAE SMPEIETEQE YKEIFITPHQ IKHIKDFKDY KYSHRVDKKP
 781 NRELINDTLY STRKDDKGNT LIVNNLNGLY DKDNDKLKKL INKSPEKLLM YHHDPQTYQK
 841 LKLIMEQYGD EKNPLYKYYE ETGNYLTKYS KKDNGPVIKK IKYYGNKLNA HLDITDDYPN
 901 SRNKVVKLSL KPYRFDVYLD NGVYKFVTVK NLDVIKKENY YEVNSKCYEE AKKLKKISNQ
 961 AEFIASFYNN DLIKINGELY RVIGVNNDLL NRIEVNMIDI TYREYLENMN DKRPPRIIKT
1021 IASKTQSIKK YSTDILGNLY EVKSKKHPQI IKKG
```

FIG. 17B

```
SpyCas9  (SEQ ID NO:102)
     1  MDKKYSIGLD IGTNSVGWAV ITDEYKVPSK KFKVLGNTDR HSIKKNLIGA LLFDSGETAE
    61  ATRLKRTARR RYTRRKNRIC YLQEIFSNEM AKVDDSFFHR LEESFLVEED KKHERHPIFG
   121  NIVDEVAYHE KYPTIYHLRK KLVDSTDKAD LRLIYLALAH MIKFRGHFLI EGDLNPDNSD
   181  VDKLFIQLVQ TYNQLFEENP INASGVDAKA ILSARLSKSR RLENLIAQLP GEKKNGLFGN
   241  LIALSLGLTP NFKSNFDLAE DAKLQLSKDT YDDDLDNLLA QIGDQYADLF LAAKNLSDAI
   301  LLSDILRVNT EITKAPLSAS MIKRYDEHHQ DLTLLKALVR QQLPEKYKEI FFDQSKNGYA
   361  GYIDGGASQE EFYKFIKPIL EKMDGTEELL VKLNREDLLR KQRTFDNGSI PHQIHLGELH
   421  AILRRQEDFY PFLKDNREKI EKILTFRIPY YVGPLARGNS RFAWMTRKSE ETITPWNFEE
   481  VVDKGASAQS FIERMTNFDK NLPNEKVLPK HSLLYEYFTV YNELTKVKYV TEGMRKPAFL
   541  SGEQKKAIVD LLFKTNRKVT VKQLKEDYFK KIECFDSVEI SGVEDRFNAS LGTYHDLLKI
   601  IKDKDFLDNE ENEDILEDIV LTLTLFEDRE MIEERLKTYA HLFDDKVMKQ LKRRRYTGWG
   661  RLSRKLINGI RDKQSGKTIL DFLKSDGFAN RNFMQLIHDD SLTFKEDIQK AQVSGQGDSL
   721  HEHIANLAGS PAIKKGILQT VKVVDELVKV MGRHKPENIV IEMARENQTT QKGQKNSRER
   781  MKRIEEGIKE LGSQILKEHP VENTQLQNEK LYLYYLQNGR DMYVDQELDI NRLSDYDVDH
   841  IVPQSFLKDD SIDNKVLTRS DKNRGKSDNV PSEEVVKKMK NYWRQLLNAK LITQRKFDNL
   901  TKAERGGLSE LDKAGFIKRQ LVETRQITKH VAQILDSRMN TKYDENDKLI REVKVITLKS
   961  KLVSDFRKDF QFYKVREINN YHHAHDAYLN AVVGTALIKK YPKLESEFVY GDYKVYDVRK
  1021  MIAKSEQEIG KATAKYFFYS NIMNFFKTEI TLANGEIRKR PLIETNGETG EIVWDKGRDF
  1081  ATVRKVLSMP QVNIVKKTEV QTGGFSKESI LPKRNSDKLI ARKKDWDPKK YGGFDSPTVA
  1141  YSVLVVAKVE KGKSKKLKSV KELLGITIME RSSFEKNPID FLEAKGYKEV KKDLIIKLPK
  1201  YSLFELENGR KRMLASAGEL QKGNELALPS KYVNFLYLAS HYEKLKGSPE DNEQKQLFVE
  1261  QHKHYLDEII EQISEFSKRV ILADANLDKV LSAYNKHRDK PIREQAENII HLFTLTNLGA
  1321  PAAFKYFDTT IDRKRYTSTK EVLDATLIHQ SITGLYETRI DLSQLGGD
```

FIG. 17C

```
FnoCas9  (SEQ ID NO:103)
     1  MNFKILPIAI DLGVKNTGVF SAFYQKGTSL ERLDNKNGKV YELSKDSYTL LMNNRTARRH
    61  QRRGIDRKQL VKRLFKLIWT EQLNLEWDKD TQQAISFLFN RRGFSFITDG YSPEYLNIVP
   121  EQVKAILMDI FDDYNGEDDL DSYLKLATEQ ESKISEIYNK LMQKILEFKL MKLCTDIKDD
   181  KVSTKTLKEI TSYEFELLAD YLANYSESLK TQKFSYTDKQ GNLKELSYYH HDKYNIQEFL
   241  KRHATINDRI LDTLLTDDLD IWNFNFEKFD FDKNEEKLQN QEDKDHIQAH LHHFVFAVNK
   301  IKSEMASGGR HRSQYFQEIT NVLDENNHQE GYLKNFCENL HNKKYSNLSV KNLVNLIGNL
   361  SNLELKPLRK YFNDKIHAKA DHWDEQKFTE TYCHWILGEW RVGVKDQDKK DGAKYSYKDL
   421  CNELKQKVTK AGLVDFLLEL DPCRTIPPYL DNNNRKPPKC QSLILNPKFL DNQYPNWQQY
   481  LQELKKLQSI QNYLDSFETD LKVLKSSKDQ PYFVEYKSSN QQIASGQRDY KDLDARILQF
   541  IFDRVKASDE LLLNEIYFQA KKLQKASSE LEKLESSKKL DEVIANSQLS QILKSQHTNG
   601  IFEQGTFLHL VCKYYKQRQR ARDSRLYIMP EYRYDKKLHK YNNTGRFDDD NQLLTYCNHK
   661  PRQKRYQLLN DLAGVLQVSP NFLKDKIGSD DDLFISKWLV EHIRGFKKAC EDSLKIQKDN
   721  RGLLNHKINI ARNTKGKCEK EIFNLICKIE GSEDKKGNYK HGLAYELGVL LFGEPNEASK
   781  PEFDRKIKKF NSIYSFAQIQ QIAFAERKGN ANTCAVCSAD NAHRMQQIKI TEPVEDNKDK
   841  IILSAKAQRL PAIPTRIVDG AVKKMATILA KNIVDDNWQN IKQVLSAKHQ LHIPIIITESN
   901  AFEFEPALAD VKGKSLKDRR KKALERISPE NIFKDKNNRI KEFAKGISAY SGANLTDGDF
   961  DGAKEELDHI IPRSHKKYGT LNDEANLICV TRGDNKNKGN RIFCLRDLAD NYKLKQFETT
  1021  DDLEIEKKIA DTIWDANKKD FKFGNYRSFI NLTPQEQKAF RHALFLADEN PIKQAVIRAI
  1081  NNRNRTFVNG TQRYFAEVLA NNIYLRAKKE NLNTDKISFD YFGIPTIGNG RGIAEIRQLY
  1141  EKVDSDIQAY AKGDKPQASY SHLIDAMLAF CIAADEHRND GSIGLEIDKN YSLYPLDKNT
  1201  GEVFTKDIFS QIKITDNEFS DKKLVRKKAI EGFNTHRQMT RDGIYAENYL PILIHKELNE
  1261  VRKGYTWKNS EEIKIFKGKK YDIQQLNNLV YCLKFVDKPI SIDIQISTLE ELRNILTTNN
  1321  IAATAEYYYI NLKTQKLHEY YIENYNTALG YKKYSKEMEF LRSLAYRSER VKIKSIDDVK
  1381  QVLDKDSNFI IGKITLPFKK EWQRLYREWQ NTTIKDDYEF LKSFFNVKSI TKLHKKVRKD
  1441  FSLPISTNEG KFLVKRKTWD NNFIYQILND SDSRADGTKP FIPAFDISKN EIVEAIIDSF
  1501  TSKNIFWLPK NIELQKVDNK NIFAIDTSKW FEVETPSDLR DIGIATIQYK IDNNSRPKVR
  1561  VKLDYVIDDD SKINYFMNHS LLKSRYPDKV LEILKQSTII EFESSGFNKT IKEMLGMKLA
  1621  GIYNETSNN
```

FIG. 17D

CjeCas9   (SEQ ID NO:104)
    1 MARILAFDIG ISSIGWAFSE NDELKDCGVR IFTKVENPKT GESLALPRRL ARSARKRLAR
   61 RKARLNHLKH LIANEFKLNY EDYQSFDESL AKAYKGSLIS PYELRFRALN ELLSKQDFAR
  121 VILHIAKRRG YDDIKNSDDK EKGAILKAIK QNEEKLANYQ SVGEYLYKEY FQKFKENSKE
  181 FTNVRNKKES YERCIAQSFL KDELKLIFKK QREFGFSFSK KFEEEVLSVA FYKRALKDFS
  241 HLVGNCSFFT DEKRAPKNSP LAFMFVALTR IINLLNNLKN TEGILYTKDD LNALLNEVLK
  301 NGTLTYKQTK KLLGLSDDYE FKGEKGTYFI EFKKYKEFIK ALGEHNLSQD DLNEIAKDIT
  361 LIKDEIKLKK ALAKYDLNQN QIDSLSKLEF KDHLNISFKA LKLVTPLMLE GKKYDEACNE
  421 LNLKVAINED KKDFLPAFNE TYYKDEVTNP VVLRAIKEYR KVLNALLKKY GKVHKINIEL
  481 AREVGKNHSQ RAKIEKEQNE NYKAKKDAEL ECEKLGLKIN SKNILKLRLF KEQKEFCAYS
  541 GEKIKISDLQ DEKMLEIDHI YPYSRSFDDS YMNKVLVFTK QNQEKLNQTP FEAFGNDSAK
  601 WQKIEVLAKN LPTKKQKRIL DKNYKDKEQK NFKDRNLNDT RYIARLVLNY TKDYLDFLPL
  661 SDDENTKLND TQKGSKVHVE AKSGMLTSAL RHTWGFSAKD RNNHLHHAID AVIIAYANNS
  721 IVKAFSDFKK EQESNSAELY AKKISELDYK NKRKFFEPFS GFRQKVLDKI DEIFVSKPER
  781 KKPSGALHEE TFRKEEEFYQ SYGGKEGVLK ALELGKIRKV NGKIVKNGDM FRVDIFKHKK
  841 TNKFYAVPIY TMDFALKVLP NKAVARSKKG EIKDWILMDE NYEFCFSLYK DSLILIQTKD
  901 MQEPEFVYYN AFTSSTVSLI VSKHDNKFET LSKNQKILFK NANEKEVIAK SIGIQNLKVF
  961 EKYIVSALGE VTKAEFRQRE DFKK

FIG. 17E

| *In vitro* sgRNAs | Sequence from 5' -> 3' | SEQ ID NO: |
|---|---|---|
| Spy | GGCUGUAAGCGGAUGCCAUAGUUUUAGAGCUAGAAAUAGCAAGUUAAAAUAAGGCUAGUCCGUUAUCAACUUGAAAAAGUGGCACCGAGUCGGUGCUUUUUU | 1 |
| Sau | GGCUGUAAGCGGAUGCCAUAUGGGUUUUAGUACUCUGGAAACAGAAUCUACUAAAACAAGGCAAAAUGCCGUGUUUAUCUCGUCAACUUGUUGGCGAGAUUUUU | 2 |
| Cje | GGCUGUAAGCGGAUGCCAUAUGUUUUAGUCCCUUUUUAAAUUUCUUUAUGGUAAAAUUAUAAUCUCAUAAGAAAUUUAAAAAGGGACUAAAAUAAAGAGUUUGCGGGACUCUGCGGGGUUACAAUCCCCUAAAACCGCUU | 3 |
| Fno | GGCUGUAAGCGGAUGCCAUAUGUUUCAGUUGCGCCGAAAGGCGCUCUGUAAUCAUUUAAAAGUAUUUUGAACGGACCUCUGUUUGACACGUCUG | 4 |
| Sau 20 | GGCTGTAAGCGGATGCCATAGTTTTAGTACTCTGGAAACAGAATCTACTAAAACAAGGCAAAATGCCGTGTTTATCTCGTCAACTTGTTGGCGAGATTTTT | 5 |
| Sau 21 | GGCTGTAAGCGGATGCCATATGTTTTAGTACTCTGGAAACAGAATCTACTAAAACAAGGCAAAATGCCGTGTTTATCTCGTCAACTTGTTGGCGAGATTTTT | 6 |
| Sau 22 | GGCTGTAAGCGGATGCCATATGGTTTTAGTACTCTGGAAACAGAATCTACTAAAACAAGGCAAAATGCCGTGTTTATCTCGTCAACTTGTTGGCGAGATTTTT | 7 |
| Sau 23 | GGCTGTAAGCGGATGCCATATGGGTTTTAGTACTCTGGAAACAGAATCTACTAAAACAAGGCAAAATGCCGTGTTTATCTCGTCAACTTGTTGGCGAGATTTTT | 8 |
| Sau 24 | GGCTGTAAGCGGATGCCATATGGTGTTTTAGTACTCTGGAAACAGAATCTACTAAAACAAGGCAAAATGCCGTGTTTATCTCGTCAACTTGTTGGCGAGATTTTT | 9 |
| Sau 25 | GGCTGTAAGCGGATGCCATATGGTTGTTTTAGTACTCTGGAAACAGAATCTACTAAAACAAGGCAAAATGCCGTGTTTATCTCGTCAACTTGTTGGCGAGATTTTT | 10 |
| Sau 26 | GGCUGUAAGCGGAUGCCAUAUGGUUGGUUUUAGUACUCUGGAAACAGAAUCUACUAAAACAAGGCAAAAUGCCGUGUUUAUCUCGUCAACUUGUUGGCGAGAUUUUU | 11 |

FIG. 18A

| In vitro targets | Sequence from 5' -> 3' | SEQ ID NO: |
|---|---|---|
| ssRNA | GGGCAGCAUUCAACCAUAUGGCAUCCGCUUACAGCCAAGCUGUGACC | 12 |
| dsRNA - TS | GGGCAGCAUUCAACCAUAUGGCAUCCGCUUACAGCCAAGCUGUGACC | 13 |
| dsRNA - NTS | GGUCACAGCUUGGCUGUAAGCGGAUGCCAUAUGGUUGAAUGCUGCCC | 14 |
| ssDNA | GGGCAGCATTCAACCATATGGCATCCGCTTACAGCCAAGCTGTGACC | 15 |
| dsDNA - TS | GGGCAGCATTCAACCATATGGCATCCGCTTACAGCCAAGCTGTGACC | 16 |
| dsDNA - NTS | GGTCACAGCTTGGCTGTAAGCGGATGCCATATGGTTGAATGCTGCCC | 17 |
| PAMmer | CCATATGGTTGAATGCTGCCC | 18 |
| unrelated DNA oligo control PAMmer | GAAGCCCTGAAAGACGCGCAG | 19 |
| NTS ssRNA | GGUCACAGCUUGGCUGUAAGCGGAUGCCAUAUGGUUGAAUGCUGCCC | 20 |
| ssRNA mutant anti-PAM | GGGCAGCCAAGUCCCAUAUGGCAUCCGCUUACAGCCAAGCUGUGACC | 21 |
| dsRNA mutant anti-PAM - TS | GGGCAGCCAAGUCCCAUAUGGCAUCCGCUUACAGCCAAGCUGUGACC | 22 |
| dsRNA mutant anti-PAM - NTS | GGUCACAGCUUGGCUGUAAGCGGAUGCCAUAUGGUUGAAUGCUGCCC | 23 |
| 2nt 3' end of guide NTS | GGUCACAGCUUGGCUGUAAGCGGAUGCCAUAUAAUUGAAUGCUGCCC | 24 |
| 6nt 3' end of guide NTS | GGUCACAGCUUGGCUGUAAGCGGAUGCCUAUAAAUUGAAUGCUGCCC | 25 |
| 12nt 3' end of guide NTS | GGUCACAGCUUGGCUGUAAGCGUUACAGUAUAAAUUGAAUGCUGCCC | 26 |
| 23nt Bubble/mutant anti-PAM NTS | GGUCACAGCUUAAUGAAUUCAAUUACAGUAUAAAUUGAAUGCUGCCC | 27 |
| 2nt 3' end of guide NTS | GGUCACAGCUUAACUGUAAGCGGAUGCCAUAUGGUUGAAUGCUGCCC | 28 |
| 6nt 3' end of guide NTS | GGUCACAGCUUAAUGAAAAGCGGAUGCCAUAUGGUUGAAUGCUGCCC | 29 |
| 12nt 3' end of guide NTS | GGUCACAGCUUAAUGAAUUCAAUAUGCCAUAUGGUUGAAUGCUGCCC | 30 |
| pUC target | GGGCAGCAUUCAACCAUAUGGCAUCCGCUUACAGCCAAGCUGUGACC | 31 |
| ON target | GGGAUUCAACCAUAUGGCAUCCGCUUACAGCCAAGCUG | 32 |
| OFF target | GGGUUUUAUUUUGGAUUUGGAAACGAGAGUUUCUGGUCAUGAA | 33 |
| GFP2 dsDNA - TS | GGGCAGCTGTCCCCATATGGCATCCGCTTACAGCCAAGCTGTGACC | 34 |
| GFP2 dsDNA - NTS | GGTCACAGCTTGGCTGTAAGCGGATGCCATATGGGGACAGCTGCCC | 35 |
| GFP4 dsDNA - TS | GGGCAGCCTGTCCCCATATGGCATCCGCTTACAGCCAAGCTGTGACC | 36 |
| GFP4 dsDNA - NTS | GGTCACAGCTTGGCTGTAAGCGGATGCCATATGGGGACAGGCTGCCC | 37 |
| GFP6 dsDNA - TS | GGGCAGCTATTTGCCATATGGCATCCGCTTACAGCCAAGCTGTGACC | 38 |
| GFP6 dsDNA - NTS | GGTCACAGCTTGGCTGTAAGCGGATGCCATATGGCAAATAGCTGCCC | 39 |

FIG. 18B

| MS2 plaque sgRNAs | Sequence from 5' -> 3' | SEQ ID NO: |
|---|---|---|
| Control | UAGACGAGCCCACCGCUUAGACGUUUUAGUACUCUGGAAACAGAAUCUACUAAAACAAGGCAAAAUGCCGUGUUUAUCUCGUCAACUUGUUGGCGAGAUUUUUU | 40 |
| 23 guide | AUCCCGGGUCCUCUCUUUAGGGGUUUUAGUACUCUGGAAACAGAAUCUACUAAAACAAGGCAAAAUGCCGUGUUUAUCUCGUCAACUUGUUGGCGAGAUUUUUU | 41 |
| 23 guide scr | GUGCUUGUCCCCAGGGUCGUAUGUUUUAGUACUCUGGAAACAGAAUCUACUAAAACAAGGCAAAAUGCCGUGUUUAUCUCGUCAACUUGUUGGCGAGAUUUUUU | 42 |
| 22 guide | GAGAAUCCCGGGUCCUCUCUUUGUUUUAGUACUCUGGAAACAGAAUCUACUAAAACAAGGCAAAAUGCCGUGUUUAUCUCGUCAACUUGUUGGCGAGAUUUUUU | 43 |
| 22 guide scr | GACUCUGCUUGCUGGCACUACUGUUUUAGUACUCUGGAAACAGAAUCUACUAAAACAAGGCAAAAUGCCGUGUUUAUCUCGUCAACUUGUUGGCGAGAUUUUUU | 44 |
| 23 (supp) | ACUUCGCUUGUAGGCACCUUGAUGUUUUAGUACUCUGGAAACAGAAUCUACUAAAACAAGGCAAAAUGCCGUGUUUAUCUCGUCAACUUGUUGGCGAGAUUUUUU | 45 |
| 22 (supp) | AUUCAUAUCAGGCUCCUUACAGGUUUUAGUACUCUGGAAACAGAAUCUACUAAAACAAGGCAAAAUGCCGUGUUUAUCUCGUCAACUUGUUGGCGAGAUUUUUU | 46 |
| 21 (supp) | GAGGUCCCUGGGCCGAAGCCCGUUUUAGUACUCUGGAAACAGAAUCUACUAAAACAAGGCAAAAUGCCGUGUUUAUCUCGUCAACUUGUUGGCGAGAUUUUUU | 47 |
| 20 (supp) | UUCGAUGUAAGUCAAGUUUUGUUUUAGUACUCUGGAAACAGAAUCUACUAAAACAAGGCAAAAUGCCGUGUUUAUCUCGUCAACUUGUUGGCGAGAUUUUUU | 48 |
| 14238 | UAUACCGCUUUCAGUUUUCAUUGUUUUAGUACUCUGGAAACAGAAUCUACUAAAACAAGGCAAAAUGCCGUGUUUAUCUCGUCAACUUGUUGGCGAGAUUUUUU | 49 |
| 14238 scr | GUUCUAUUCUUCAUUUCGUUACAGUUUUAGUACUCUGGAAACAGAAUCUACUAAAACAAGGCAAAAUGCCGUGUUUAUCUCGUCAACUUGUUGGCGAGAUUUUUU | 50 |
| 14210 | UACGGACCGGCUCAGGGAAUUGUUUUAGUACUCUGGAAACAGAAUCUACUAAAACAAGGCAAAAUGCCGUGUUUAUCUCGUCAACUUGUUGGCGAGAUUUUUU | 51 |
| 14210 scr | GGCAUGCGACGUGGAACUCUAUGUUUUAGUACUCUGGAAACAGAAUCUACUAAAACAAGGCAAAAUGCCGUGUUUAUCUCGUCAACUUGUUGGCGAGAUUUUUU | 52 |

FIG. 18C

| GFP sgRNAs | Sequence from 5' -> 3' | SEQ ID NO: |
|---|---|---|
| RBS | CAUGGUACCUUUCUCCUCUUUAAGUUUUAGUACUCUGGAAACAGAAUCUACUAAAACAAGGCAAAAUGCCGUGUUUAUCUCGUCAACUUGUUGGCGAGAUUUUUU | 53 |
| GFP1 | CCAGUGAAAAGUUCUUCUCCUUUGUUUUAGUACUCUGGAAACAGAAUCUACUAAAACAAGGCAAAAUGCCGUGUUUAUCUCGUCAACUUGUUGGCGAGAUUUUUU | 54 |
| GFP2 | CACCAUCUAAUUCAACAAGAAUUGUUUUAGUACUCUGGAAACAGAAUCUACUAAAACAAGGCAAAAUGCCGUGUUUAUCUCGUCAACUUGUUGGCGAGAUUUUUU | 55 |
| GFP3 | CAGAAAAUUUGUGCCCAUUAACAGUUUUAGUACUCUGGAAACAGAAUCUACUAAAACAAGGCAAAAUGCCGUGUUUAUCUCGUCAACUUGUUGGCGAGAUUUUUU | 56 |
| GFP4 | AGCAUCACCUUCACCCUCUCCACGUUUUAGUACUCUGGAAACAGAAUCUACUAAAACAAGGCAAAAUGCCGUGUUUAUCUCGUCAACUUGUUGGCGAGAUUUUUU | 57 |
| GFP5 | AAUUUAAGGGUGAGUUUUCCGUUGUUUUAGUACUCUGGAAACAGAAUCUACUAAAACAAGGCAAAAUGCCGUGUUUAUCUCGUCAACUUGUUGGCGAGAUUUUUU | 58 |
| GFP6 | GAACAGGUAGUUUUCCAGUAGUGGUUUUAGUACUCUGGAAACAGAAUCUACUAAAACAAGGCAAAAUGCCGUGUUUAUCUCGUCAACUUGUUGGCGAGAUUUUUU | 59 |
| GFP7 | CGGGCAUGGCACUCUUGAAAAAGGUUUUAGUACUCUGGAAACAGAAUCUACUAAAACAAGGCAAAAUGCCGUGUUUAUCUCGUCAACUUGUUGGCGAGAUUUUUU | 60 |
| GFP8 | AAAGAUAUAGUGCGUUCCUGUACGUUUUAGUACUCUGGAAACAGAAUCUACUAAAACAAGGCAAAAUGCCGUGUUUAUCUCGUCAACUUGUUGGCGAGAUUUUUU | 61 |
| GFP9 | ACGCGUCUUGUAGGUCCCGUCAUGUUUUAGUACUCUGGAAACAGAAUCUACUAAAACAAGGCAAAAUGCCGUGUUUAUCUCGUCAACUUGUUGGCGAGAUUUUUU | 62 |
| GFP10 | UUUAAAAUCAAUACCCUUUAACUGUUUUAGUACUCUGGAAACAGAAUCUACUAAAACAAGGCAAAAUGCCGUGUUUAUCUCGUCAACUUGUUGGCGAGAUUUUUU | 63 |
| GFP11 | GUUGAACGGAACCAUCUUCAACGGUUUUAGUACUCUGGAAACAGAAUCUACUAAAACAAGGCAAAAUGCCGUGUUUAUCUCGUCAACUUGUUGGCGAGAUUUUUU | 64 |
| GFP12 | AUGUGUAAUCCCAGCAGCAGUUAGUUUUAGUACUCUGGAAACAGAAUCUACUAAAACAAGGCAAAAUGCCGUGUUUAUCUCGUCAACUUGUUGGCGAGAUUUUUU | 65 |
| 20mer | CACCAUCUAAUUCAACAAGAAUUGUUUUAGUACUCUGGAAACAGAAUCUACUAAAACAAGGCAAAAUGCCGUGUUUAUCUCGUCAACUUGUUGGCGAGAUUUUUU | 66 |
| 21mer | CACCAUCUAAUUCAACAAGAAUGUUUUAGUACUCUGGAAACAGAAUCUACUAAAACAAGGCAAAAUGCCGUGUUUAUCUCGUCAACUUGUUGGCGAGAUUUUUU | 67 |
| 22mer | CACCAUCUAAUUCAACAAGAAGUUUUAGUACUCUGGAAACAGAAUCUACUAAAACAAGGCAAAAUGCCGUGUUUAUCUCGUCAACUUGUUGGCGAGAUUUUUU | 68 |
| 23mer | CACCAUCUAAUUCAACAAGAGUUUUAGUACUCUGGAAACAGAAUCUACUAAAACAAGGCAAAAUGCCGUGUUUAUCUCGUCAACUUGUUGGCGAGAUUUUUU | 69 |
| GFP2 noncoding | AAUUCUUGUUGAAUUAGAUGGUGGUUUUAGUACUCUGGAAACAGAAUCUACUAAAACAAGGCAAAAUGCCGUGUUUAUCUCGUCAACUUGUUGGCGAGAUUUUUU | 70 |
| GFP6 noncoding | CACUACUGGAAAACUACCUGUUCGUUUUAGUACUCUGGAAACAGAAUCUACUAAAACAAGGCAAAAUGCCGUGUUUAUCUCGUCAACUUGUUGGCGAGAUUUUUU | 71 |

FIG. 18D

| GFP repression targets | Sequence from 5' -> 3' | SEQ ID NO: |
|---|---|---|
| Spy PAM adjacent | AATTCTTGTTGAATTAGATGGTGA | 72 |
| None PAM adjacent | CACTACTGGAAAACTACCTGTTC | 73 |
| Sau PAM adjacent | ACCTATGGTGTTCAATGCTTTTC | 74 |
| Dual PAM adjacent | ATTGGCGATGGCCCTGTCCTTTT | 75 |
| GFP gene | ATGAGCAAAGGAGAAGAACTTTTCACTGGAGTTGTCCCAATTCTTGTTGAATTAGATGGTGATGTTAATGGGCACAAATTTTCTGTCCGTGGAGAGGGTGAAGGTGATGCTACAAACGGAAAACTCACCCTTAAATTTATTTGCACTACTGGAAAACTACCTGTTCCGTGGCCAACACTTGTCACTACTCTGACCTATGGTGTTCAATGCTTTTCCCGTTATCCGGATCACATGAAACGGCATGACTTTTTCAAGAGTGCCATGCCCGAAGGTTATGTACAGGAACGCACTATATCTTTCAAAGATGACGGGACCTACAAGACGCGTGCTGAAGTCAAGTTTGAAGGTGATACCCTTGTTAATCGTATCGAGTTAAAGGGTATTGATTTTAAAGAAGATGGAAACATTCTTGGACACAAACTCGAGTACAACTTTAACTCACACAATGTATACATCACGGCAGACAAACAAAAGAATGGAATCAAAGCTAACTTCAAAATTCGCCACAACGTTGAAGATGGTTCCGTTCAACTAGCAGACCATTATCAACAAAATACTCCAATTGGCGATGGCCCTGTCCTTTTACCAGACAACCATTACCTGTCGACACAATCTGTCCTTTCGAAAGATCCCAACGAAAAGCGTGACCACATGGTCCTTCTTGAGTTTGTAACTGCTGCTGGGATTACACATGGCATGGATGAGCTCTACAAA | 76 |

FIG. 18E

*Staphylococcus aureus* Cas9 (UniProtKB J7RUA5, SEQ ID NO:110)
```
   1  MKRNYILGLD  IGITSVGYGI  IDYETRDVID  AGVRLFKEAN  VENNEGRRSK  RGARRLKRRR
  61  RHRIQRVKKL  LFDYNLLTDH  SELSGINPYE  ARVKGLSQKL  SEEEFSAALL  HLAKRRGVHN
 121  VNEVEEDTGN  ELSTKEQISR  NSKALEEKYV  AELQLERLKK  DGEVRGSINR  FKTSDYVKEA
 181  KQLLKVQKAY  HQLDQSFIDT  YIDLLETRRT  YYEGPGEGSP  FGWKDIKEWY  EMLMGHCTYF
 241  PEELRSVKYA  YNADLYNALN  DLNNLVITRD  ENEKLEYYEK  FQIIENVFKQ  KKKPTLKQIA
 301  KEILVNEEDI  KGYRVTSTGK  PEFTNLKVYH  DIKDITARKE  IIENAELLDQ  IAKILTIYQS
 361  SEDIQEELTN  LNSELTQEEI  EQISNLKGYT  GTHNLSLKAI  NLILDELWHT  NDNQIAIFNR
 421  LKLVPKKVDL  SQQKEIPTTL  VDDFILSPVV  KRSFIQSIKV  INAIIKKYGL  PNDIIIELAR
 481  EKNSKDAQKM  INEMQKRNRQ  TNERIEEIIR  TTGKENAKYL  IEKIKLHDMQ  EGKCLYSLEA
 541  IPLEDLLNNP  FNYEVDHIIP  RSVSFDNSFN  NKVLVKQEEN  SKKGNRTPFQ  YLSSSDSKIS
 601  YETFKKHILN  LAKGKGRISK  TKKEYLLEER  DINRFSVQKD  FINRNLVDTR  YATRGLMNLL
 661  RSYFRVNNLD  VKVKSINGGF  TSFLRRKWKF  KKERNKGYKH  HAEDALIIAN  ADFIFKEWKK
 721  LDKAKKVMEN  QMFEEKQAES  MPEIETEQEY  KEIFITPHQI  KHIKDFKDYK  YSHRVDKKPN
 781  RELINDTLYS  TRKDDKGNTL  IVNNLNGLYD  KDNDKLKKLI  NKSPEKLLMY  HHDPQTYQKL
 841  KLIMEQYGDE  KNPLYKYYEE  TGNYLTKYSK  KDNGPVIKKI  KYYGNKLNAH  LDITDDYPNS
 901  RNKVVKLSLK  PYRFDVYLDN  GVYKFVTVKN  LDVIKKENYY  EVNSKCYEEA  KKLKKISNQA
 961  EFIASFYNND  LIKINGELYR  VIGVNNDLLN  RIEVNMIDIT  YREYLENMND  KRPPRIIKTI
1021  ASKTQSIKKY  STDILGNLYE  VKSKKHPQII  KKG
```

FIG. 19A

*Campylobacter jejuni* subsp. *jejuni* serotype O:2 Cas9 (UniProtKB Q0P897, SEQ ID NO:111)
```
   1  MARILAFDIG  ISSIGWAFSE  NDELKDCGVR  IFTKVENPKT  GESLALPRRL  ARSARKRLAR
  61  RKARLNHLKH  LIANEFKLNY  EDYQSFDESL  AKAYKGSLIS  PYELRFRALN  ELLSKQDFAR
 121  VILHIAKRRG  YDDIKNSDDK  EKGAILKAIK  QNEEKLANYQ  SVGEYLYKEY  FQKFKENSKE
 181  FTNVRNKKES  YERCIAQSFL  KDELKLIFKK  QREFGFSFSK  KFEEEVLSVA  FYKRALKDFS
 241  HLVGNCSFFT  DEKRAPKNSP  LAFMFVALTR  IINLLNNLKN  TEGILYTKDD  LNALLNEVLK
 301  NGTLTYKQTK  KLLGLSDDYE  FKGEKGTYFI  EFKKYKEFIK  ALGEHNLSQD  DLNEIAKDIT
 361  LIKDEIKLKK  ALAKYDLNQN  QIDSLSKLEF  KDHLNISFKA  LKLVTPLMLE  GKKYDEACNE
 421  LNLKVAINED  KKDFLPAFNE  TYYKDEVTNP  VVLRAIKEYR  KVLNALLKKY  GKVHKINIEL
 481  AREVGKNHSQ  RAKIEKEQNE  NYKAKKDAEL  ECEKLGLKIN  SKNILKLRLF  KEQKEFCAYS
 541  GEKIKISDLQ  DEKMLEIDHI  YPYSRSFDDS  YMNKVLVFTK  QNQEKLNQTP  FEAFGNDSAK
 601  WQKIEVLAKN  LPTKKQKRIL  DKNYKDKEQK  NFKDRNLNDT  RYIARLVLNY  TKDYLDFLPL
 661  SDDENTKLND  TQKGSKVHVE  AKSGMLTSAL  RHTWGFSAKD  RNNHLHHAID  AVIIAYANNS
 721  IVKAFSDFKK  EQESNSAELY  AKKISELDYK  NRKFFEPFS  GFRQKVLDKI  DEIFVSKPER
 781  KKPSGALHEE  TFRKEEEFYQ  SYGGKEGVLK  ALELGKIRKV  NGKIVKNGDM  FRVDIFKHKK
 841  TNKFYAVPIY  TMDFALKVLP  NKAVARSKKG  EIKDWILMDE  NYEFCFSLYK  DSLILIQTKD
 901  MQEPEFVYYN  AFTSSTVSLI  VSKHDNKFET  LSKNQKILFK  NANEKEVIAK  SIGIQNLKVF
 961  EKYIVSALGE  VTKAEFRQRE  DFKK
```

FIG. 19B

*Streptococcus thermophilus* Cas9 (UniProtKB G3ECR1, SEQ ID NO:112)

```
   1 MLFNKCIIIS INLDFSNKEK CMTKPYSIGL DIGTNSVGWA VITDNYKVPS KKMKVLGNTS
  61 KKYIKKNLLG VLLFDSGITA EGRRLKRTAR RRYTRRRNRI LYLQEIFSTE MATLDDAFFQ
 121 RLDDSFLVPD DKRDSKYPIF GNLVEEKVYH DEFPTIYHLR KYLADSTKKA DLRLVYLALA
 181 HMIKYRGHFL IEGEFNSKNN DIQKNFQDFL DTYNAIFESD LSLENSKQLE EIVKDKISKL
 241 EKKDRILKLF PGEKNSGIFS EFLKLIVGNQ ADFRKCFNLD EKASLHFSKE SYDEDLETLL
 301 GYIGDDYSDV FLKAKKLYDA ILLSGFLTVT DNETEAPLSS AMIKRYNEHK EDLALLKEYI
 361 RNISLKTYNE VFKDDTKNGY AGYIDGKTNQ EDFYVYLKNL LAEFEGADYF LEKIDREDFL
 421 RKQRTFDNGS IPYQIHLQEM RAILDKQAKF YPFLAKNKER IEKILTFRIP YYVGPLARGN
 481 SDFAWSIRKR NEKITPWNFE DVIDKESSAE AFINRMTSFD LYLPEEKVLP KHSLLYETFN
 541 VYNELTKVRF IAESMRDYQF LDSKQKKDIV RLYFKDKRKV TDKDIIEYLH AIYGYDGIEL
 601 KGIEKQFNSS LSTYHDLLNI INDKEFLDDS SNEAIIEEII HTLTIFEDRE MIKQRLSKFE
 661 NIFDKSVLKK LSRRHYTGWG KLSAKLINGI RDEKSGNTIL DYLIDDGISN RNFMQLIHDD
 721 ALSFKKKIQK AQIIGDEDKG NIKEVVKSLP GSPAIKKGIL QSIKIVDELV KVMGGRKPES
 781 IVVEMARENQ YTNQGKSNSQ QRLKRLEKSL KELGSKILKE NIPAKLSKID NNALQNDRLY
 841 LYYLQNGKDM YTGDDLDIDR LSNYDIDHII PQAFLKDNSI DNKVLVSSAS NRGKSDDFPS
 901 LEVVKKRKTF WYQLLKSKLI SQRKFDNLTK AERGGLLPED KAGFIQRQLV ETRQITKHVA
 961 RLLDEKFNNK KDENNRAVRT VKIITLKSTL VSQFRKDFEL YKVREINDFH HAHDAYLNAV
1021 IASALLKKYP KLEPEFVYGD YPKYNSFRER KSATEKVYFY SNIMNIFKKS ISLADGRVIE
1081 RPLIEVNEET GESVWNKESD LATVRRVLSY PQVNVVKKVE EQNHGLDRGK PKGLFNANLS
1141 SKPKPNSNEN LVGAKEYLDP KKYGGYAGIS NSFAVLVKGT IEKGAKKKIT NVLEFQGISI
1201 LDRINYRKDK LNFLLEKGYK DIELIIELPK YSLFELSDGS RRMLASILST NNKRGEIHKG
1261 NQIFLSQKFV KLLYHAKRIS NTINENHRKY VENHKKEFEE LFYYILEFNE NYVGAKKNGK
1321 LLNSAFQSWQ NHSIDELCSS FIGPTGSERK GLFELTSRGS AADFEFLGVK IPRYRDYTPS
1381 SLLKDATLIH QSVTGLYETR IDLAKLGEG
```

FIG. 19C

*Streptococcus thermophilus* (strain ATCC BAA-491 / LMD-9) Cas9-1 (UniProtKB Q03LF7, SEQ ID NO:113)

```
   1 MSDLVLGLDI GIGSVGVGIL NKVTGEIIHK NSRIFPAAQA ENNLVRRTNR QGRRLARRKK
  61 HRRVRLNRLF EESGLITDFT KISINLNPYQ LRVKGLTDEL SNEELFIALK NMVKHRGISY
 121 LDDASDDGNS SVGDYAQIVK ENSKQLETKT PGQIQLERYQ TYGQLRGDFT VEKDGKKHRL
 181 INVFPTSAYR SEALRILQTQ QEFNPQITDE FINRYLEILT GKRKYYHGPG NEKSRTDYGR
 241 YRTSGETLDN IFGILIGKCT FYPDEFRAAK ASYTAQEFNL LNDLNNLTVP TETKKLSKEQ
 301 KNQIINYVKN EKAMGPAKLF KYIAKLLSCD VADIKGYRID KSGKAEIHTF EAYRKMKTLE
 361 TLDIEQMDRE TLDKLAYVLT LNTEREGIQE ALEHEFADGS FSQKQVDELV QFRKANSSIF
 421 GKGWHNFSVK LMMELIPELY ETSEEQMTIL TRLGKQKTTS SSNKTKYIDE KLLTEEIYNP
 481 VVAKSVRQAI KIVNAAIKEY GDFDNIVIEM ARETNEDDEK KAIQKIQKAN KDEKDAAMLK
 541 AANQYNGKAE LPHSVFHGHK QLATKIRLWH QQGERCLYTG KTISIHDLIN NSNQFEVDHI
 601 LPLSITFDDS LANKVLVYAT ANQEKGQRTP YQALDSMDDA WSFRELKAFV RESKTLSNKK
 661 KEYLLTEEDI SKFDVRKKFI ERNLVDTRYA SRVVLNALQE HFRAHKIDTK VSVVRGQFTS
 721 QLRRHWGIEK TRDTYHHAV DALIIAASSQ LNLWKKQKNT LVSYSEDQLL DIETGELISD
 781 DEYKESVFKA PYQHFVDTLK SKEFEDSILF SYQVDSKFNR KISDATIYAT RQAKVGKDKA
 841 DETYVLGKIK DIYTQDGYDA FMKIYKKDKS KFLMYRHDPQ TFEKVIEPIL ENYPNKQINE
 901 KGKEVPCNPF LKYKEEHGYI RKYSKKGNGP EIKSLKYYDS KLGNHIDITP KDSNNKVVLQ
 961 SVSPWRADVY FNKTTGKYEI LGLKYADLQF EKGTGTYKIS QEKYNDIKKK EGVDSDSEFK
1021 FTLYKNDLLL VKDTETKEQQ LFRFLSRTMP KQKHYVELKP YDKQKFEGGE ALIKVLGNVA
1081 NSGQCKKGLG KSNISIYKVR TDVLGNQHII KNEGDKPKLD F
```

FIG. 19D

*Streptococcus thermophilus* (strain ATCC BAA-491 / LMD-9) Cas9-2 (UniProtKB Q03JI6, SEQ ID NO:114)

```
   1 MTKPYSIGLD IGTNSVGWAV TTDNYKVPSK KMKVLGNTSK KYIKKNLLGV LLFDSGITAE
  61 GRRLKRTARR RYTRRRNRIL YLQEIFSTEM ATLDDAFFQR LDDSFLVPDD KRDSKYPIFG
 121 NLVEEKAYHD EFPTIYHLRK YLADSTKKAD LRLVYLALAH MIKYRGHFLI EGEFNSKNND
 181 IQKNFQDFLD TYNAIFESDL SLENSKQLEE IVKDKISKLE KKDRILKLFP GEKNSGIFSE
 241 FLKLIVGNQA DFRKCFNLDE KASLHFSKES YDEDLETLLG YIGDDYSDVF LKAKKLYDAI
 301 LLSGFLTVTD NETEAPLSSA MIKRYNEHKE DLALLKEYIR NISLKTYNEV FKDDTKNGYA
 361 GYIDGKTNQE DFYVYLKKLL AEFEGADYFL EKIDREDFLR KQRTFDNGSI PYQIHLQEMR
 421 AILDKQAKFY PFLAKNKERI EKILTFRIPY YVGPLARGNS DFAWSIRKRN EKITPWNFED
 481 VIDKESSAEA FINRMTSFDL YLPEEKVLPK HSLLYETFNV YNELTKVRFI AESMRDYQFL
 541 DSKQKKDIVR LYFKDKRKVT DKDIIEYLHA IYGYDGIELK GIEKQFNSSL STYHDLLNII
 601 NDKEFLDDSS NEAIIEEIIH TLTIFEDREM IKQRLSKFEN IFDKSVLKKL SRRHYTGWGK
 661 LSAKLINGIR DEKSGNTILD YLIDDGISNR NFMQLIHDDA LSFKKKIQKA QIIGDEDKGN
 721 IKEVVKSLPG SPAIKKGILQ SIKIVDELVK VMGGRKPESI VVEMARENQY TNQGKSNSQQ
 781 RLKRLEKSLK ELGSKILKEN IPAKLSKIDN NALQNDRLYL YYLQNGKDMY TGDDLDIDRL
 841 SNYDIDHIIP QAFLKDNSID NKVLVSSASN RGKSDDVPSL EVVKKRKTFW YQLLKSKLIS
 901 QRKFDNLTKA ERGGLSPEDK AGFIQRQLVE TRQITKHVAR LLDEKFNNKK DENNRAVRTV
 961 KIITLKSTLV SQFRKDFELY KVREINDFHH AHDAYLNAVV ASALLKKYPK LEPEFVYGDY
1021 PKYNSFRERK SATEKVYFYS NIMNIFKKSI SLADGRVIER PLIEVNEETG ESVWNKESDL
1081 ATVRRVLSYP QVNVVKKVEE QNHGLDRGKP KGLFNANLSS KPKPNSNENL VGAKEYLDPK
1141 KYGGYAGISN SFTVLVKTI EKGAKKKITN VLEFQGISIL DRINYRKDKL NFLLEKGYKD
1201 IELIIELPKY SLFELSDGSR RMLASILSTN NKRGEIHKGN QIFLSQKFVK LLYHAKRISN
1261 TINENHRKYV ENHKKEFEEL FYYILEFNEN YVGAKKNGKL LNSAFQSWQN HSIDELCSSF
1321 IGPTGSERKG LFELTSRGSA ADFEFLGVKI PRYRDYTPSS LLKDATLIHQ SVTGLYETRI
1381 DLAKLGEG
```

FIG. 19E

*Wolinella succinogenes* Cas9 (UniProtKB Q7MRD3, SEQ ID NO:115)

```
   1 MIERILGVDL GISSLGWAIV EYDKDDEAAN RIIDCGVRLF TAAETPKKKE SPNKARREAR
  61 GIRRVLNRRR VRMNMIKKLF LRAGLIQDVD LDGEGGMFYS KANRADVWEL RHDGLYRLLK
 121 GDELARVLIH IAKHRGYKFI GDDEADEESG KVKKAGVVLR QNFEAAGCRT VGEWLWRERG
 181 ANGKKRNKHG DYEISIHRDL LVEEVEAIFV AQQEMRSTIA TDALKAAYRE IAFFVRPMQR
 241 IEKMVGHCTY FPEERRAPKS APTAEKFIAI SKFFSTVIID NEGWEQKIIE RKTLEELLDF
 301 AVSREKVEFR HLRKFLDLSD NEIFKGLHYK GKPKTAKKRE ATLFDPNEPT ELEFDKVEAE
 361 KKAWISLRGA AKLREALGNE FYGRFVALGK HADEATKILT YYKDEGQKRR ELTKLPLEAE
 421 MVERLVKIGF SDFLKLSLKA IRDILPAMES GARYDEAVLM LGVPHKEKSA ILPPLNKTDI
 481 DILNPTVIRA FAQFRKVANA LVRKYGAFDR VHFELAREIN TKGEIEDIKE SQRKNEKERK
 541 EAADWIAETS FQVPLTRKNI LKKRLYIQQD GRCAYTGDVI ELERLFDEGY CEIDHILPRS
 601 RSADDSFANK VLCLARANQQ KTDRTPYEWF GHDAARWNAF ETRTSAPSNR VRTGKGKIDR
 661 LLKKNFDENS EMAFKDRNLN DTRYMARAIK TYCEQYWVFK NSHTKAPVQV RSGKLTSVLR
 721 YQWGLESKDR ESHTHHAVDA IIIAFSTQGM VQKLSEYYRF KETHREKERP KLAVPLANFR
 781 DAVEEATRIE NTETVKEGVE VKRLLISRPP RARVTGQAHE QTAKPYPRIK QVKNKKKWRL
 841 APIDEEKFES FKADRVASAN QKNFYETSTI PRVDVYHKKG KFHLVPIYLH EMVLNELPNL
 901 SLGTNPEAMD ENFFKFSIFK DDLISIQTQG TPKKPAKIIM GYFKNMHGAN MVLSSINNSP
 961 CEGFTCTPVS MDKKHKDKCK LCPEENRIAG RCLQGFLDYW SQEGLRPPRK EFECDQGVKF
1021 ALDVKKYQID PLGYYYEVKQ EKRLGTIPQM RSAKKLVKK
```

FIG. 19F

```
Wolinella succinogenes Cas9/Csx12 (NCBI WP_011139431.1, SEQ ID NO:116)
   1 MLVSPISVDL GGKNTGFFSF TDSLDNSQSG TVIYDESFVL SQVGRRSKRH SKRNNLRNKL
  61 VKRLFLLILQ EHHGLSIDVL PDEIRGLFNK RGYTYAGFEL DEKKKDALES DTLKEFLSEK
 121 LQSIDRDSDV EDFLNQIASN AESFKDYKKG FEAVFASATH SPNKKLELKD ELKSEYGENA
 181 KELLAGLRVT KEILDEFDKQ ENQGNLPRAK YFEELGEYIA TNEKVKSFFD SNSLKLTDMT
 241 KLIGNISNYQ LKELRRYFND KEMEKGDIWI PNKLHKITER FVRSWHPKND ADRQRRAELM
 301 KDLKSKEIME LLTTTEPVMT IPPYDDMNNR GAVKCQTLRL NEEYLDKHLP NWRDIAKRLN
 361 HGKFNDDLAD STVKGYSEDS TLLHRLLDTS KEIDIYELRG KKPNELLVKT LGQSDANRLY
 421 GFAQNYYELI RQKVRAGIWV PVKNKDDSLN LEDNSNMLKR CNHNPPHKKN QIHNLVAGIL
 481 GVKLDEAKFA EFEKELWSAK VGNKKLSAYC KNIEELRKTH GNTFKIDIEE LRKKDPAELS
 541 KEEKAKLRLT DDVILNEWSQ KIANFFDIDD KHRQRFNNLF SMAQLHTVID TPRSGFSSTC
 601 KRCTAENRFR SETAFYNDET GEFHKKATAT CQRLPADTQR PFSGKIERYI DKLGYELAKI
 661 KAKELEGMEA KEIKVPIILE QNAFEYEESL RKSKTGSNDR VINSKKDRDG KKLAKAKENA
 721 EDRLKDKDKR IKAFSSGICP YCGDTIGDDG EIDHILPRSH TLKIYGTVFN PEGNLIYVHQ
 781 KCNQAKADSI YKLSDIKAGV SAQWIEEQVA NIKGYKTFSV LSAEQQKAFR YALFLQNDNE
 841 AYKKVVDWLR TDQSARVNGT QKYLAKKIQE KLTKMLPNKH LSFEFILADA TEVSELRRQY
 901 ARQNPLLAKA EKQAPSSHAI DAVMAFVARY QKVFKDGTPP NADEVAKLAM LDSWNPASNE
 961 PLTKGLSTNQ KIEKMIKSGD YGQKNMREVF GKSIFGENAI GERYKPIVVQ EGGYYIGYPA
1021 TVKKGYELKN CKVVTSKNDI AKLEKIIKNQ DLISLKENQY IKIFSINKQT ISELSNRYFN
1081 MNYKNLVERD KEIVGLLEFI VENCRYYTKK VDVKFAPKYI HETKYPFYDD WRRFDEAWRY
1141 LQENQNKTSS KDRFVIDKSS LNEYYQPDKN EYKLDVDTQP IWDDFCRWYF LDRYKTANDK
1201 KSIRIKARKT FSLLAESGVQ GKVFRAKRKI PTGYAYQALP MDNNVIAGDY ANILLEANSK
1261 TLSLVPKSGI SIEKQLDKKL DVIKKTDVRG LAIDNNSFFN ADFDTHGIRL IVENTSVKVG
1321 NFPISAIDKS AKRMIFRALF EKEKGKRKKK TTISFKESGP VQDYLKVFLK KIVKIQLRTD
1381 GSISNIVVRK NAADFTLSFR SEHIQKLLK
```

FIG. 19G

```
Staphylococcus lugdunensis Cas9(UniProtKB A0A133QCR3, SEQ ID NO:117)
   1 MNQKFILGLD IGITSVGYGL IDYETKNIID AGVRLFPEAN VENNEGRRSK RGSRRLKRRR
  61 IHRLERVKKL LEDYNLLDQS QIPQSTNPYA IRVKGLSEAL SKDELVIALL HIAKRRGIHK
 121 IDVIDSNDDV GNELSTKEQL NKNSKLLKDK FVCQIQLERM NEGQVRGEKN RFKTADIIKE
 181 IIQLLNVQKN FHQLDENFIN KYIELVEMRR EYFEGPGKGS PYGWEGDPKA WYETLMGHCT
 241 YFPDELRSVK YAYSADLFNA LNDLNNLVIQ RDGLSKLEYH EKYHIIENVF KQKKKPTLKQ
 301 IANEINVNPE DIKGYRITKS GKPQFTEFKL YHDLKSVLFD QSILENEDVL DQIAEILTIY
 361 QDKDSIKSKL TELDILLNEE DKENIAQLTG YTGTHRLSLK CIRLVLEEQW YSSRNQMEIF
 421 THLNIKPKKI NLTAANKIPK AMIDEFILSP VVKRTFGQAI NLINKIIEKY GVPEDIIIEL
 481 ARENNSKDKQ KFINEMQKKN ENTRKRINEI IGKYGNQNAK RLVEKIRLHD EQEGKCLYSL
 541 ESIPLEDLLN NPNHYEVDHI IPRSVSFDNS YHNKVLVKQS ENSKKSNLTP YQYFNSGKSK
 601 LSYNQFKQHI LNLSKSQDRI SKKKKEYLLE ERDINKFEVQ KEFINRNLVD TRYATRELTN
 661 YLKAYFSANN MNVKVKTING SFTDYLRKVW KFKKERNHGY KHHAEDALII ANADFLFKEN
 721 KKLKAVNSVL EKPEIESKQL DIQVDSEDNY SEMFIIPKQV QDIKDFRNFK YSHRVDKKPN
 781 RQLINDTLYS TRKKDNSTYI VQTIKDIYAK DNTTLKKQFD KSPEKFLMYQ HDPRTFEKLE
 841 VIMKQYANEK NPLAKYHEET GEYLTKYSKK NNGPIVKSLK YIGNKLGSHL DVTHQFKSST
 901 KKLVKLSIKP YRFDVYLTDK GYKFITISYL DVLKKDNYYY IPEQKYDKLK LGKAIDKNAK
 961 FIASFYKNDL IKLDGEIYKI IGVNSDTRNM IELDLPDIRY KEYCELNNIK GEPRIKKTIG
1021 KKVNSIEKLT TDVLGNVFTN TQYTKPQLLF KRGN
```

FIG. 19H

*Staphylococcus pseudintermedius ED99* Cas9 (GenBank ADX75954.1, SEQ ID NO:118)

```
   1 MGRKPYILSL DIGTGSVGYA CMDKGFNVLK YHDKDALGVY LFDGALTAQE RRQFRTSRRR
  61 KNRRIKRLGL LQELLAPLVQ NPNFYQFQRQ FAWKNDNMDF KNKSLSEVLS FLGYESKKYP
 121 TIYHLQEALL LKDEKFDPEL IYMALYHLVK YRGHFLFDHL KIENLTNNDN MHDFVELIET
 181 YENLNNIKLN LDYEKTKVIY EILKDNEMTK NDRAKRVKNM EKKLEQFSIM LLGLKFNEGK
 241 LFNHADNAEE LKGANQSHTF ADNYEENLTP FLTVEQSEFI ERANKIYLSL TLQDILKGKK
 301 SMAMSKVAAY DKFRNELKQV KDIVYKADST RTQFKKIFVS SKKSLKQYDA TPNDQTFSSL
 361 CLFDQYLIRP KKQYSLLIKE LKKIIPQDSE LYFEAENDTL LKVLNTTDNA SIPMQINLYE
 421 AETILRNQQK YHAEITDEMI EKVLSLIQFR IPYYVGPLVN DHTASKFGWM ERKSNESIKP
 481 WNFDEVVDRS KSATQFIRRM TNKCSYLINE DVLPKNSLLY QEMEVLNELN ATQIRLQTDP
 541 KNRKYRMMPQ IKLFAVEHIF KKYKTVSHSK FLEIMLNSNH RENFMNHGEK LSIFGTQDDK
 601 KFASKLSSYQ DMTKIFGDIE GKRAQIEEII QWITIFEDKK ILVQKLKECY PELTSKQINQ
 661 LKKLNYSGWG RLSEKLLTHA YQGHSIIELL RHSDENFMEI LTNDVYGFQN FIKEENQVQS
 721 NKIQHQDIAN LTTSPALKKG IWSTIKLVRE LTSIFGEPEK IIMEFATEDQ QKGKKQKSRK
 781 QLWDDNIKKN KLKSVDEYKY IIDVANKLNN EQLQQEKLWL YLSQNGKCMY SGQSIDLDAL
 841 LSPNATKHYE VDHIFPRSFI KDDSIDNKVL VIKKMNQTKG DQVPLQFIQQ PYERIAYWKS
 901 LNKAGLISDS KLHKLMKPEF TAMDKEGFIQ RQLVETRQIS VHVRDFLKEE YPNTKVIPMK
 961 AKMVSEFRKK FDIPKIRQMN DAHHAIDAYL NGVVYHGAQL AYPNVDLFDF NFKWEKVREK
1021 WKALGEFNTK QKSRELFFFK KLEKMEVSQG ERLISKIKLD MNHFKINYSR KLANIPQQFY
1081 NQTAVSPKTA ELKYESNKSN EVVYKGLTPY QTYVVAIKSV NKKGKEKMEY QMIDHYVFDF
1141 YKFQNGNEKE LALYLAQREN KDEVLDAQIV YSLNKGDLLY INNHPCYFVS RKEVINAKQF
1201 ELTVEQQLSL YNVMNNKETN VEKLLIEYDF IAEKVINEYH HYLNSKLKEK RVRTFFSESN
1261 QTHEDFIKAL DELFKVVTAS ATRSDKIGSR KNSMTHRAFL GKGKDVKIAY TSISGLKTTK
1321 PKSLFKLAES RNEL
```

FIG. 19I

*Helicobacter mustelae* Cas9 (UniProtKB D3UFL8, SEQ ID NO:119)

```
   1 MIRTLGIDIG IASIGWAVIE GEYTDKGLEN KEIVASGVRV FTKAENPKNK ESLALPRTLA
  61 RSARRRNARK KGRIQQVKHY LSKALGLDLE CFVQGEKLAT LFQTSKDFLS PWELRERALY
 121 RVLDKEELAR VILHIAKRRG YDDITYGVED NDSGKIKKAI AENSKRIKEE QCKTIGEMMY
 181 KLYFQKSLNV RNKKESYNRC VGRSELREEL KTIFQIQQEL KSPWVNEELI YKLLGNPDAQ
 241 SKQEREGLIF YQRPLKGFGD KIGKCSHIKK GENSPYRACK HAPSAEEFVA LTKSINFLKN
 301 LTNRHGLCFS QEDMCVYLGK ILQEAQKNEK GLTYSKLKLL LDLPSDFEFL GLDYSGKNPE
 361 KAVFLSLPST FKLNKITQDR KTQDKIANIL GANKDWEAIL KELESLQLSK EQIQTIKDAK
 421 LNFSKHINLS LEALYHLLPL MREGKRYDEG VEILQERGIF SKPQPKNRQL LPPLSELAKE
 481 ESYFDIPNPV LRRALSEFRK VVNALLEKYG GFHYFHIELT RDVCKAKSAR MQLEKINKKN
 541 KSENDAASQL LEVLGLPNTY NNRLKCKLWK QQEEYCLYSG EKITIDHLKD QRALQIDHAF
 601 PLSRSLDDSQ SNKVLCLTSS NQEKSNKTPY EWLGSDEKKW DMYVGRVYSS NFSPSKKRKL
 661 TQKNFKERNE EDFLARNLVD TGYIGRVTKE YIKHSLSFLP LPDGKKEHIR IISGSMTSTM
 721 RSFWGVQEKN RDHHLHHAQD AIIIACIEPS MIQKYTTYLK DKETHRLKSH QKAQILREGD
 781 HKLSLRWPMS NFKDKIQESI QNIIPSHHVS HKVTGELHQE TVRTKEFYYQ AFGGEEGVKK
 841 ALKFGKIREI NQGIVDNGAM VRVDIFKSKD KGKFYAVPIY TYDFAIGKLP NKAIVQGKKN
 901 GIIKDWLEMD ENYEFCFSLF KNDCIKIQTK EMQEAVLAIY KSTNSAKATI ELEHLSKYAL
 961 KNEDEEKMFT DTDKEKNKTM TRESCGIQGL KVFQKVKLSV LGEVLEHKPR NRQNIALKTT
1021 PKHV
```

FIG. 19J

*Streptococcus pasteurianus* Cas9 (UniProtKB A0A135YMA6, SEQ ID NO:120)

```
   1 MTKKNYSIGL DIGTNSVGWA VITDDYKVPA KKMKVLGNTD KKYIKKNLLG ALLFDSGETA
  61 EATRLKRTAR RRYTRRKNRL RYLQEIFAEE MTKVDESFFY RLDESFLTTD EKDFERHPIF
 121 GNKADEIKYH QEFPTIYHLR KHLADSSEKA DLRLVYLALA HMIKFRGHFL IEGELNAENT
 181 DVQKIFADFV GVYDRTFDDS HLSEITVDAA SILTEKISKS RRLENLIKYY PTEKKNTLFG
 241 NLIALALGLQ PNFKMNFKLS EDAKLQFSKD SYNEDLEELL GKIGDDYADL FTSAKNLYDA
 301 ILLSGILTVD DNSTKAPLSA SMIKRYAEHH EDLEKLKEFI KANKSELYHD IFKDETKNGY
 361 AGYIENGVKQ DEFYKYLKNT LSKIAGSDYF LDKIEREDFL RKQRTFDNGS IPHQIHLQEM
 421 HAILRRQGDY YPFLKENQDR IEKILTFRIP YYVGPLARKD SRFSWAEYHS DEKITPWNFD
 481 KVIDKEKSAE KFITRMTLND LYLPEEKVLP KHSHVYETYA VYNELTKIKY VNEQGKDSFF
 541 DSNMKQEIFD HVFKENRKVT KEKLLNYLNK EFPEYRIKDL IGLDKENKSF NASLGTYHDL
 601 KKILDKAFLD DKVNEEVIED IIKTLTLFED KDMIHERLQK YSDIFTADQL KKLERRHYTG
 661 WGRLSYKLIN GIRNKENNKT ILDYLIDDGS ANRNFMQLIN DDTLPFKQII QKSQVVGDVD
 721 DIEAVVHDLP GSPAIKKGIL QSVKIVDELV KVMGDNPDNI VIEMARENQT TNRGRSQSQQ
 781 RLKKLQNSLK ELGSNILNEE KPSYIEDKVE NSHLQNDQLF LYYIQNGKDM YTGDELDIDH
 841 LSDYDIDHII PQAFIKDDSI DNRVLTSSAK NRGKSDDVPS LDIVRARKAE WVRLYKSGLI
 901 SKRKFDNLTK AERGGLTEAD KAGFIKRQLV ETRQITKHVA QILDARFNTE SDENDKVIRD
 961 VKVITLKSNL VSQFRKDFEF YKVREINDYH HAHDAYLNAV VGTALLKKYP KLASEFVYGE
1021 YKKYDVHKLI AKSSDDHSEM GKATAKYFFY SNLMNFFKRV IRYSNGKVIV RPVVEYSKDT
1081 EDIAWDKKSN FRTICKVLSY PQVNIVKKVE TQTGGFSKES ILPKGDSDKL IPRKTKKAYW
1141 DTKKYGGFDS PTVAYSVFVV ADVEKGKAKK LKTVKELVGI SIMERSFFEE NPVEFLENKG
1201 YHNIREDKLI KLPKYSLFEF EGGKRRLLAS ASELQKGNEM VIPGHLVKLL YHAQRINSFN
1261 STKYLDYVSA HKKEFEKVLS CVEDFANLYV DVEKNLSKIR AVADSMDNFS IEEISNSFIN
1321 LLTLTALGAP ADFNFLGEKI PRKRYTSTKE CLNATLIHQS ITGLYETRID LSKIGEE
```

FIG. 19K

*Streptococcus pasteurianus* (strain ATCC 43144 / JCM 5346 / CDC 1723-81) Cas9 (UniProtKB F5X275, SEQ ID NO:121)

```
   1 MTNGKILGLD IGIASVGVGI IEAKTGKVVH ANSRLFSAAN AENNAERRGF RGSRRLNRRK
  61 KHRVKRVRDL FEKYGIVTDF RNLNLNPYEL RVKGLTEQLK NEELFAALRT ISKRRGISYL
 121 DDAEDDSTGS TDYAKSIDEN RRLLKNKTPG QIQLERLEKY GQLRGNFTVY DENGEAHRLI
 181 NVFSTSDYEK EARKILETQA DYNKKITAEF IDDYVEILTQ KRKYYHGPGN EKSRTDYGRF
 241 RTDGTTLENI FGILIGKCNF YPDEYRASKA SYTAQEYNFL NDLNNLKVST ETGKLSTEQK
 301 ESLVEFAKNT ATLGPAKLLK EIAKILDCKV DEIKGYREDD KGKPDLHTFE PYRKLFNLE
 361 SINIDDLSRE VIDKLADILT LNTEREGIED AIKRNLPNQF TEEQISEIIK VRKSQSTAFN
 421 KGWHSFSAKL MNELIPELYA TSDEQMTILT RLEKFKVNKK SSKNTKTIDE KEVTDEIYNP
 481 VVAKSVRQTI KIINAAVKKY GDFDKIVIEM PRDKNADDEK KFIDKRNKEN KKEKDDALKR
 541 AAYLYNSSDK LPDEVFHGNK QLETKIRLWY QQGERCLYSG KPISIQELVH NSNNFEIDHI
 601 LPLSLSFDDS LANKVLVYAW TNQEKGQKTP YQVIDSMDAA WSFREMKDYV LKQKGLGKKK
 661 RDYLLTTENI DKIEVKKKFI ERNLVDTRYA SRVVLNSLQS ALRELGKDTK VSVVRGQFTS
 721 QLRRKWKIDK SRETYHHHAV DALIIAASSQ LKLWEKQDNP MFVDYGKNQV VDKQTGEILS
 781 VSDDEYKELV FQPPYQGFVN TISSKGFEDE ILFSYQVDSK YNRKVSDATI YSTRKAKIGK
 841 DKKEETYVLG KIKDIYSQNG FDTFIKKYNK DKTQFLMYQK DSLTWENVIE VILRDYPTTK
 901 KSEDGKNDVK CNPFEEYRRE NGLICKYSKK GKGTPIKSLK YYDKKLGNCI DITPEESRNK
 961 VILQSINPWR ADVYFNPETL KYELMGLKYS DLSFEKGTGN YHISQEKYDA IKEKEGIGKK
1021 SEFKFTLYRN DLILIKDIAS GEQEIYRFLS RTMPNVNHYV ELKPYDKEKF DNVQELVEAL
1081 GEADKVGRCI KGLNKPNISI YKVRTDVLGN KYFVKKKGDK PKLDFKNNKK
```

FIG. 19L

| Portion | Sequence (e.g., for use with Sau Cas9) | SEQ ID NO: |
|---|---|---|
| Y | GTTTTAGTACTCTGTAATTTTAGGTATGAGGTAGAC | 150 |
| | GUUUUAGUACUCUGUAAUUUUAGGUAUGAGGUAGAC | 151 |
| | GTTTTAGTACTCTG | 152 |
| | GUUUUAGUACUCUG | 153 |
| | GTTTTAGTACTCT | 154 |
| | GUUUUAGUACUCU | 155 |
| L | GGAAAC | 156 |
| | GGAAA | 157 |
| | GAAA | 158 |
| | TGAA | 159 |
| | UGAA | 160 |
| | AAA | 161 |
| Z | ATTGTACTTATACCTAAAATTACAGAATCTACTAAAACAAGGCAAAATGCCGTGTTTATCTCGTCAACTTGTTGGCGAGATTTTT | 162 |
| | AUUGUACUUAUACCUAAAAUUACAGAAUCUACUAAAACAAGGCAAAAUGCCGUGUUUAUCUCGUCAACUUGUUGGCGAGAUUUUU | 163 |
| | ACAGAATCTACTAAAACAAGGCAAAATGCCGTGTTTATCTCGTCAACTTGTTGGCGAGATTTTT | 164 |
| | ACAGAAUCUACUAAAACAAGGCAAAAUGCCGUGUUUAUCUCGUCAACUUGUUGGCGAGAUUUUU | 165 |
| | ACAGAATCTACTAAAACAAGGCAAAATGCCGTGTTTATCTCGTCAACTTGTTGGCGAGATTTTT | 166 |
| | ACAGAATCTACTAAAACAAGGCAAAATGCCGTGTTTATCTCGTCAACTTGTTGGCGAGATTTT | 167 |
| | ACAGAATCTACTAAAACAAGGCAAAATGCCGTGTTTATCTCGTCAACTTGTTGGCGAGATTT | 168 |
| | ACAGAATCTACTAAAACAAGGCAAAATGCCGTGTTTATCTCGTCAACTTGTTGGCGAGATT | 169 |
| | ACAGAATCTACTAAAACAAGGCAAAATGCCGTGTTTATCTCGTCAACTTGTTGGCGAGAT | 170 |
| | CAGAATCTACTAAAACAAGGCAAAATGCCGTGTTTATCTCGTCAACTTGTTGGCGAGATTTTT | 171 |
| | CAGAAUCUACUAAAACAAGGCAAAAUGCCGUGUUUAUCUCGUCAACUUGUUGGCGAGAUUUUU | 172 |
| | CAGAATCTACTAAAACAAGGCAAAATGCCGTGTTTATCTCGTCAACTTGTTGGCGAGATTTT | 173 |
| | CAGAATCTACTAAAACAAGGCAAAATGCCGTGTTTATCTCGTCAACTTGTTGGCGAGATTT | 174 |
| | CAGAATCTACTAAAACAAGGCAAAATGCCGTGTTTATCTCGTCAACTTGTTGGCGAGATT | 175 |
| | CAGAATCTACTAAAACAAGGCAAAATGCCGTGTTTATCTCGTCAACTTGTTGGCGAGAT | 176 |
| | CAGAATCTACTAAAACAAGGCAAAATGCCG | 177 |
| | CAGAATCTACTAAAACAAGGCAAAATGCC | 178 |

FIG. 20C

| Portion | Sequence (e.g., for use with Cje Cas9) | SEQ ID NO: |
|---|---|---|
| Y | GUUUUAGUCCCUUUUUAAAUUUCUUUAUGGUAAAU | 179 |
| | GTTTTAGTCCCTTTTTAAATTTCTTTATGGTAAAT | 180 |
| | GTTTTAGTCCCTT | 181 |
| | GUUUUAGUCCCUU | 182 |
| | GTTTTAGTCCCT | 183 |
| | GUUUUAGUCCCU | 184 |
| | GTTTTAGTCCC | 185 |
| | GUUUUAGUCCC | 186 |
| L | GAAA | 187 |
| | TGAA | 188 |
| | UGAA | 189 |
| | ATATTCAA | 190 |
| | TGTGGAAATATA | 191 |
| Z | AAGAAATTTAAAAAGGGACTAAAATAAAGAGTTTGCGGGACTCTGCGGGGTTACAATCCCCTAAAACCGCTTTT | 192 |
| | AAGAAAUUUAAAAAGGGACUAAAAUAAAGAGUUUGCGGGACUCUGCGGGGUUACAAUCCCCUAAAACCGCUUUU | 193 |
| | AGGGACTAAAATAAAGAGTTTGCGGGACTCTGCGGGGTTACAATCCCCTAAAACCGCTTTTTTT | 194 |
| | AGGGACUAAAAUAAAGAGUUUGCGGGACUCUGCGGGGUUACAAUCCCCUAAAACCGCUUUUUUU | 195 |
| | AGGGACTAAAATAAAGAGTTTGCGGGACTCTGCGGGGTTACAATCCCCTAAAACCGCTTTTTT | 196 |
| | AGGGACTAAAATAAAGAGTTTGCGGGACTCTGCGGGGTTACAATCCCCTAAAACCGCTTTTT | 197 |
| | AGGGACTAAAATAAAGAGTTTGCGGGACTCTGCGGGGTTACAATCCCCTAAAACCGCTTTT | 198 |
| | AGGGACTAAAATAAAGAGTTTGCGGGACTCTGCGGGGTTACAATCCCCTAAAACCGCTTT | 199 |
| | AGGGACTAAAATAAAGAGTTTGCGGGACTCTGCGGGGTTACAATCCCCTAAAACCGCTT | 200 |
| | AGGGACTAAAATAAAGAGTTTGCGGGACTCTGCGGGGTTACAATCCCCTAAAACCGCT | 201 |
| | AGGGACTAAAATAAAGAGTTTGCGGGACTCTGCGGGGTTACAATCCCCTAAAACCGC | 202 |
| | GGGACTAAAATAAAGAGTTTGCGGGACTCTGCGGGGTTACAATCCCCTAAAACCGCTTTTTTT | 203 |
| | GGGACUAAAAUAAAGAGUUUGCGGGACUCUGCGGGGUUACAAUCCCCUAAAACCGCUUUUUUU | 204 |
| | GGGACTAAAATAAAGAGTTTGCGGGACTCTGCGGGGTTACAATCCCCTAAAACCGCTTTTTT | 205 |
| | GGGACTAAAATAAAGAGTTTGCGGGACTCTGCGGGGTTACAATCCCCTAAAACCGCTTTTT | 206 |
| | GGGACTAAAATAAAGAGTTTGCGGGACTCTGCGGGGTTACAATCCCCTAAAACCGCTTTT | 207 |
| | GGGACTAAAATAAAGAGTTTGCGGGACTCTGCGGGGTTACAATCCCCTAAAACCGCTTT | 208 |
| | GGGACTAAAATAAAGAGTTTGCGGGACTCTGCGGGGTTACAATCCCCTAAAACCGCTT | 209 |
| | GGGACTAAAATAAAGAGTTTGCGGGACTCTGCGGGGTTACAATCCCCTAAAACCGCT | 210 |
| | GGGACTAAAATAAAGAGTTTGCGGGACTCTGCGGGGTTACAATCCCCTAAAACCGC | 211 |
| | GGGACTAAAATAAAGAGTTTGCGGGACTCT | 212 |

FIG. 20D

| Portion | Sequence (e.g., for use with Sth Cas9) | SEQ ID NO: |
|---|---|---|
| Y | GTTTTTGTACTCTCAAGATTTAAGTAACTGTACAAC | 213 |
| | GTTTTAGAGCTGTGTTGTTTCGAATGGTTCCAAAAC | 214 |
| | GGTTTGAAACCATTCGAAACAACACAGCGAGTTAAA | 215 |
| | CTTACACAGTTACTTAAATCTTGCAGAAGCTACAAA | 216 |
| | GTTTTTGTACTCTCAAGATTTAAGTAA | 217 |
| | GTTTTTGTACTCTCAAGA | 218 |
| | GTTTTTGTACTCTCAAG | 219 |
| | GTTTTAGAGCTGTGTTGTTTCGAATGG | 220 |
| | GTTTTAGAGCTGTGTTG | 221 |
| | GGTTTGAAACCATTCGA | 222 |
| | GGTTTGAAACCATTCG | 223 |
| | CTTACACAGTTACTTAA | 224 |
| | CTTACACAGTTACTT | 225 |
| L | GAAA | 226 |
| | TAAA | 227 |
| | ATTT | 228 |
| | GTTT | 229 |
| | TTT | 230 |
| | AAA | 231 |
| Z | TTACTTAAATCTTGCAGAAGCTACAAAGATAAGGCTTCATGCCGAAATCAACACCCTGTCATTTTATGGCAGGGTGTTTTCGTTATTTAA | 232 |
| | GTAAGGGGCGCCTTACACAGTTACTTAAATCTTGCAGAAGCTACAAAGATAAGGCTTCATGCCGAAATCAACACCCTGTCATTTTATGGCAGGGTGTTTTCGTT | 233 |
| | CTTACACAGTTACTTAAATCTTGCAGAAGCTACAAAGATAAGGCTTCATGCCGAAATCAACACCCTGTCATTTTATGGCAGGGTGTTTTCGTT | 234 |
| | CTTACACAGTTACTTAAATCTTGCAGAAGCTACAAA | 235 |
| | TTGTGGTTTGAAACCATTCGAAACAACACAGCGAGTTAAAATAAGGCTTAGTCCGTACTCAACTTGAAAAGGTGGCACCGATTCGGTGTTTTTTTT | 236 |
| | GGTTTGAAACCATTCGAAACAACACAGCGAGTTAAAATAAGGCTTAGTCCGTACTCAACTTGAAAAGGTGGCACCGATTCGGTGTTTTTTTT | 237 |
| | GGTTTGAAACCATTCGAAACAACACAGCGAGTTAAA | 238 |

FIG. 20E

| Portion | Sequence (e.g., for use with Wsu Cas9) | SEQ ID NO: |
|---|---|---|
| Y | GCAACACTTTATAGCAAATCCGCTTAGCCTGTGAAAC | 239 |
| | ATTATAGCGAGGAATGGCTGAGTAGGCGGCTATAAC | 240 |
| | GCAACACTTTATAGCAAATCCGCT | 241 |
| | GCAACACTTTATAGC | 242 |
| | GCAACACTTTA | 243 |
| Z | TTTCAAGGCATCGAACGGATTTGCTATAAAGTGTTGC | 244 |
| | TTTGTTAAAGCTGGATGGGATTATTATAGAGTGTTGC | 245 |
| | ATAGCCGCTGCCTACTCAGCCATTTAGCGCAGCGAC | 246 |
| | TATAGAGTGTTGC | 247 |
| | TAGAGUGTTGC | 248 |
| | TATAAAGTGTTGC | 249 |
| | TAAAGTGTTGC | 250 |

FIG. 20F

| Portion | Sequence (e.g., for use with Slu Cas9) | SEQ ID NO: |
|---|---|---|
| Y | GTTTTAGTACTCTGTAATTTTAGGTATAAGTGATAC | 251 |
| | TTTTAGTACTCTGTAATTTTAGGTATAAGTGATAC | 252 |
| | TCTGTAATTTTAGGTATAAGT | 253 |
| Z | CTTGTACTTATACCTAAAATTACAGAATCTACTGAA | 254 |
| | ACTTATACCTAAAATTACAGA | 255 |

FIG. 20G

| Portion | Sequence (e.g., for use with Sps Cas9) | SEQ ID NO: |
|---|---|---|
| Y | GTTTTAGCACTATGTTTATTTAGAAAGAGGTAAAAC | 256 |
| | ACTATGTTTATTTAGAAAGAGGTAAAAC | 257 |
| Z | GTTTTACTTCTTTCTAAATAAACATAGTTAAGTTAA | 258 |
| | GTTTTACTTCTTTCTAAATAAACATAGT | 259 |

FIG. 20H

| Portion | Sequence (e.g., for use with Hmu Cas9) | SEQ ID NO: |
|---|---|---|
| Y | ATTTTAGCATAAACATATTTATGAAGTGGCTAAAAC | 260 |
| Z | GTATTTGTCAATAAATATACTTTATAATGGCAAGAT | 261 |

FIG. 20I

| Portion | Sequence (e.g., for use with Spa Cas9) | SEQ ID NO: |
|---|---|---|
| Y | GTTTTTGTACTCTCAAGATTTAAGTAA | 262 |
| | GTTTTTGTACTCTCAAGA | 263 |
| | GTTTTTGTACTCTCAAG | 264 |
| L | TTAA | 265 |
| | TAAA | 266 |
| | TTT | 267 |
| | TTA | 268 |
| | AAA | 269 |
| Z | TTACTTAAATCTTGCTGAGCCTACAAAGATAAGGCTTTATGCCGAATTCAAGCACCCCATGTTTTGACATGAGGTGCTTTT | 270 |
| | TCTTGCTGAGCCTACAAAGATAAGGCTTTATGCCGAATTCAAGCACCCCATGTTTTGACATGAGGTGCTTTT | 271 |
| | CTTGCTGAGCCTACAAAGATAAGGCTTTATGCCGAATTCAAGCACCCCATGTTTTGACATGAGGTGCTTTT | 272 |
| | TCTTGCTGAGCCTACAAAGATAAGGCTTTATGCC | 273 |

FIG. 20J

| | Exemplary synthetic guiding components | SEQ ID NO: |
|---|---|---|
| Sau | W-X-GUUUAGUACUCUG-GAAA-CAGAAUCUACUAAAACAAGGCAAAAUGCCGUGUUAUCUCGUCAACUUGUUGGGAGAUUUU | 274 |
| | W-X-GTTTTAGTACTCTG-GAAA-CAGAATCTACTAAAACAAGGCAAAATGCCGTGTTTATCTCGTCAACTTGTTGGCGAGATTTT | 275 |
| | W-X-GUUUAGUACUCUG-GAAA-CAGAAUCUACUAAAACAAGGCAAAAUGCCGUGUUAUCUCGUCAACUUGUUGGGCGAGAUUU | 276 |
| | W-X-GTTTTAGTACTCTG-GAAA-CAGAATCTACTAAAACAAGGCAAAATGCCGTGTTTATCTCGTCAACTTGTTGGCGAGATT | 277 |
| Cje | W-X-GTTTTAGTCCCT-GAAA-AGGGACTAAAATAAAGAGTTTGCGGGACTCTGCGCGGGTTACAATCCCCTAAAACCGC | 278 |
| | W-X-GTTTTAGTCCCT-GAAAA-GGGACTAAAATAAAGAGTTTGCGGGACTCTGCGGGGTTACAATCCCCTAAAACCGC | 279 |
| | W-X-GUUUAGUCCCU-GAAAA-GGGACUAAAAUAAAGAGUUUGCGGGACUCUGCGGGUUACAAUCCCCUAAAACCGC | 280 |
| | W-X-GTTTTAGTCCCT-GAAA-AGGGACTAAAATAAAGAGTTTGCGGGACTCTGCGGGGTTACAATCCCCTAAAACCGCTTTTTT | 281 |
| | W-X-GTTTTAGTCCCT-GAAA-AGGGACTAAAATAAAGAGTTTGCGGGACTCTGCGGGGTTACAATCCCCTAAAACCGCTTTTTT | 282 |
| | W-X-GTTTTAGTCCC-TGAA-GGGACTAAAATAAAGAGTTTGCGGGACTCTGCGGGGTTACAATCCCCTAAAACCGCTTTTT | 283 |
| | W-X-GTTTTAGTCCT-TGTGGAAATATA-AGGGACTAAAATAAAGAGTTTGCGGGTTACAATCCCCTAAAACCGCTTTTTT | 284 |
| | W-X-GTTTTAGTCCT-ATATTCAA-AGGGACTAAAATAAAGAGTTTGCGGGACTCTGCGGGGTTACAATCCCCTAAAACCGCTTTTTT | 285 |
| Spa | W-X-GTTTTGTACTCTCAAGA-TTAA-TCTTGCTGAGCCTACAAAGATAAGGCTTTATGCCGAATTCAAGCACCCCATGTTTTGACATGAGGTGCTTTT | 286 |
| | W-X-GTTTTGTACTCTCAAGA-TTAA-TCTTGCTGAGCCTACAAAGATAAGGCTTTATGCCGAATTCAAGCACCCCATGTTTTGACATGAGGTGC | 287 |
| | W-X-GTTTTGTACTCTCAAGA-TAA-TCTTGCTGAGCCTACAAAGATAAGGCTTTATGCCGAATTCAAGCACCACCCATGTTTTGACATGAGGTGCTTTT | 288 |
| | W-X-GTTTTGTACTCTCAAGA-TAA-TCTTGCTGAGCCTACAAAGATAAGGCTTTATGCCGAATTCAAGCACCACCCATGTTTTGACATGAGGTGC | 289 |
| | W-X-GTTTTGTACTCTCAAG-AAA-CTTGCTGAGCCTACAAAGATAAGGCTTTATGCCGAATTCAAGCACCCCCATGTTTGACATGAGGTGCTTTT | 290 |
| | W-X-GTTTTGTACTCTCAAG-AAA-CTTGCTGAGCCTACAAAGATAAGGCTTTATGCCGAATTCAAGCACCCCCATGTTTGACATGAGGTGC | 291 |
| | W-X-GTTTTGTACTCTCAAG-AAT-CTTGCTGAGCCTACAAAGATAAGGCTTTATGCCGAATTCAAGCACCCCCATGTTTTGACATGAGGTGCTTTT | 292 |
| | W-X-GTTTTGTACTCTCAAG-AAT-CTTGCTGAGCCTACAAAGATAAGGCTTTATGCCGAATTCAAGCACCCCCATGTTTTGACATGAGGTGC | 293 |

CRISPR-CAS BASED SYSTEM FOR TARGETING SINGLE-STRANDED SEQUENCES

CROSS-REFERENCE TO RELATED APPLICATION

This application claims the benefit of U.S. Provisional Application No. 62/598,888, filed Dec. 14, 2017, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration and under Contract No. MCB-1244557 awarded by the National Science Foundation. The Government has certain rights in the invention.

REFERENCE TO A SEQUENCE LISTING APPENDIX

A sequence listing appendix including an ASCII formatted file accompanies this application. The appendix includes a file named "SD14537.1_ST25.txt," created on Dec. 13, 2018 (size of 3.63 megabytes), which is hereby incorporated by reference in its entirety.

FIELD OF THE INVENTION

The present invention relates to a CRISPR-Cas based system for targeting nucleic acid sequences. In part, the invention relates to synthetic guiding components for targeting single-stranded sequences and complexes including such components. Also described herein are methods of employing such components, e.g., to repress or activate a desired target within a subject.

BACKGROUND OF THE INVENTION

CRISPR-Cas based systems have emerged as a promising methodology for gene editing. Many studies focus on the use of a particular endonuclease, Cas9, and its function as a DNA endonuclease that cleaves DNA. Targeting and editing of RNA remains relatively unexplored. Accordingly, there is a need for synthetic constructs and methods that provide specific targeting and modulation of RNA targets.

SUMMARY OF THE INVENTION

The present invention relates, in part, to use of a CRISPR-Cas based system for programmable RNA binding and cleavage. In particular, we present evidence that *Staphylococcus aureus* (Sau) Cas9 is a dual DNA/RNA targeting nuclease, which can be employed in cells to regulate genes on both the transcriptional and translational level in parallel by accounting for target site PAM adjacency. In one non-limiting example, SauCas9 RNA-scission depends on a single-guide RNA (sgRNA) and does not need a PAMmer sequence, thereby simplifying outstanding issues in delivery. Due to its small size, SauCas9 can be efficiently delivered to cells by use of a vector including a nucleic acid sequence encoding SauCas9 (e.g., an adeno-associated virus (AAV) vector). Further, Cas9-sgRNA could be delivered as a ribonucleoprotein complex, further providing additional in vitro and in vivo delivery options. Finally, the RNA-targeting capability of SauCas9 offers the advantage of modulating targets that rely primarily on RNA molecules (e.g., repressing viruses whose lifecycles consist of solely RNA molecules, thereby inaccessible to DNA cleavage) and of providing orthogonal, non-DNA targets for gene modification (e.g., regulating site-specific epigenetic modifications of RNA or providing isoform-specific targeting of RNA transcripts).

Accordingly, in a first non-limiting aspect, the present invention features a synthetic guiding component including a structure having the formula (I): W—X—Y-L-Z or salt thereof (e.g., 5'-W—X—Y-L-Z-3'). In one embodiment, W is an optional third portion including a nucleic acid sequence of from about 1 to 20 nucleic acids; X is a targeting portion including a nucleic acid sequence configured to bind to a target site of a single-stranded target sequence; Y is a first portion including a nucleic acid sequence configured to interact with a nuclease configured to bind and/or cleave the single-stranded target sequence; L is a linker; and Z is a second portion including a nucleic acid sequence configured to interact with the nuclease and the first portion.

In some embodiments, Y includes a nucleic acid sequence having at least 80% sequence identity (e.g., 85%, 90%, 95%, 96%, 97%, 98%, 99%, or 100% sequence identity) to any one of SEQ ID NOs:150-155, 179-186, 213-225, 239-243, 251-253, 256, 257, 260, and 262-264, or a complement of any of these, or a fragment thereof (e.g., a fragment having of from about 10 to about 50 nucleotides, such as of from about 10 to 15, 10 to 20, 10 to 25, 10 to 30, 10 to 35, 10 to 40, 10 to 45, 12 to 15, 12 to 20, 12 to 25, 12 to 30, 12 to 35, 12 to 40, 12 to 45, 12 to 50, 15 to 20, 15 to 25, 15 to 30, 15 to 35, 15 to 40, 15 to 45, 15 to 50, 20 to 25, 20 to 30, 20 to 35, 20 to 40, 20 to 45, 20 to 50, 25 to 30, 25 to 35, 25 to 40, 25 to 45, or 25 to 50 nucleotides).

In some embodiments, Z includes a nucleic acid sequence having at least 80% sequence identity (e.g., 85%, 90%, 95%, 96%, 97%, 98%, 99%, or 100% sequence identity) to any one of SEQ ID NOs:162-178, 192-212, 232-238, 244-250, 254, 255, 258, 259, 261, and 270-273, or a complement of any of these, or a fragment thereof (e.g., a fragment having of from about 10 to about 100 nucleotides, such as of from about 10 to 30, 10 to 40, 10 to 50, 10 to 60, 10 to 70, 10 to 80, 10 to 90, 20 to 30, 20 to 40, 20 to 50, 20 to 60, 20 to 70, 20 to 80, 20 to 90, 20 to 100, 30 to 40, 30 to 50, 30 to 60, 30 to 70, 30 to 80, 30 to 90, 30 to 100, 40 to 50, 40 to 60, 40 to 70, 40 to 80, 40 to 90, 40 to 100, 50 to 60, 50 to 70, 50 to 80, 50 to 90, 50 to 100, 60 to 80, 60 to 90, 60 to 100, 70 to 80, 70 to 90, 70 to 100, 80 to 90, 80 to 100, or 90 to 100 nucleotides).

In some embodiments, L includes a bond or a nucleic acid sequence having at least 80% sequence identity (e.g., 85%, 90%, 95%, 96%, 97%, 98%, 99%, or 100% sequence identity) to any one of SEQ ID NOs:156-161, 187-191, 226-231, and 265-269, or a complement of any of these, or a fragment thereof (e.g., a fragment having of from about 1 to about 10 nucleotides, such as from about 1 to 4, 1 to 5, 1 to 6, 1 to 7, 1 to 8, 1 to 9, 2 to 4, 2 to 5, 2 to 6, 2 to 7, 2 to 8, 2 to 9, or 2 to 10 nucleotides).

In some embodiments, the synthetic guiding component includes a nucleic acid sequence having at least 80% sequence identity (e.g., 85%, 90%, 95%, 96%, 97%, 98%, 99%, or 100% sequence identity) to any one of SEQ ID NOs:274-293, or a complement of any of these, or a fragment thereof (e.g., a fragment having of from about 75 to 250 nucleotides, such as of from about 75 to 100, 75 to 150, 75 to 200, 80 to 100, 80 to 150, 80 to 200, 80 to 250, 90 to 100, 90 to 150, 90 to 200, 90 to 250, 100 to 150, 100 to 200, 100 to 250, 150 to 200, 150 to 250, or 200 to 250 nucleotides, in which the length can either include or exclude W and/or X).

In some embodiments, W and/or Y includes one or more modified nucleic acids (e.g., a modified nucleic acid configured to promote access of the Cas enzyme to the target site, such as a sugar modification and/or a backbone modification) or bulges (e.g., inclusion of one or more unpaired nucleotides upon binding of W to a portion of the target sequence or upon binding of Y to the target sequence).

In some embodiments, X is configured to bind to the target site of a single-stranded human RNA target sequence (e.g., a mRNA target sequence) or a single-stranded pathogen target sequence (e.g., a viral RNA sequence).

In some embodiments, X has a length of from about 10 to about 30 nucleotides (e.g., of from about 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 27, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 nucleotides).

In some embodiments, Y includes a nucleic acid sequence having at least 80% sequence identity to any one of SEQ ID NOs:150-155, or a complement of any of these, or a fragment thereof; L is a bond or includes a nucleic acid sequence having at least 80% sequence identity to any one of SEQ ID NOs:156-161, or a complement of any of these, or a fragment thereof; and/or Z includes a nucleic acid sequence having at least 80% sequence identity to any one of SEQ ID NOs:162-178, or a complement of any of these, or a fragment thereof. In further embodiments, the nuclease includes an amino acid sequence having at least 80% sequence identity to any one of wild-type *Staphylococcus aureus* Cas9 (e.g., SauCas, e.g., SEQ ID NO:100 or 110), dSauCas9 (e.g., D10A and N580A, SEQ ID NO:101), or a fragment thereof.

In some embodiments, Y includes a nucleic acid sequence having at least 80% sequence identity to any one of SEQ ID NOs:179-186, or a complement of any of these, or a fragment thereof; L is a bond or includes a nucleic acid sequence having at least 80% sequence identity to any one of SEQ ID NOs:187-191, or a complement of any of these, or a fragment thereof; and Z includes a nucleic acid sequence having at least 80% sequence identity to any one of SEQ ID NOs:192-212, or a complement of any of these, or a fragment thereof. In further embodiments, the nuclease includes an amino acid sequence having at least 80% sequence identity to any one of *Campylobacter jejuni* Cas9 (CjeCas9, e.g., SEQ ID NO:104), *Campylobacter jejuni* subsp. *jejuni* serotype 0:2 Cas9 (e.g., SEQ ID NO:111), or a fragment thereof.

In some embodiments, Y includes a nucleic acid sequence having at least 80% sequence identity to any one of SEQ ID NOs: 213-225, or a complement of any of these, or a fragment thereof; L is a bond or includes a nucleic acid sequence having at least 80% sequence identity to any one of SEQ ID NOs:226-231, or a complement of any of these, or a fragment thereof; and Z includes a nucleic acid sequence having at least 80% sequence identity to any one of SEQ ID NOs:232-238, or a complement of any of these, or a fragment thereof. In further embodiments, the nuclease includes an amino acid sequence having at least 80% sequence identity to any one of *Streptococcus thermophilus* Cas9 (e.g., SEQ ID NO:112), *Streptococcus thermophilus* (strain ATCC BAA-491/MD-9) Cas9-1 (e.g., SEQ ID NO:113), *Streptococcus thermophilus* (strain ATCC BAA-491/MD-9) Cas9-2 (e.g., SEQ ID NO:114), or a fragment thereof.

In some embodiments, Y includes a nucleic acid sequence having at least 80% sequence identity to any one of SEQ ID NOs:239-243, or a complement of any of these, or a fragment thereof; and Z includes a nucleic acid sequence having at least 80% sequence identity to any one of SEQ ID NOs:244-250, or a complement of any of these, or a fragment thereof. In further embodiments, the nuclease includes an amino acid sequence having at least 80% sequence identity to any one of *Wolinella succinogenes* Cas9 (e.g., SEQ ID NO:115), *Wolinella succinogenes* Cas9/Csx12 (e.g., SEQ ID NO:116), or a fragment thereof.

In some embodiments, Y includes a nucleic acid sequence having at least 80% sequence identity to any one of SEQ ID NOs:251-253, or a complement of any of these, or a fragment thereof; and Z includes a nucleic acid sequence having at least 80% sequence identity to any one of SEQ ID NOs:254-255, or a complement of any of these, or a fragment thereof. In further embodiments, the nuclease includes an amino acid sequence having at least 80% sequence identity to *Staphylococcus lugdunensis* Cas9 (e.g., SEQ ID NO:117) or a fragment thereof. In some embodiments, Y includes a nucleic acid sequence having at least 80% sequence identity to any one of SEQ ID NOs:256-257, or a complement of any of these, or a fragment thereof; and Z includes a nucleic acid sequence having at least 80% sequence identity to any one of SEQ ID NOs:258-259, or a complement of any of these, or a fragment thereof. In further embodiments, the nuclease includes an amino acid sequence having at least 80% sequence identity to *Staphylococcus* pseudintermedius Cas9 (e.g., *Staphylococcus* pseudintermedius ED99 Cas9 or SEQ ID NO:118) or a fragment thereof.

In some embodiments, Y includes a nucleic acid sequence having at least 80% sequence identity to SEQ ID NO:260, or a complement of any of these, or a fragment thereof; and Z includes a nucleic acid sequence having at least 80% sequence identity to SEQ ID NO:261, or a complement of any of these, or a fragment thereof. In further embodiments, the nuclease includes an amino acid sequence having at least 80% sequence identity to *Helicobacter mustelae* Cas9 (e.g., SEQ ID NO:119) or a fragment thereof.

In some embodiments, Y includes a nucleic acid sequence having at least 80% sequence identity to any one of SEQ ID NOs:262-264, or a complement of any of these, or a fragment thereof; L is a bond or includes a nucleic acid sequence having at least 80% sequence identity to any one of SEQ ID NOs:265-269, or a complement of any of these, or a fragment thereof; and Z includes a nucleic acid sequence having at least 80% sequence identity to any one of SEQ ID NOs:270-273, or a complement of any of these, or a fragment thereof. In further embodiments, the nuclease includes an amino acid sequence having at least 80% sequence identity to any one of *Streptococcus pasteurianus* Cas9 (e.g., SEQ ID NO:120), *Streptococcus pasteurianus* (strain ATCC 43144/JCM 5346/CDC 1723-81) Cas9 (e.g., SEQ ID NO:121, or a fragment thereof.

In a second non-limiting aspect, the invention features a nucleoprotein complex including: a synthetic guiding component (e.g., any described herein); and a nuclease configured to bind and/or cleave a single-stranded target sequence.

In some embodiments, the nuclease is a Cas protein or a modified form thereof. In other embodiments, the nuclease includes an amino acid sequence having at least 80% sequence identity (e.g., 85%, 90%, 95%, 96%, 97%, 98%, 99%, or 100% sequence identity) to any one of SEQ ID NOs:100, 101, 104, and 110-121, or a fragment thereof (e.g., as described herein).

In other embodiments, the complex further includes one or more inorganic ions (e.g., monovalent and/or divalent ions) associated with the complex (e.g., any useful ion or combinations thereof, such as potassium (e.g., $K^+$), magnesium (e.g., $Mg^{2+}$), lithium (e.g., $Li^+$), sodium (e.g., $Na^+$), calcium (e.g., $Ca^{2+}$), manganese (e.g., $Mn^{2+}$), cadmium (e.g., $Cd^{2+}$), lead (e.g., PV), europium (e.g., $Eu^{3+}$), and thallium (e.g., $Tl^+$) ions, as well as combinations thereof).

In a third aspect, the invention features a method of modulating a single-stranded target sequence (e.g., an exogenous single-stranded target sequence) in a subject (e.g., any described herein). In some embodiments, the method includes: identifying an enriched single-stranded target sequence that is enriched in the subject when exposed to an exogenous pathogen (e.g., a virus, a bacterium, or any other described herein), as compared to the subject that is not exposed to the exogenous pathogen; designing a targeting portion of a synthetic guiding component (e.g., where the targeting portion is configured to bind to the enriched single-stranded target sequence, and/or where the synthetic guiding component is any described herein); and administering an effective amount of the synthetic guiding component, or a nucleic acid sequence encoding the synthetic guiding component, to the subject.

In some embodiments, the enriched single-stranded target sequence includes a portion of a genome for a pathogen (e.g., a virus), and the targeting portion of the synthetic guiding component is sufficiently complementary to the portion of the genome. In other embodiments, the enriched single-stranded target sequence has low structural complexity (e.g., characterized by a lack of secondary structure, such as a lack of base pairing, a lack of junctions, or a lack of stacking regions; or characterized by regions of accessible nucleic acids, such as loop regions or bulge regions having unpaired bases).

In a third non-limiting aspect, the invention features a method of modulating a target within a subject, the method including: identifying a single-stranded target sequence within the subject; designing a targeting portion of a synthetic guiding component (e.g., where the targeting portion is configured to bind to the single-stranded target sequence, and/or where the synthetic guiding component includes any structure described herein); and administering an effective amount of the synthetic guiding component, or a nucleic acid sequence encoding the synthetic guiding component, to the subject.

In a fourth non-limiting aspect, the invention features a method of modulating a target within a pathogen (e.g., a genome of the pathogen). In some embodiments, the method includes: identifying a single-stranded target sequence within the pathogen; designing a targeting portion of a synthetic guiding component (e.g., where the targeting portion is configured to bind to the single-stranded target sequence, and/or where the synthetic guiding component includes any structure described herein); and administering an effective amount of the synthetic guiding component, or a nucleic acid sequence encoding the synthetic guiding component, to the pathogen.

In any embodiment herein, the method includes identifying a single-stranded target sequence. In some embodiments, the identifying step includes determining a secondary structure of the single-stranded target sequence and choosing a target site in proximity to the secondary structure characterized by low structural complexity (e.g., characterized by a lack of secondary structure, such as a lack of base pairing interactions, a lack of junctions, or a lack of stacking regions; or characterized by regions of accessible nucleic acids, such as loop regions or bulge regions having unpaired bases).

In any embodiment herein, the method includes administering an effective amount of a nuclease, or a nucleic acid sequence encoding the nuclease. In particular embodiments, the nuclease is configured to interact with the synthetic guiding component and to bind and/or cleave the enriched single-stranded target sequence.

In any embodiment herein, the method includes modulating a target (e.g., increasing or decreasing the amount of a target, as compared to a control in which the synthetic guiding construct is not provided to the subject). Such modulating can include modulating RNA processing (e.g., modulating the activity of RNA polymerase), modulating viral replication (e.g., cleaving viral RNA), modulating gene expression by cleaving mRNA, interfering with protein binding to RNA, modulating splicing or RNA, modulating RNA transport, modulating localization of RNA, modulating translation of RNA, modulating turnover of mRNA, and modulating RNA folding.

In any embodiment herein, the single-stranded target sequence is a single-stranded RNA (e.g., a coding RNA or a non-coding RNA, such as any described herein).

In any embodiment herein, the effective amount of the synthetic guiding component is an amount sufficient to reduce expression of the target (e.g., in which the target is a gene product, such as a protein). In particular embodiments, the synthetic guiding component is configured to bind to the single-stranded target sequence that directly regulates the expression of the target (e.g., by cleaving the mRNA that encodes the target). In other embodiments, the synthetic guiding component is configured to bind to the single-stranded target sequence that indirectly regulates the expression of the target (e.g., by interfering with protein binding to RNA, which in turn interferes with expression of the target).

In any embodiment herein, the effective amount of the synthetic guiding component is an amount sufficient to increase expression of the target (e.g., in which the target is a gene product, such as a protein).

In any embodiment herein, the single-stranded target sequence is a single-stranded ribonucleic acid sequence (e.g., a portion of a sequence that is single-stranded or an entire sequence that is single-stranded). Exemplary single-stranded RNA sequences can include coding RNA or non-coding RNA, e.g., messenger RNA (mRNA, including elements thereof, such as a riboswitch, an untranslated region, a coding sequence, a start codon, a 5' cap, or a poly-adenine tail), transfer-messenger RNA (tmRNA), ribosomal RNA (rRNA, such as the 30S, 40S, 50S, 60S, 80S, 5S, 5.8S, 12S, 16S, 18S, 23S, and 28S subunits), ribozyme, transfer RNA (tRNA), heterogeneous nuclear RNA (hnRNA), circular RNA, signal recognition particle RNA (SRP RNA, such as 4.5S, 6S, 7SL, or ffs RNA), X-inactive specific transcript (Xist), microRNA (miRNA), small interfering RNA (siRNA), piwi-interacting RNA (piRNA), small nucleolar RNA (snoRNA, such as small Cajal body-specific RNA (scaRNA)), small nuclear RNA (snRNA), extracellular RNA (exRNA), long non-coding RNA (lncRNA), large intergenic non-coding RNA (lincRNA), intergenic RNA, enhancer RNA (eRNA), satellite RNA (satRNA), and promoter-associated RNA (PAR).

In any embodiment herein, the nuclease is a Cas protein or a modified form thereof. In some embodiments, the nuclease includes an amino acid sequence having at least 80% sequence identity (e.g., 85%, 90%, 95%, 96%, 97%, 98%, 99%, or 100% sequence identity) to any one of SEQ ID NOs:100, 101, 104, and 110-121, or a fragment thereof (e.g., a fragment having of from about 500 to 1800 amino acids, such as of from about 500 to 1700, 500 to 1600, 500 to 1500, 500 to 1400, 500 to 1300, 500 to 1200, 500 to 1100, 500 to 1000, 500 to 950, 500 to 900, 600 to 1800, 600 to 1700, 600 to 1600, 600 to 1500, 600 to 1400, 600 to 1300, 600 to 1200, 600 to 1100, 600 to 1000, 600 to 950, 600 to 900, 700 to 1800, 700 to 1700, 700 to 1600, 700 to 1500, 700 to 1400, 700 to 1300, 700 to 1200, 700 to 1100, 700 to 1000, 700 to 950, 700 to 900, 800 to 1800, 800 to 1700, 800 to 1600, 800 to 1500, 800 to 1400, 800 to 1300, 800 to 1200, 800 to 1100, 800 to 1000, 800 to 950, 800 to 900, 900 to 1800, 900 to 1700, 900 to 1600, 900 to 1500, 900 to 1400, 900 to 1300, 900 to 1200, 900 to 1100, 900 to 1000, 900 to 950, 1000 to 1800, 1000 to 1700, 1000 to 1600, 1000 to 1500, 1000 to 1400, 1000 to 1300, 1000 to 1200, 1000 to 1100, 1100 to 1800, 1100 to 1700, 1100 to 1600, 1100 to 1500, 1100 to 1400, 1100 to 1300, 1100 to 1200, 1200 to 1800, 1200 to 1700, 1200 to 1600, 1200 to 1500, 1200 to 1400, 1200 to 1300, 1300 to 1800, 1300 to 1700, 1300 to 1600, 1300 to 1500, 1300 to 1400, 1400 to 1800, 1400 to 1700, 1400 to 1600, 1400 to 1500, 1500 to 1800, 1500 to 1700, 1500 to 1600, 1600 to 1800, 1600 to 1700, or 1700 to 1800 amino acids).

In any embodiment herein, the nuclease can be a fusion protein including a Cas9 domain and another domain (e.g., a polymerase (e.g., a RNA-dependent RNA polymerase), a riboswitch, a ribozyme, a transcriptional activator, a repressive transcriptional domain, or an epigenetic effector domain.

In any embodiment herein, the synthetic guiding component include a structure having the formula (I): W—X—Y-L-Z or salt thereof. In some embodiments, W has a length of from 0 to about 20 nucleotides (e.g., of from about 0 to 4, 0 to 5, 0 to 6, 0 to 7, 0 to 8, 0 to 9, 0 to 10, 0 to 15, 1 to 4, 1 to 5, 1 to 6, 1 to 7, 1 to 8, 1 to 9, 1 to 10, 1 to 15, 1 to 20, 2 to 4, 2 to 5, 2 to 6, 2 to 7, 2 to 8, 2 to 9, 2 to 10, 2 to 15, 2 to 20, 3 to 4, 3 to 5, 3 to 6, 3 to 7, 3 to 8, 3 to 9, 3 to 10, 3 to 15, 3 to 20, 4 to 5, 4 to 6, 4 to 7, 4 to 8, 4 to 9, 4 to 10, 4 to 15, 4 to 20, 5 to 6, 5 to 7, 5 to 8, 5 to 9, 5 to 10, 5 to 15, 5 to 20, 10 to 15, 10 to 20, or 15 to 20 nucleotides, and optionally including one or more modified nucleotides, such as any described herein); X has a length of from about 10 to about 35 nucleotides (e.g., of from about 10 to 11, 10 to 12, 10 to 13, 10 to 14, 10 to 15, 10 to 17, 10 to 20, 10 to 25, 10 to 30, 12 to 13, 12 to 14, 12 to 15, 12 to 17, 12 to 20, 12 to 25, 12 to 30, 13 to 14, 13 to 15, 13 to 17, 13 to 20, 13 to 25, 13 to 30, 13 to 35, 14 to 15, 14 to 17, 14 to 20, 14 to 25, 14 to 30, 14 to 35, 15 to 17, 15 to 20, 15 to 25, 15 to 30, 15 to 25, 17 to 20, 17 to 25, 17 to 30, 17 to 35, 18 to 20, 18 to 25, 18 to 30, 18 to 35, 19 to 20, 19 to 25, 19 to 30, 19 to 35, 20 to 21, 20 to 22, 20 to 23, 20 to 24, 20 to 25, 20 to 26, 20 to 27, 20 to 28, 20 to 29, 20 to 30, 20 to 31, 20 to 32, 20 to 33, 20 to 34, 20 to 35, 21 to 22, 21 to 23, 21 to 24, 21 to 25, 21 to 26, 21 to 27, 21 to 28, 21 to 29, 21 to 30, 21 to 31, 21 to 32, 21 to 33, 21 to 34, 21 to 35, 22 to 23, 22 to 24, 22 to 25, 22 to 26, 22 to 27, 22 to 28, 22 to 29, 22 to 30, 22 to 31, 22 to 32, 22 to 33, 22 to 34, 22 to 35, 23 to 24, 23 to 25, 23 to 26, 23 to 27, 23 to 28, 23 to 29, 23 to 30, 23 to 31, 23 to 32, 23 to 33, 23 to 34, 23 to 35, 24 to 25, 24 to 26, 24 to 27, 24 to 28, 24 to 29, 24 to 30, 24 to 31, 24 to 32, 24 to 33, 24 to 34, 24 to 35, 25 to 26, 25 to 27, 25 to 28, 25 to 29, 25 to 30, 25 to 31, 25 to 32, 25 to 33, 25 to 34, 25 to 35, 26 to 27, 26 to 28, 26 to 29, 26 to 30, 26 to 31, 26 to 32, 26 to 33, 26 to 34, 26 to 35, 27 to 28, 27 to 29, 27 to 30, 27 to 31, 27 to 32, 27 to 33, 27 to 34, 27 to 35, 28 to 29, 28 to 30, 28 to 31, 28 to 32, 28 to 33, 28 to 34, 28 to 35, 29 to 30, 29 to 31, 29 to 32, 29 to 33, 29 to 34, 29 to 35, 30 to 31, 30 to 32, 30 to 33, 30 to 34, 30 to 35, 31 to 32, 31 to 33, 31 to 34, 31 to 35, 32 to 33, 32 to 34, 32 to 35, 33 to 34, 33 to 35, or 34 to 35 nucleotides, and optionally including one or more base pair mismatches upon binding to the target site); Y has a length of from about 10 to about 50 nucleotides (e.g., of from about 10 to 20, 10 to 25, 10 to 30, 10 to 35, 10 to 40, 10 to 45, 15 to 20, 15 to 25, 15 to 30, 15 to 35, 15 to 40, 15 to 45, 15 to 50, 20 to 25, 20 to 30, 20 to 35, 20 to 40, 20 to 45, 20 to 50, 25 to 30, 25 to 35, 25 to 40, 25 to 45, 25 to 50, 30 to 35, 30 to 40, 30 to 45, 30 to 50, 35 to 40, 35 to 45, 35 to 50, 40 to 45, 40 to 50, or 45 to 50 nucleotides, and optionally including one or more modified nucleotides, such as any described herein); L has a length of from 0 to about 15 nucleotides (e.g., L is a bond, an $C_{1-10}$ alkylene, a $C_{1-10}$ heteroalkylene, or has a length of from about 0 to 10 nucleotides, such as 0 to 2, 0 to 4, 0 to 6, 0 to 8, 0 to 10, 0 to 15, 2 to 4, 2 to 6, 2 to 8, 2 to 10, 2 to 15, 4 to 6, 4 to 8, 4 to 10, 4 to 15, 6 to 8, 6 to 10, 6 to 15, 8 to 10, 8 to 15, 10 to 15, or 13 to 15 nucleotides); and/or Z has a length of from about 10 to about 100 nucleotides (e.g., of from about 10 to 20, 10 to 30, 10 to 40, 10 to 50, 10 to 60, 10 to 70, 10 to 80, 10 to 90, 20 to 30, 20 to 40, 20 to 50, 20 to 60, 20 to 70, 20 to 80, 20 to 90, 20 to 100, 30 to 40, 30 to 50, 30 to 60, 30 to 70, 30 to 80, 30 to 90, 30 to 100, 40 to 50, 40 to 60, 40 to 70, 40 to 80, 40 to 90, 40 to 100, 50 to 60, 50 to 70, 50 to 80, 50 to 90, 50 to 100, 60 to 70, 60 to 80, 60 to 90, 60 to 100, 70 to 80, 70 to 90, 70 to 100, 80 to 90, 80 to 100, or 90 to 100 nucleotides).

In any embodiment herein, the synthetic guiding construct has a length of from about 80 to about 300 nucleotides (e.g., of from about 80 to 90, 80 to 100, 80 to 125, 80 to 150, 80 to 175, 80 to 200, 80 to 225, 80 to 250, 80 to 275, 90 to 100, 90 to 125, 90 to 150, 90 to 175, 90 to 200, 90 to 225, 90 to 250, 90 to 275, 90 to 300, 100 to 125, 100 to 150, 100 to 175, 100 to 200, 100 to 225, 100 to 250, 100 to 275, 100 to 300, 125 to 150, 125 to 175, 125 to 200, 125 to 225, 125 to 250, 125 to 275, 125 to 300, 150 to 175, 150 to 200, 150 to 225, 150 to 250, 150 to 275, 150 to 300, 175 to 200, 175 to 225, 175 to 250, 175 to 275, 175 to 300, 200 to 225, 200 to 250, 200 to 275, 200 to 300, 250 to 275, 250 to 300, or 275 to 300 nucleotides).

In any embodiment herein, the synthetic guiding construct does not include a protospacer-adjacent motif sequence.

In any embodiment herein, the synthetic guiding construct and/or the nuclease can be provided as a vector (e.g., as a vector including a sequence that encodes the synthetic guiding construct and/or the nuclease).

Definitions

As used herein, the term "about" means+/−10% of any recited value. As used herein, this term modifies any recited value, range of values, or endpoints of one or more ranges.

The term "effective" is used herein, unless otherwise indicated, to describe an amount of a compound, composition or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "compound" or "construct" is used herein to describe any specific compound or bioactive agent disclosed herein, including any and all stereoisomers (including diastereomers), individual optical isomers (enantiomers) or racemic mixtures, pharmaceutically acceptable salts (including alternative pharmaceutically acceptable salts when a pharmaceutically acceptable salt is disclosed) and prodrug forms. The term compound herein refers to stable compounds. Within its use in context, the term compound may refer to a single compound or a mixture of compounds as otherwise described herein.

By "salt" is meant an ionic form of a compound or structure (e.g., any formulas, compounds, constructs, or compositions described herein), which includes a cation or anion compound to form an electrically neutral compound or structure. Salts are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine. Exemplary salts include pharmaceutically acceptable salts.

By "pharmaceutically acceptable salt" is meant a salt that is, within the scope of sound medical judgment, suitable for use in contact with the tissues of humans and animals without undue toxicity, irritation, allergic response and the like and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspensing or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

By "isomer" is meant a molecule having the same molecular formula as the reference molecule. Exemplary isomers include stereoisomers, diastereomers, enantiomers, geometric isomers, tautomers, as well as mixtures thereof.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is a repressor of a gene, an effective amount of an agent is, for example, an amount sufficient to achieve a reduction in that gene's expression, as compared to the response obtained without administration of the agent.

By "subject" is meant a human, a non-human animal (e.g., a mammal), a host (e.g., a subject exposed to a pathogen, such as a human host exposed to a pathogen), a plant, a bacterium, or a pathogen (e.g., a virus, a phage, a bacterium, or a fungus).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

In accordance with the present invention there may be employed conventional molecular biology, microbiology, and recombinant DNA techniques within the skill of the art. Such techniques are explained fully in the literature. See, e.g., Sambrook et al., 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. Any sequence with uracil may be substituted with thymine and vice versa.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, etc.), 2'-alkyl (e.g., 2'-methyl, 2'-ethyl, 2'-propyl, 2'-allyl, etc.), 2'-aryl (e.g., 2'-phenyl), 2'-alkaryl (e.g., 2'-benzyl), 2'-amino (e.g., 2'-NH$_2$, 2'-NR$^{N1}$R$^{N2}$, which each of R$^{N1}$ and R$^{N2}$ is, independently, H, alkyl, or alkaryl), 2'-alkoxy (e.g. 2'-O-methoxy, 2'-O-ethoxy, etc.), 2'-alkylamine (e.g., 2'-O-methylamine, 2'-O-ethylamine, etc.), 2'-O-alkylamine (e.g., 2'-O-methylamine, 2'-O-ethylamine, etc.), 2'-azido, 2'-O-cyanoalkyl (e.g., 2'-O-cyanomethyl), 2'-O-alkoxylalkyl (e.g., 2'-O-(2-methoxyethyl)), etc. A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800, or more nucleotides; or 10, 20, 30, 40, 50, 60, 70, 80, 90, 100, 150, 200, 250, 300, 350, 400, 450, 500, 550, 600, 640, or more amino acids. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamic acid and aspartic acid; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., J. Mol. Biol. 1981; 147:195-7) and BLAST (Basic Local Alignment Search Tool; Altschul S F et al., J. Mol. Biol. 1990; 215:403-10). These and other alignment algorithms are accessible using publicly available computer software such as "Best Fit" (Smith T F et al., Adv. Appl. Math. 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "target sequence" as used herein is a polynucleotide (e.g., as defined herein, including a DNA, RNA, or DNA/RNA hybrid, as well as modified forms thereof and single-stranded forms thereof) that includes a "target site." The term "target site" refers to a nucleic acid sequence present in a target genomic sequence (e.g., ssDNA or ssRNA in a host or pathogen) to which a targeting portion of the guiding component will bind provided sufficient conditions (e.g., sufficient complementarity) for binding exist. Suitable DNA/RNA binding conditions include physiological conditions normally present in a cell. Other suitable DNA/RNA binding conditions (e.g., conditions in a cell-free system) are known in the art; see, e.g., Sambrook, supra.

By "cleavage" it is meant the breakage of the covalent backbone of a target sequence (e.g., a nucleic acid molecule). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guiding component and a nuclease is used for targeted double-stranded DNA cleavage. In other embodiments, a complex comprising a guiding component and a nuclease is used for targeted single-stranded RNA cleavage.

"Nuclease" and "endonuclease" are used interchangeably herein to mean an enzyme which possesses catalytic activity for cleavage of a nucleic acid sequence.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

By "linker" is meant any useful multivalent (e.g., bivalent) component useful for joining to different portions or segments. Exemplary linkers include a bond (e.g., a covalent bond), a nucleic acid sequence, a chemical linker, etc. In one instance, the linker of the synthetic guiding component can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a synthetic guiding component is 4 nt.

A "vector" or "expression vector" is a replicon, such as plasmid, phage, virus, or cosmid, to which another nucleic acid segment, i.e., an "insert", may be attached so as to bring about the replication of the attached segment in a cell.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 7A-7D shows that SauCas9 prefers a complementary region of 23 nt for binding and cleavage. Diagram of pUC ssRNA target (SEQ ID NO:12) and regions of complementary for the different length sgRNAs (SEQ ID NOs:300-306) (FIG. 7A). Representative in vitro cleavage assays using sgRNAs with a complementary region to the target of the indicated lengths (FIG. 7B). Time points are 0, 1, 2, 5, 10, 30, 60, and 120 mins. T1 RNase digest size fragments are given on the left. Quantification of cleavage products (FIG. 7C) from reactions in FIG. 7B. Length of targeting region of the sgRNA given as n-mer. Fit was determined in Prism using a single-exponential decay model. Error bars represent the mean±S.D. (n=3). Filter binding data for dSauCas9 and the structured RNA substrates were fit in Prism using a one-site binding model (FIG. 7D) and the apparent dissociation constant ($K_{d,app}$) was determined. Bars represent the mean±S.D. (n=3).

FIG. 11A-11D shows that enriched guides do not display sequence bias and cluster to regions on the MS2 genome. Stacked bar graph of positively enriched guides (FDR-adjusted p-value <0.05) for perfectly complementary and single-nucleotide mismatch (SNP) guides for a multiplicities of infection (MOI) of 10 and 100 (FIG. 11A, left). Percentages of perfect and SNP guides by length averaged across the control libraries (n=3) (FIG. 11A, right). WebLogo (see, e.g., Crooks G E et al., *Genome Res.* 2004; 14(6):1188-90)

Figure 11C:
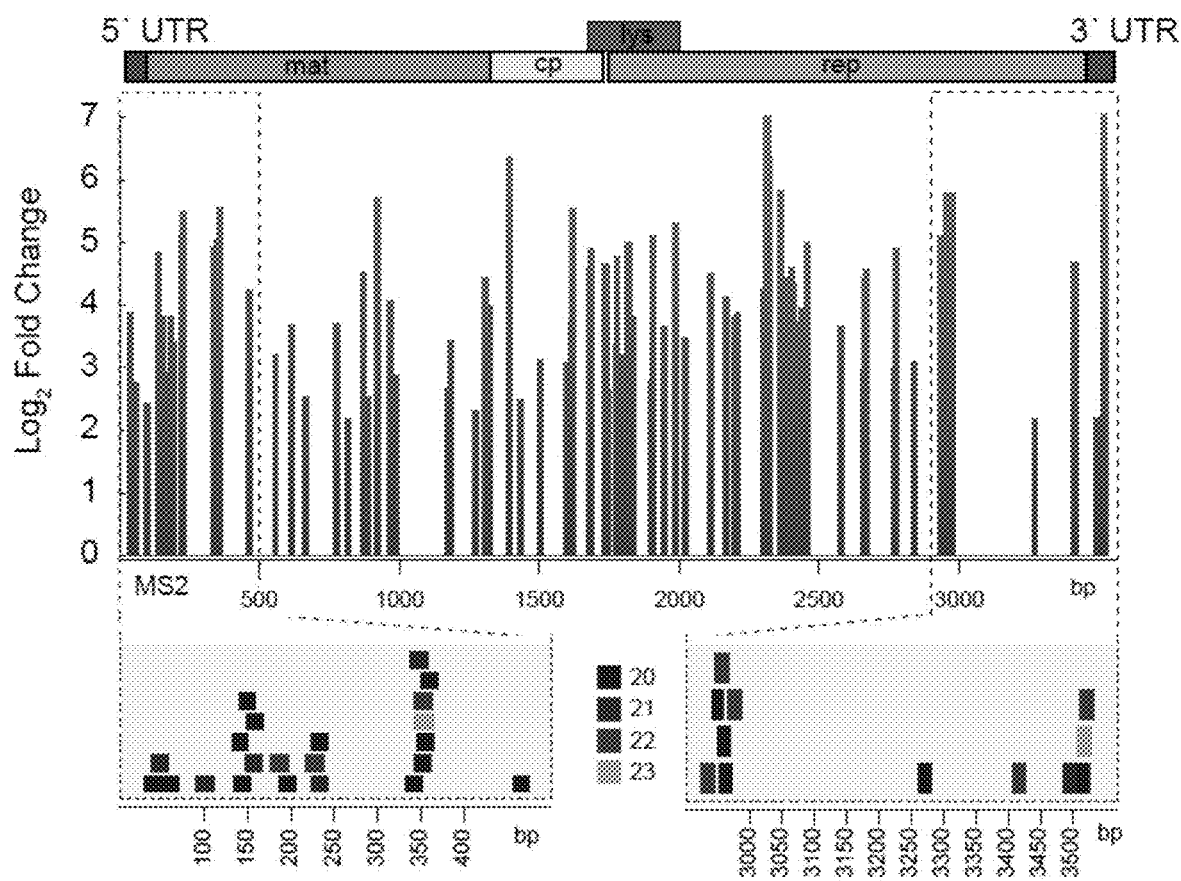
Figure 11D:
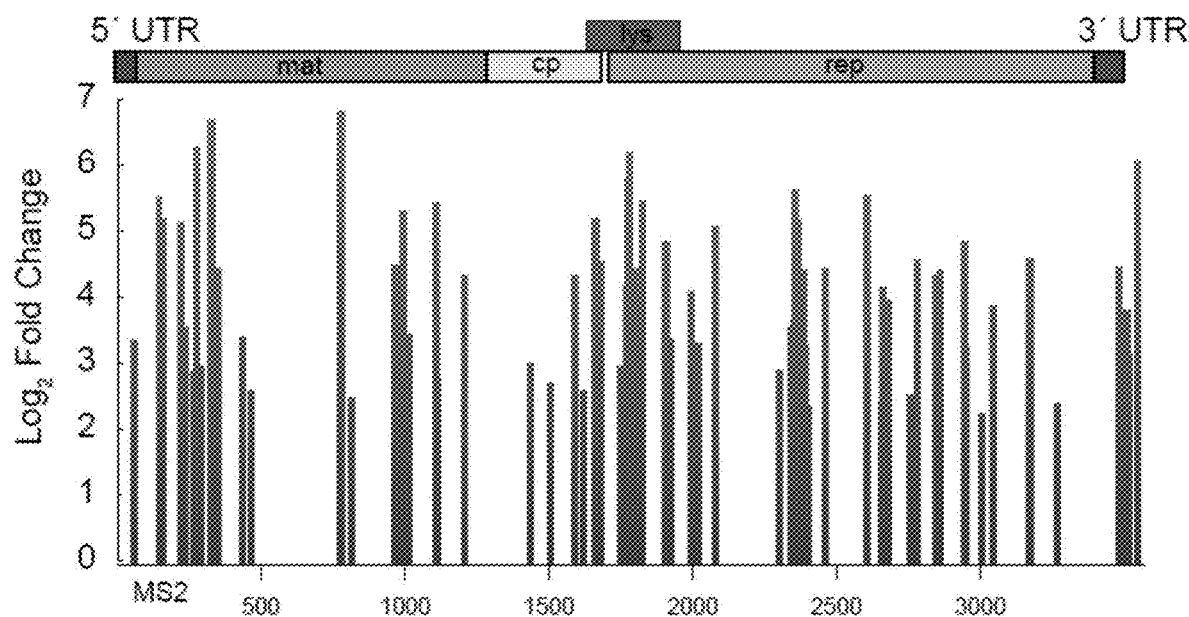

representation of positively enriched guides (perfect complementarity, FDR-adjusted p-value <0.05) for MOI-10 (n=84) and MOI-100 (n=107) (FIG. 11B). Different length guides were aligned at their 3' end, which contains the pre-ordered 'seed' region. $Log_2$ fold-change of positively enriched guides (FDR-adjusted p-value <0.05) mapped to the MS2 genome for MOI-100 treatment (FIG. 11C, upper). Schematic of MS2 genome is provided above. Individual guides mapped to highlighted regions of MS2 genome (FIG. 11C, lower). $Log_2$ fold-change of guides with an FDR-adjusted p-value <0.05 mapped to the MS2 genome for MOI-10 treatment (FIG. 11D).

Figure 12:
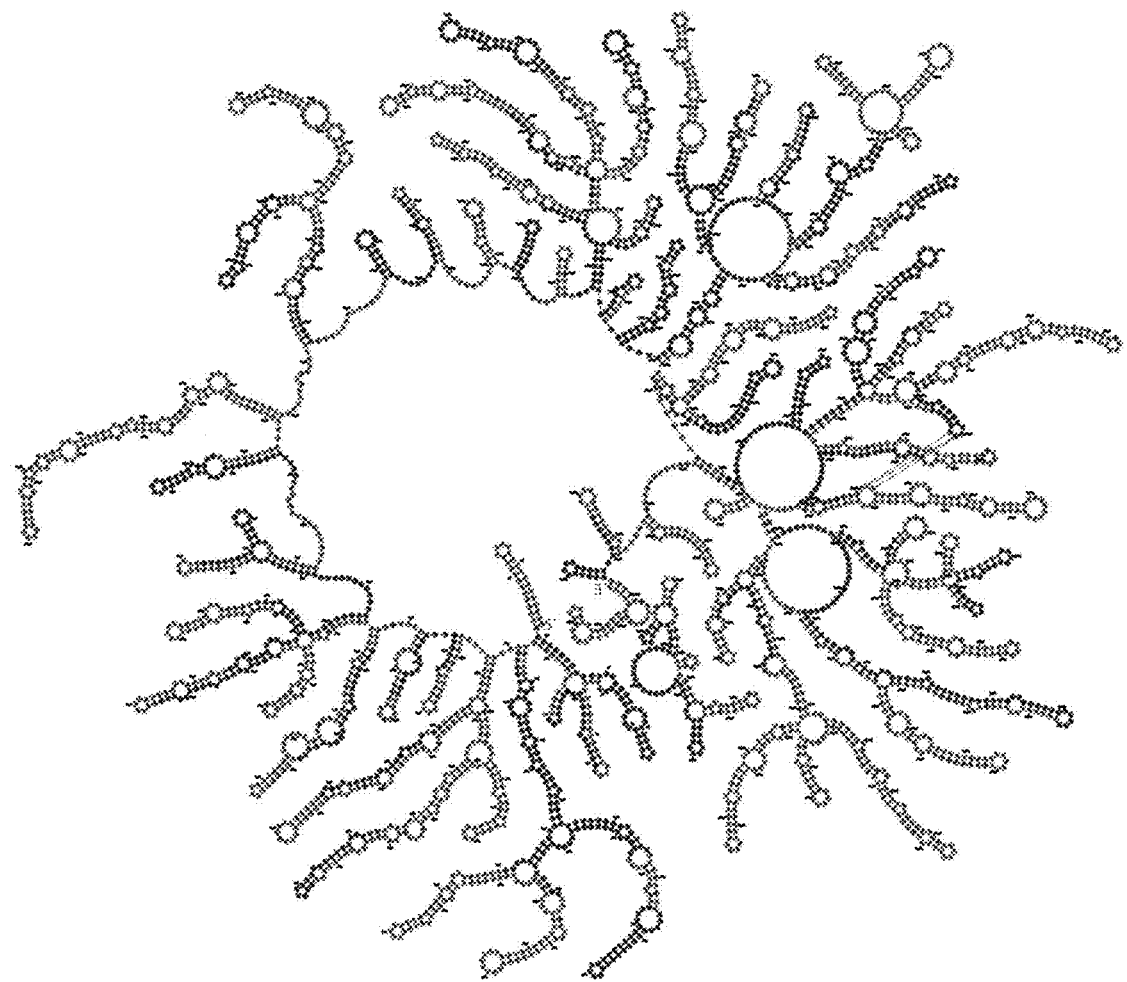

FIG. 12 shows enriched MS2 targeting guides mapped to MS2 genome structure. Structure of the MS2 genome inside the viral particle was obtained from a recently published EM structure (see, e.g., Dai X et al., *Nature* 2017; 541(7635): 112-6) and guides (red) significantly enriched in the MOI-100 treatment (FDR-adjusted p-value <0.05) were mapped to the MS2 genome and subsequently visualized in Forna (see, e.g., Kerpedjiev P et al., Bioinformatics 2015; 31(20): 3377-9).

Figure 13A:
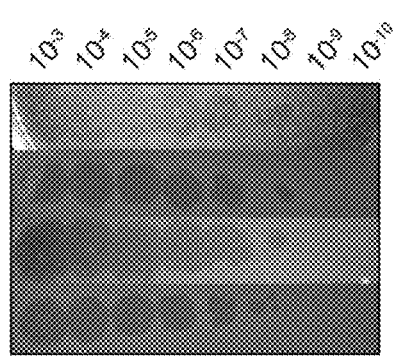
Figure 13B:
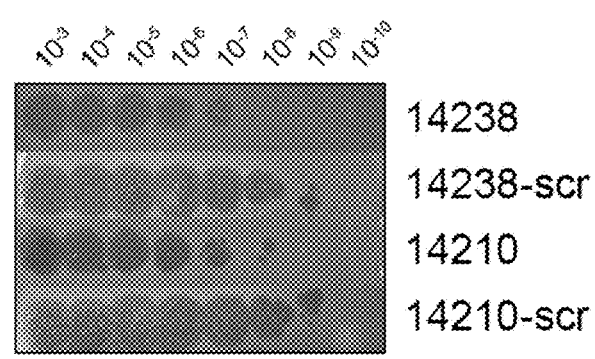
Figure 13C:
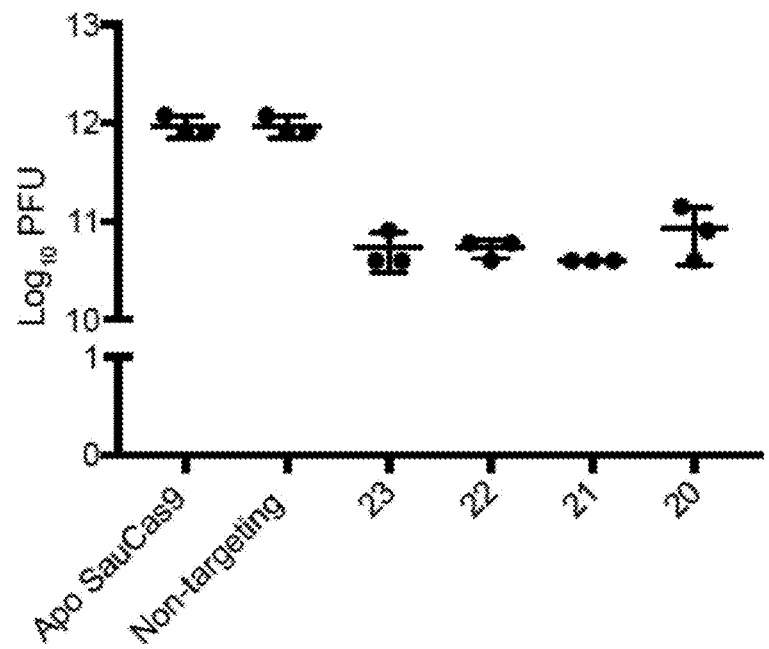
Figure 13D:
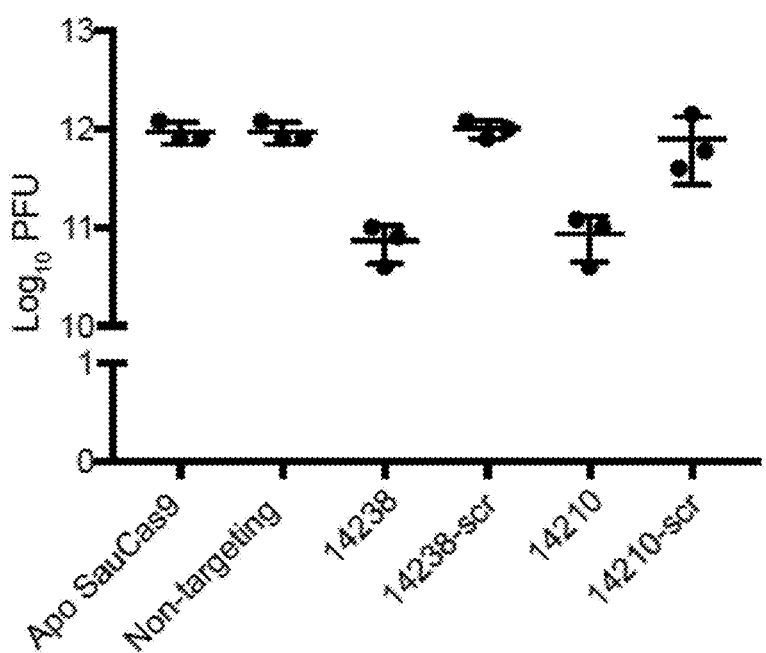
Figure 13E:
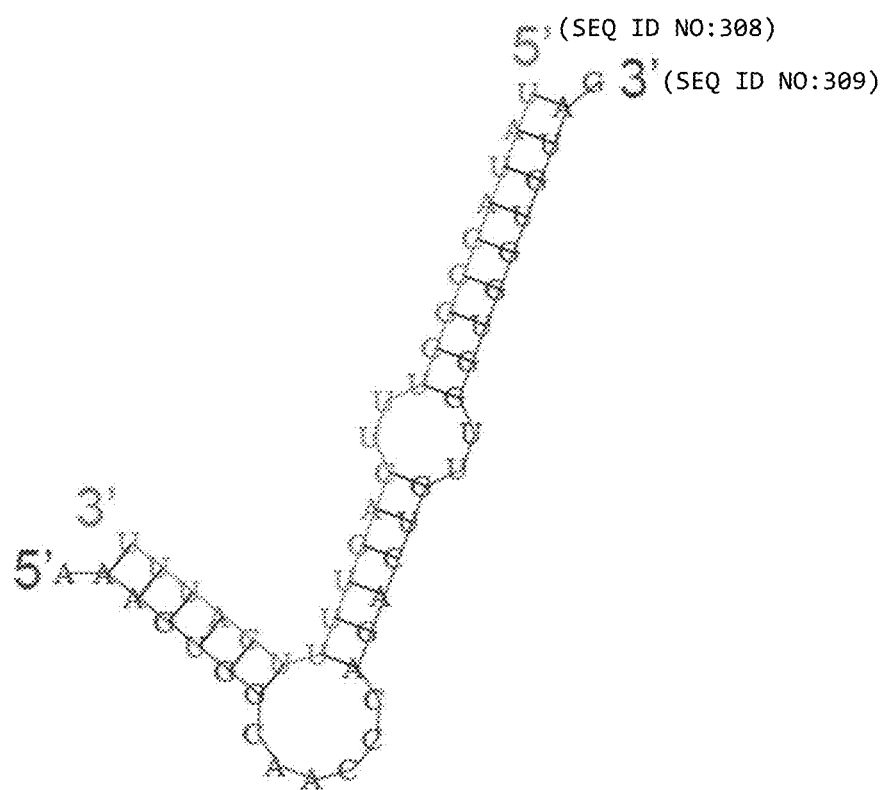

FIG. 13A-13E shows confirmation that enriched guides from the MS2 screen confer protection against MS2 infection. Representative plaque assay for lawns of *E. coli* expressing wtSauCas9 and sgRNA of different length spotted with phage dilutions indicated (FIG. 13A-13B). Here, the sgRNA with the highest fold-change in both MOI-10 and -100 samples was chosen for each length. The 23-mer sgRNA produces hazy plaques for an unknown reason. All other guides tested, including a different 23-mer sgRNA, produced clear plaques. In FIG. 13B, guides were two 'control' guides that were significantly enriched in both MOI-10 and MOI-100 treatments during phage selection. Scrambled (scr) indicates random shuffling of the target sequence to serve as a non-targeting control. Scrambled sequences were verified against the MS2 genome and its reverse-complement to ensure no partial matches. Quantification of relative PFUs (mean±S.D., n=3) (FIG. 13C-13D) from data in FIG. 13A-13B, respectively. In FIG. 13D, guides 14238 and 14210 confer ~10-fold protection over their scrambled counterparts. The level of protection was similar to perfectly complementary guides in FIG. 13C (see also FIG. 10E-10F). Predicted binding (FIG. 13E) of guide 14238 (green, SEQ ID NO:308) to a fragment of the MS2 genome (red, nts: 1533-1563, SEQ ID NO:309) using RNAhybrid (see, e.g., Rehmsmeier M et al., RNA 2004; 10(10):1507-17).

Figure 14A:
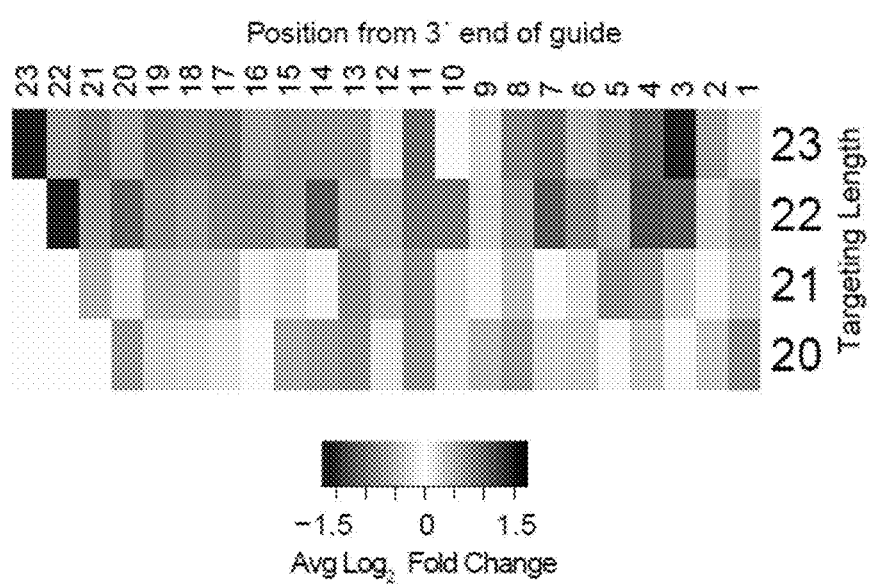
Figure 14B:
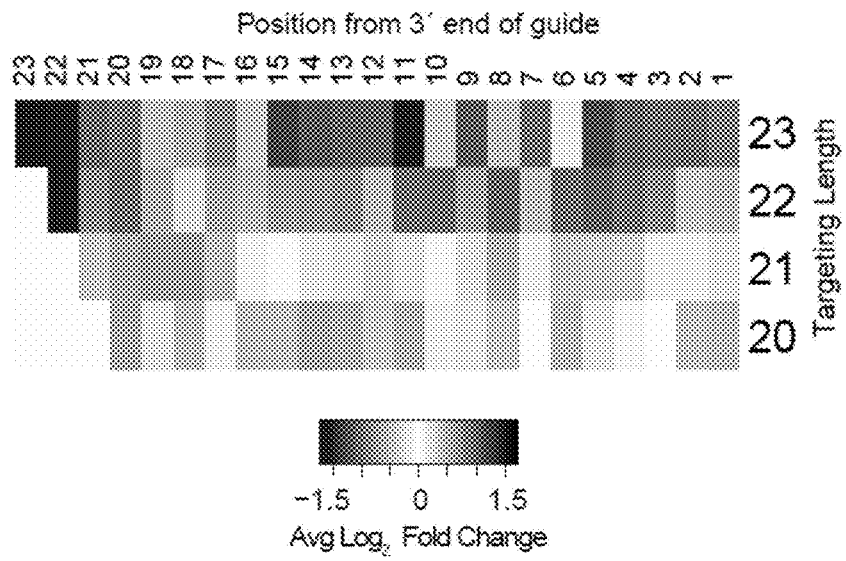
Figure 14C:
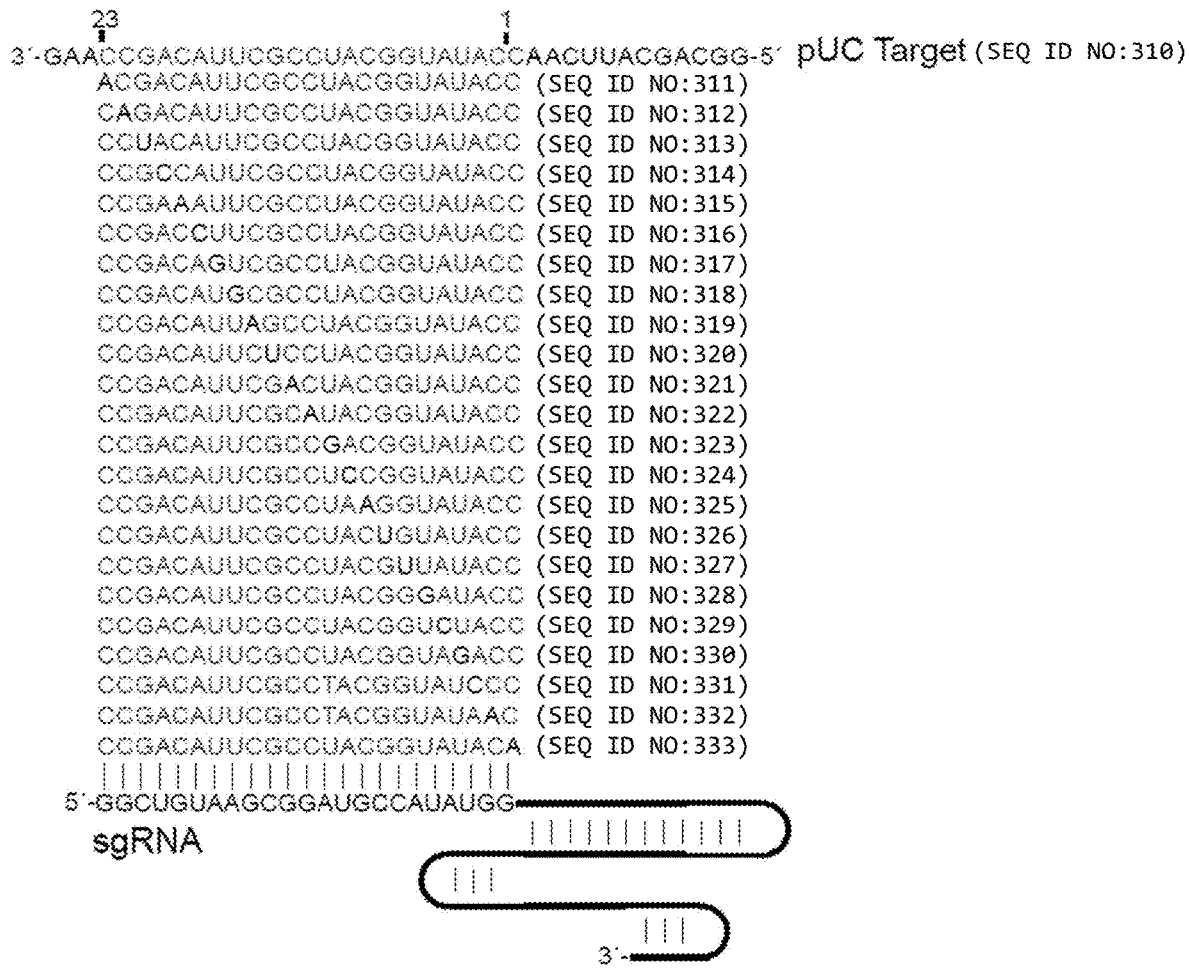

FIG. 14A-14D shows the effect of single-nucleotide mismatches on ssRNA targeting. Heatmap of average $log_2$ fold-change for all single-nucleotide mismatch (SNP) guides in MOI-10 (FIG. 14A) and MOI-100 (FIG. 14B) treatment. Deeper blue represents greater negative selection of guides indicating greater sensitivity to mismatches at that position, while deeper black represents greater positive selection indicating that mismatches at that position are more tolerated. Positions are given as distance from 3' end of the targeting region of the sgRNA. Diagram of target ssRNAs with SNPs (SEQ ID NO 2:311-333) for in vitro cleavage assays, as compared to the pUC target (SEQ ID NO:310) (FIG. 14C). Red highlights the region complementary to the guide while black nucleotides indicate the mismatched base in the targeting region. Numbering of nucleotides is labeled from 1 to 23 to reflect positions in FIG. 14A-14B. Quantification of in vitro cleavage assays (FIG. 14D) with mismatched targets in FIG. 14C. Bars represent the mean±S.D. (n=3). "Wt" indicates 23 nt of perfect complementarity between the sgRNA and the target.

Figure 15A:
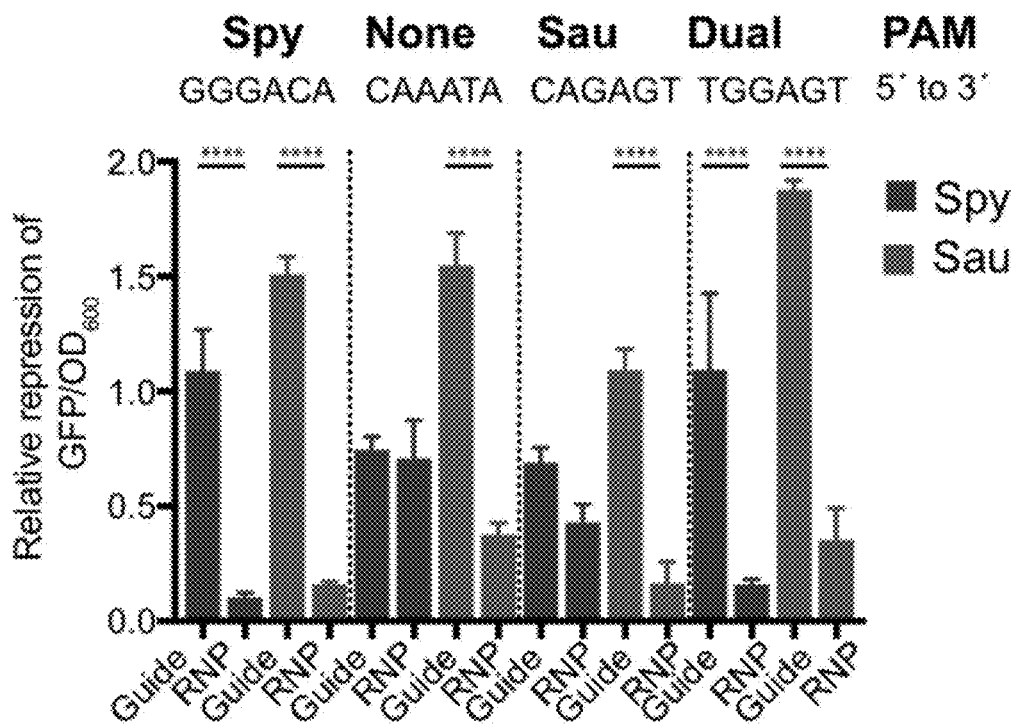
Figure 15D:
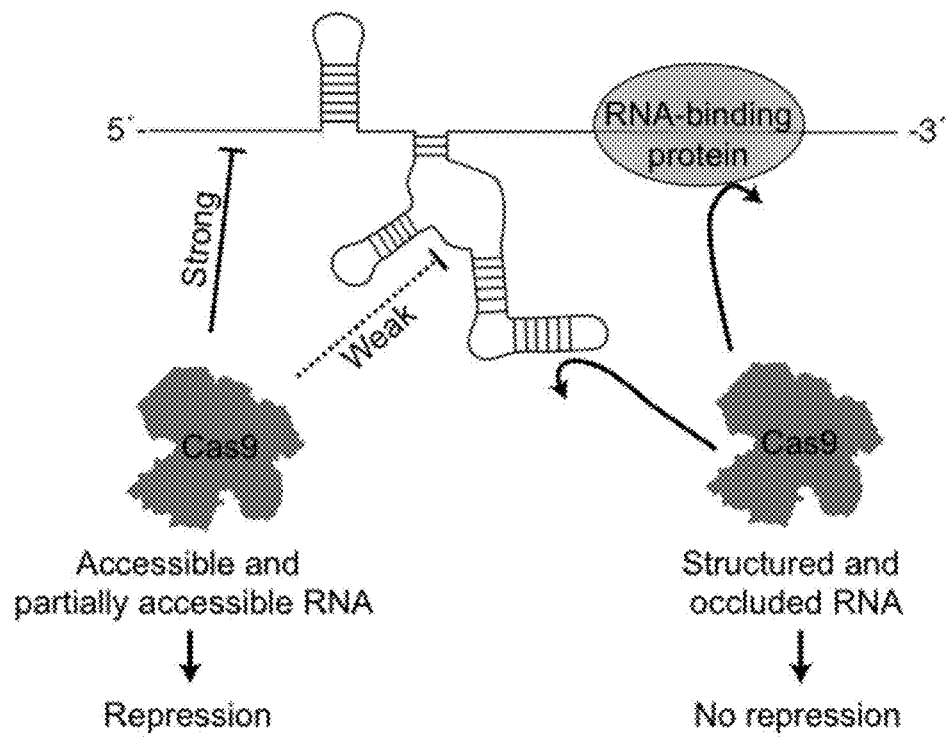

FIG. 15A-15D shows SauCas9 repression of a GFP reporter in vivo. Comparison of dSpyCas9 and dSauCas9 to repress GFP expression on the DNA and RNA level (FIG. 15A). GFP signal was normalized to $OD_{600}$ to control for difference in cell density between samples. $GFP/OD_{600}$ ratios for guide alone and RNP are normalized to values for a non-targeting guide vector and an Apo protein control, respectively. Target sites were chosen to be adjacent to PAM sites for Spy, Sau, both, or neither as indicated. Note: the slight GFP repression observed with dSpyCas9 using the target sequence adjacent to the Sau PAM (CAGAGT) likely results from the ability of SpyCas9 to use an NAG PAM, albeit with reduced efficiency (see, e.g., Hsu P D et al., Nat. Biotechnol. 2013; 31(9):827-32). ****p<0.0001 by one-way ANOVA. Relative expression of GFP using guides with different length targeting sequences (FIG. 15B). Target site here is the GFP2 sequence chosen for its robust targeting activity. Diagram of targeting sequences across the GFP mRNA and ribosome binding site (RBS) (FIG. 15C, upper). Relative expression of GFP of SauCas9 RNP normalized to sgRNA alone for targeting sequences across the GFP reporter (FIG. 15C, lower). Dashed red line indicates that the sgRNA alone is as efficient as the RNP for GFP repression. Bars in FIG. 15A-15C represent mean±S.D. (n=3). Non-limiting model for observed SauCas9 ssRNA targeting activity (FIG. 15D). We propose that accessible RNA is cleaved or repressed efficiently while structured and protein-bound RNA is not targeted by SauCas9.

Figure 16A:
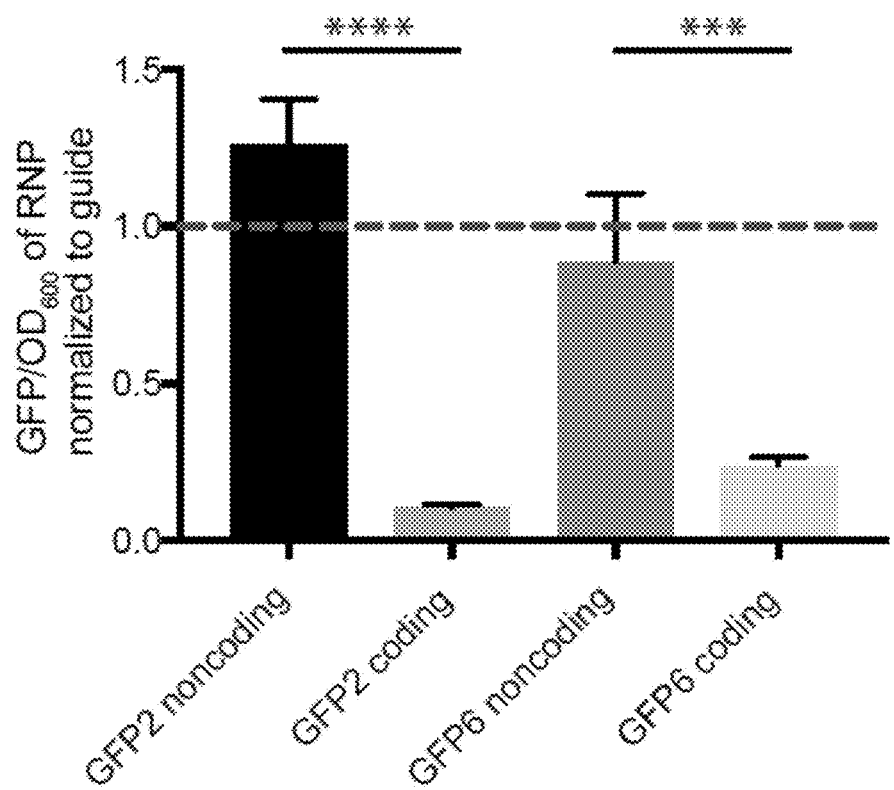
Figure 16B:
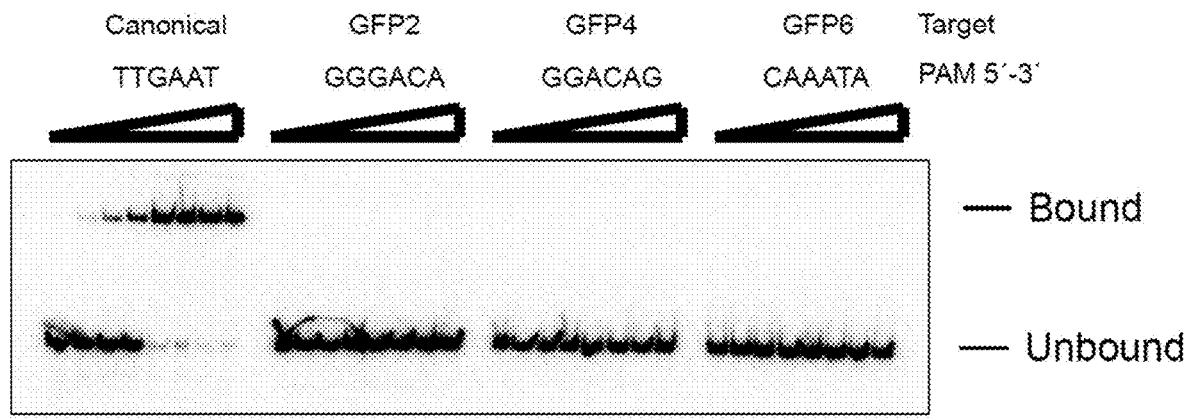
Figure 16C:
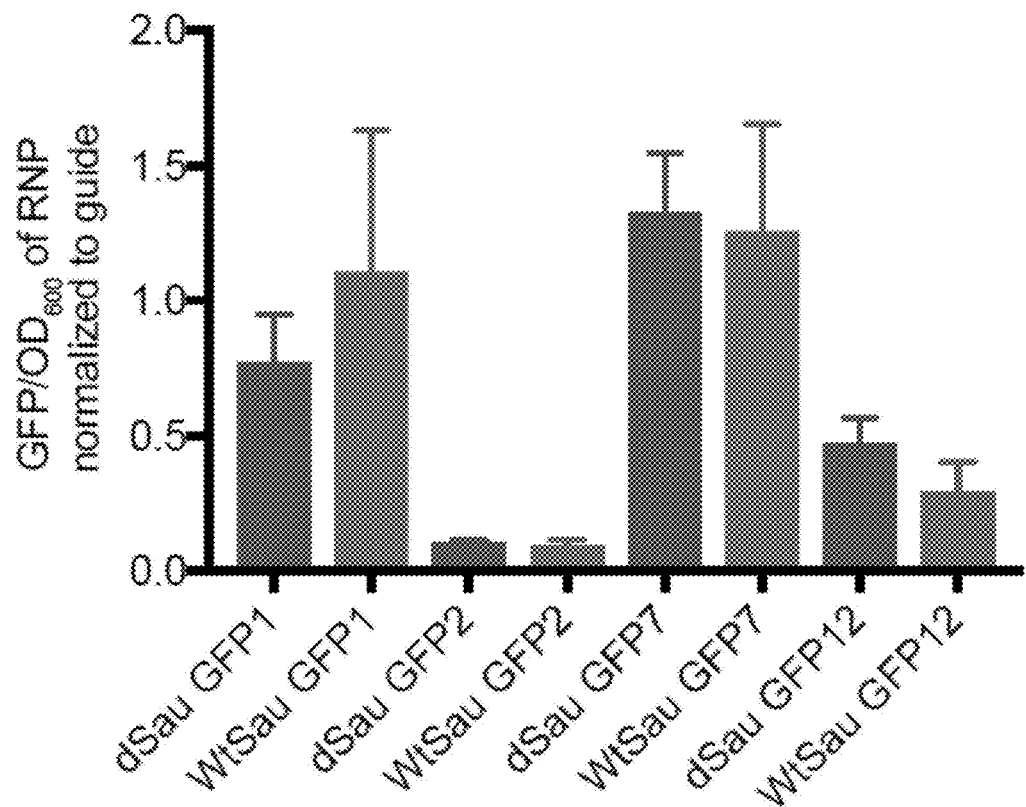

FIG. 16A-16C shows repression of GFP mRNA. dSauCas9-sgRNA directed against a GFP mRNA (coding) or antisense (noncoding) sequence (FIG. 16A). GFP2 and GFP6 refer to guides diagrammed in FIG. 15C. Dashed red line indicates that the sgRNA alone is as efficient as the SauCas9 RNP for GFP repression. Bars represent mean±S.D. (n=3). *p<0.001, **p<0.0001, by one-way ANOVA. Electrophoretic mobility shift assay (EMSA) confirming that dSauCas9 does not bind dsDNA adjacent to non-canonical PAMs (FIG. 16B). Targeting sequence was identical for all substrates but with varied PAM sequences as indicated for the guides in FIG. 15C. Final concentrations of dSauCas9 from left to right: 0, 0.1, 0.5, 1, 5, 10, 50, 100 nM. Comparison of ability of dSau and wtSauCas9 to repress GFP expression in vivo (FIG. 16C). Bars represent mean±S.D. (n=3).

FIG. 17A-17E shows exemplary protein sequences for Cas9 proteins (from the N to C terminus). Provided are protein sequences for wild-type *Staphylococcus aureus* Cas9 (SauCas, SEQ ID NO:100) (FIG. 17A), dSauCas9 (D10A and N580A, SEQ ID NO:101) (FIG. 17B), *Streptococcus pyogenes* Cas9 (SpyCas, SEQ ID NO:102) (FIG. 17C), *Francisella novicida* Cas9 (FnoCas9, SEQ ID NO:103) (FIG. 17D), and *Campylobacter jejuni* Cas9 (CjeCas9, SEQ ID NO:104) (FIG. 17E). Further protein sequences can include one or more of SEQ ID NOs:100-104, or a fragment thereof, having one or more conservative amino acid substitutions, as defined herein; and one or more sequences that is substantially identical (e.g., having at least about 80%, 85%, 90%, 95%, 96%, 97%, 98%, 99%, or 100% sequence identity) to one or more of SEQ ID NOs:100-104 or a fragment thereof (e.g., a fragment having of from about 500 to 1500 amino acids, e.g., 500 to 1400, 500 to 1300, 500 to 1200, 500 to 1100, 500 to 1000, 500 to 950, 500 to 900, etc.).

FIG. 18A-18E shows exemplary single-guide RNA (sgRNA) constructs (from 5' to 3' end) employed in the Examples described herein. Provided are in vitro sgRNA constructs (SEQ ID NOs:1-11) (FIG. 18A), in vitro target sequences (SEQ ID NOs:12-39) (FIG. 18B), sgRNA constructs for MS2 plaque assays (SEQ ID NOs:40-52) (FIG. 18C), sgRNA constructs for GFP reporter expression assays (SEQ ID NOs:53-71) (FIG. 18D), and GFP repression targets (SEQ ID NOs:72-76) (FIG. 18E). Further nucleic acid sequences can include one or more sequences that is substantially identical (e.g., having at least about 80%, 85%, 90%, 95%, 96%, 97%, 98%, 99%, or 100% sequence identity) to one or more of SEQ ID NOs:1-76 or a fragment thereof.

FIG. 19A-19L shows further exemplary protein sequences for Cas9 proteins (from the N to C terminus). Provided are protein sequences for *Staphylococcus aureus* Cas9 (UniProtKB J7RUA5, SEQ ID NO:110) (FIG. 19A), *Campylobacter jejuni* subsp. *jejuni* serotype 0:2 Cas9 (UniProtKB Q0P897, SEQ ID NO:111) (FIG. 19B), *Streptococcus thermophilus* Cas9 (UniProtKB G3ECR1, SEQ ID NO:112) (FIG. 19C), *Streptococcus thermophilus* (strain ATCC BAA-491/LMD-9) Cas9-1 (UniProtKB Q03LF7, SEQ ID NO:113) (FIG. 19D), *Streptococcus thermophilus* (strain ATCC BAA-491/LMD-9) Cas9-2 (UniProtKB Q03JI6, SEQ ID NO:114) (FIG. 19E), *Wolinella succinogenes* Cas9 (UniProtKB Q7MRD3, SEQ ID NO:115) (FIG. 19F), *Wolinella succinogenes* Cas9/Csx12 (NCBI WP_011139431.1, SEQ ID NO:116) (FIG. 19G), *Staphylococcus lugdunensis* Cas9 (UniProtKB A0A133QCR3, SEQ ID NO:117) (FIG. 1911), *Staphylococcus pseudintermedius* ED99 Cas9 (GenBank ADX75954.1, SEQ ID NO:118) (FIG. 19I), *Helicobacter mustelae* Cas9 (UniProtKB D3UFL8, SEQ ID NO:119) (FIG. 19J), *Streptococcus pasteurianus* Cas9 (UniProtKB A0A135YMA6, SEQ ID NO:120) (FIG. 19K), and *Streptococcus pasteurianus* (strain ATCC 43144/JCM 5346/CDC 1723-81) Cas9 (UniProtKB F5X275, SEQ ID NO:121) (FIG. 19L). Further protein sequences can include one or more of SEQ ID NOs:110-121, or a fragment thereof, having one or more conservative amino acid substitutions, as defined herein; and one or more sequences that is substantially identical (e.g., having at least about 80%, 85%, 90%, 95%, 96%, 97%, 98%, 99%, or 100% sequence identity) to one or more of SEQ ID NOs: 110-121 or a fragment thereof (e.g., a fragment having of from about 500 to 1500 amino acids, e.g., 500 to 1400, 500 to 1300, 500 to 1200, 500 to 1100, 500 to 1000, 500 to 950, 500 to 900, etc.).

FIG. 20A-20J shows non-limiting synthetic guiding components. Provided are a schematic (FIG. 20A) of an exemplary synthetic guiding component 2000 (SEQ ID NO:5) including a first portion 2001 (e.g., a crRNA sequence, such as any described herein), a second portion 2002 (e.g., a tracrRNA sequence, such as any described herein), a target portion 2004, and a linker 2005 and a schematic (FIG. 20B) of the exemplary synthetic guiding component 2000 (SEQ ID NO:5) bound to a target site 2011 of an exemplary target sequence 2012 (SEQ ID NO:12). Also provided are non-limiting nucleic acid sequences (FIG. 20C-20J) that can be employed as a first portion, a linker, and/or a second portion (SEQ ID NOs:150-273). In one non-limiting instance, the synthetic guiding component has a structure provided by formula 5'-W—X—Y-L-Z-3', in which W is a third portion, X is a targeting portion, Y is a first portion, L is a linker, and Z is a second portion, as described herein. In each instance, U can be substituted by T, and vice versa. Further nucleic acid sequences can include one or more sequences that is substantially identical (e.g., having at least about 80%, 85%, 90%, 95%, 96%, 97%, 98%, 99%, or 100% sequence identity) to one or more of SEQ ID NOs:150-273 or a fragment thereof.

FIG. 21 shows further non-limiting synthetic guiding components, in which W is a third portion and X is a targeting portion, as described herein (SEQ ID NOs:274-293). Further nucleic acid sequences can include one or more sequences that is substantially identical (e.g., having at least about 80%, 85%, 90%, 95%, 96%, 97%, 98%, 99%, or 100% sequence identity) to one or more of SEQ ID NOs: 274-293 or a fragment thereof.

DETAILED DESCRIPTION OF THE INVENTION

The present invention relates, in part, to a CRISPR-Cas based system for processing targets including single-stranded nucleic acid sequences. In particular embodiments, described herein are synthetic guiding components for binding and/or cleaving sequences include RNA or modified forms thereof. Such guiding components can be employed in conjunction with a nuclease (e.g., Cas9) that cleaves RNA sequences.

Figure 1A:
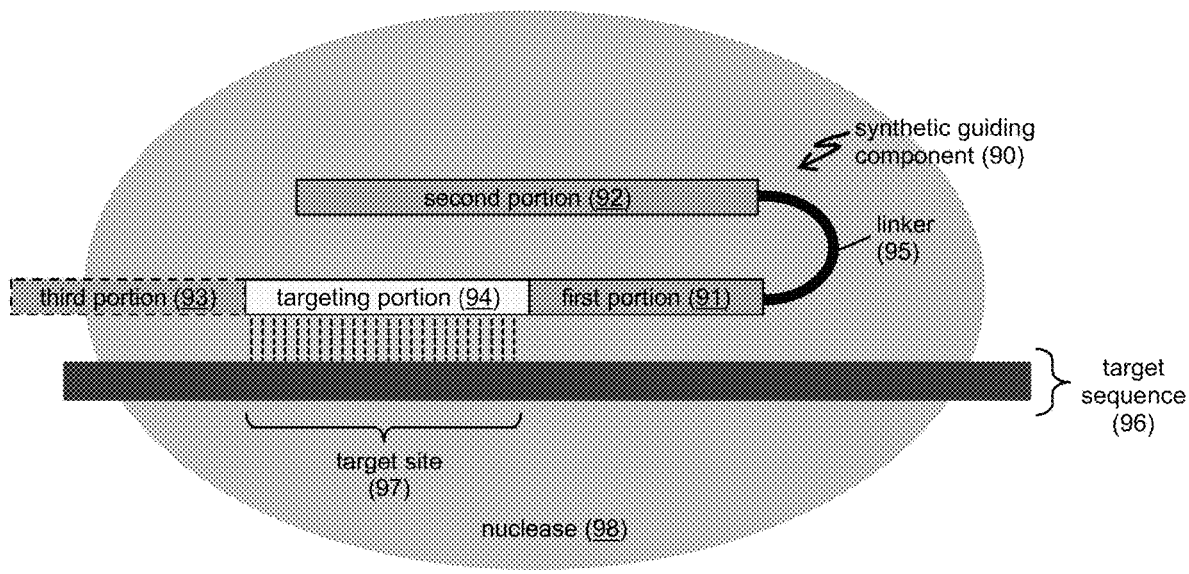
FIG. 1A-1B shows exemplary CRISPR-CAS based systems for targeting a target sequence. Provided are a schematic of an exemplary complex including a synthetic guiding component 90 and a nuclease 98, in which the complex in turn is bound to the target site 97 of the target sequence 96 (FIG. 1A); and a schematic of another exemplary complex including a synthetic guiding component and a Cas enzyme, in which the complex in turn is bound to a single-stranded (ss) target sequence (FIG. 1B).

FIG. 1A provides an exemplary synthetic guiding component 90, which in turn includes a targeting portion 94, a first portion 91, a second portion 92, an optional third portion 93, and a linker 95. In general, the targeting portion 94 includes a nucleic acid sequence that is sufficiently complementary to a desired target site 97 of the target sequence 96. In this way, the guiding component can be programmed to bind to and interact with certain portions of a target sequence. The first and second portions 91,92 provide interactions sites with the nuclease 98 (e.g., a Cas9 nuclease), thereby providing the nuclease in proximity to the target site; and the linker 95 joins the first and second portions.

For a CRISPR-Cas based system, the first portion is typically derived from a crRNA (CRISPR RNA) sequence, and the second portion is typically derived from a tracrRNA (trans-activating crRNA) sequence. Such crRNA and tracrRNA sequences can be truncated or shortened as compared to wild-type sequences identified in bacteria and archaea, and then the truncated sequences can then be joined by way of a linker to form a synthetic guiding component. The linker can be a bond, an organic linker (e.g., an alkylene or heteroalkylene linker), or a nucleic acid sequence (e.g., any described herein). Exemplary sequences for first portions, second portions, and linkers are described herein.

Notably, the present invention relates, in part, to synthetic guiding components that lack a PAMmer sequence. While such a PAMmer sequence may be required for cleavage of DNA, we have identified conditions in which PAMmer sequences are not required for cleavage of RNA. Thus, in some non-limiting instances, the synthetic guiding components lack a PAMmer sequence.

In addition, we also describe conditions in which cleavage efficiency is impaired by duplex regions in the target RNA and in which cleavage efficiency is improved by the presence of mismatched segments that presents a more accessible substrate to ribonucleoprotein complex (e.g., a Cas9-synthetic guiding component complex). Thus, in some non-limiting instances, the guiding component includes one or more modifications that provides target-specificity while reducing substrate-RNP stability. Such modifications can include, e.g., one or more nucleic acid modifications in proximity to the targeting portion of the synthetic guiding component (e.g., one or more nucleic acid modifications in the third portion 93 of the guiding component, such as the 3' end of the third portion; and/or one or more nucleic acid modifications in the first portion 91 of the guiding component, such as the 5' end of the first portion).

Exemplary modifications include one or more modified nucleic acid to promote Cas9 access to the targeting site; or the presence of one or more bulges upon binding of the synthetic guiding component to the target site and/or the target sequence, such as by including one or more unpaired nucleotides in the first portion and/or third portion of the synthetic guiding component when the component is bound to the target sequence. Non-limiting modified nucleic acids include one or more backbone modifications (e.g., modifications to the 2' position of a nucleic acid, such as any described herein), use of bicyclic sugar analogs, one or more phosphate group modifications, one or more internucleoside linkage modifications (e.g., use of flexible alkane, glycol, or ether linkages between residues), and/or one or more sugar modifications (e.g., unlocked forms, such as GNA, TNA, PNA, etc.).

Figure 1B:
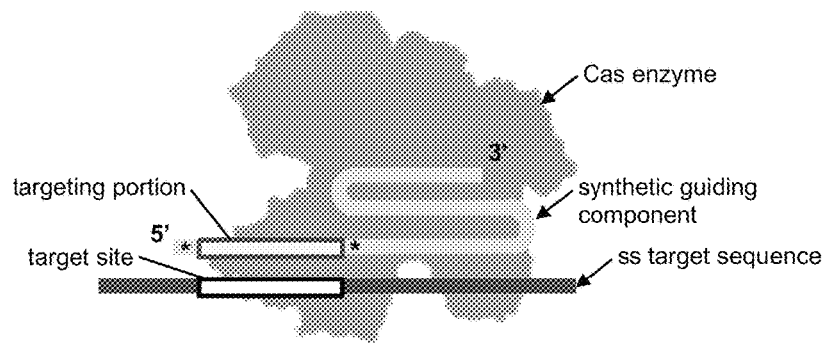

FIG. 1B provides another exemplary synthetic guiding component bound to a Cas enzyme. As can be seen, the targeting portion binds to the target site of the single-stranded (ss) target sequence. Various portions of the synthetic guiding component can have one or more modified nucleic acids. In one non-limiting instance, one or more modified nucleic acids are present in proximity to the 5'-end of the targeting portion and/or the 3'-end of the targeting portion (indicated by asterisks in FIG. 1B). In another non-limiting instance, one or more bulges are present in proximity to the 5'-end of the targeting portion and/or the 3'-end of the targeting portion (indicated by asterisks in FIG. 1B).

Synthetic Guiding Component

The synthetic guiding component can be a single-guide sequence. In particular embodiments, the sequence of the component can be encoded as a vector suitable for in vivo or in vitro expression.

Figure 2A:
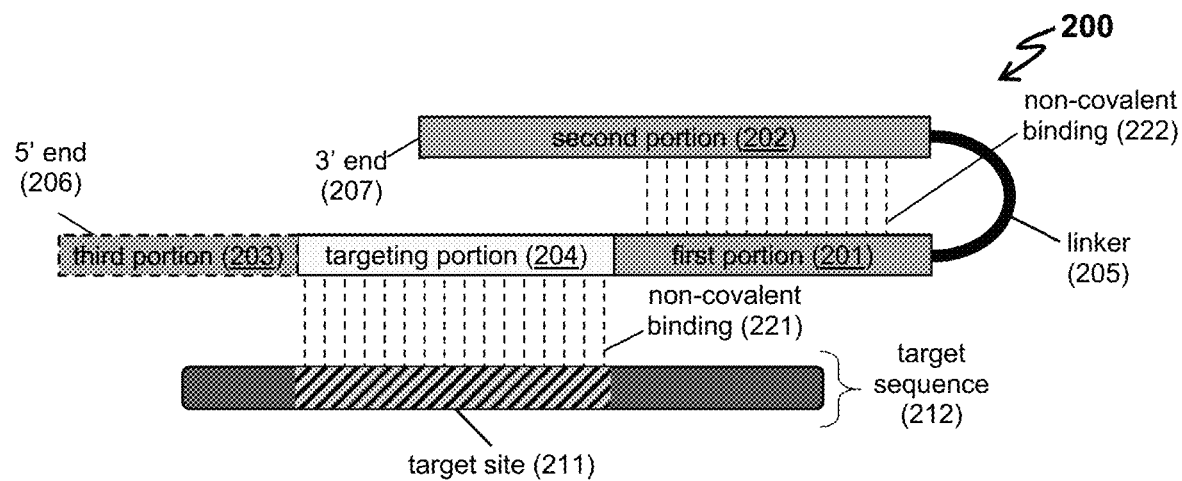
FIG. 2A-2C shows exemplary synthetic guiding components. Provided are a schematic of non-limiting interactions between the targeting portion 204 of the synthetic guiding component 200 with the target site 211 of the target sequence 21, as well as interactions between the first portion 201 and second portion 202 of the component 200 (FIG. 2A); a schematic of a non-limiting synthetic guiding component 300 having a targeting portion 304, a first portion 301, a second portion 302, an optional third portion 303, and a linker 305 disposed between the first and second portions (FIG. 2B); and a schematic of a non-limiting synthetic guiding component 350 having a targeting portion 354, a first portion 351, a second portion 352 having a hairpin, an optional third portion 353, and a linker 355 disposed between the first and second portions (FIG. 2C).
Figure 2B:
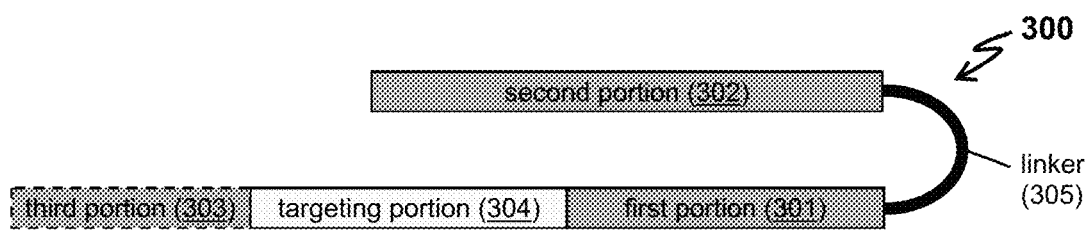
Figure 2C:
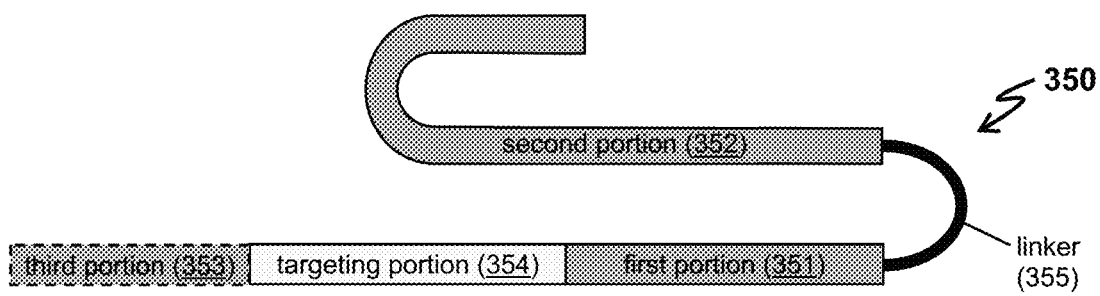
Figure 3A:
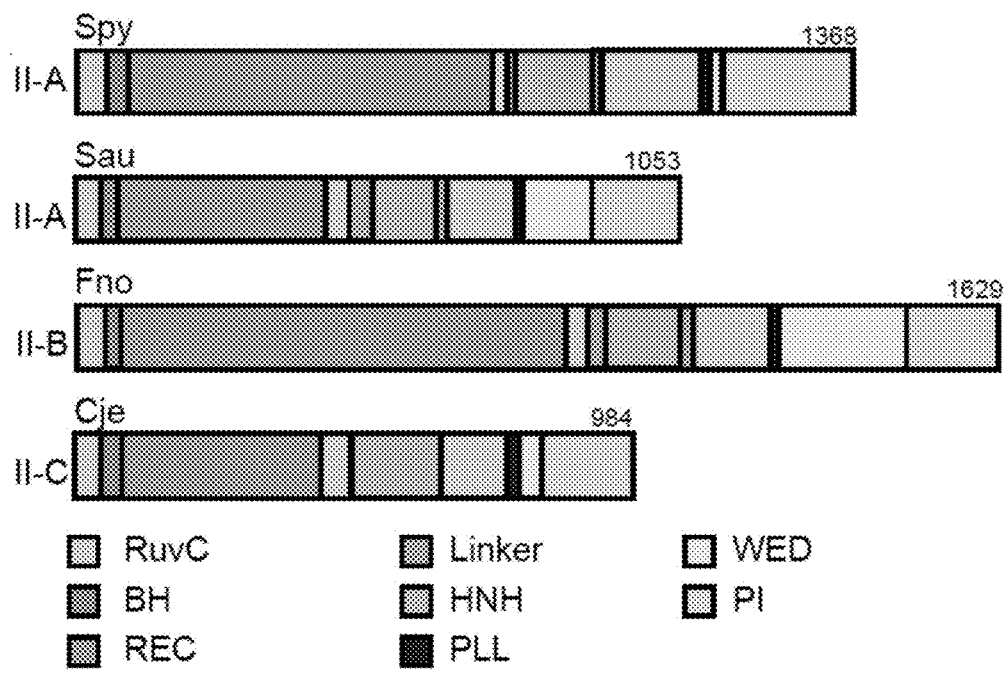
FIG. 3A-3D shows that *Staphylococcus aureus* Cas9 (SauCas9) cleaves single-stranded RNA (ssRNA) without a short DNA oligo containing the PAM sequence (PAMmer). Schematic of Cas9 proteins tested for single-guide RNA (sgRNA) mediated RNA cleavage, which shows the following: RuvC nuclease domain (RuvC), bridge-helix (BH), recognition domain (REC), HNH nuclease domain (HNH), phosphate-lock loop (PLL), wedge domain (WED), and PAM-interacting domain (PI) (FIG. 3A). Adapted from Nishimasu H et al., *Cell* 2015; 162(5):1113-26; Nishimasu H et al., *Cell* 2014; 156(5):935-49; Hirano H et al., *Cell* 2016; 164(5):950-61; and Yamada M et al., *Mol. Cell.* 2017; 65(6):1109-21. Representative in vitro cleavage of ssRNA (FIG. 3B) by Cas9-sgRNA ribonucleoprotein (RNP) complexes of homologs in FIG. 3A. Radiolabeled pUC target RNA was incubated with Cas9 RNP at 37° C. and time points were taken at 0, 10, 30, and 60 min. Full time course is presented in FIG. 4B. T1 indicates size markers generated by RNase T1 digestion of ssRNA target. Size in nucleotides is indicated on the left. In vitro cleavage assay of various RNA substrates (FIG. 3C). Full time course is presented in FIG. 6A, 6D. Schematic of the Cas9-sgRNA RNP complex and various RNA substrates (FIG. 3D).
Figure 3B:
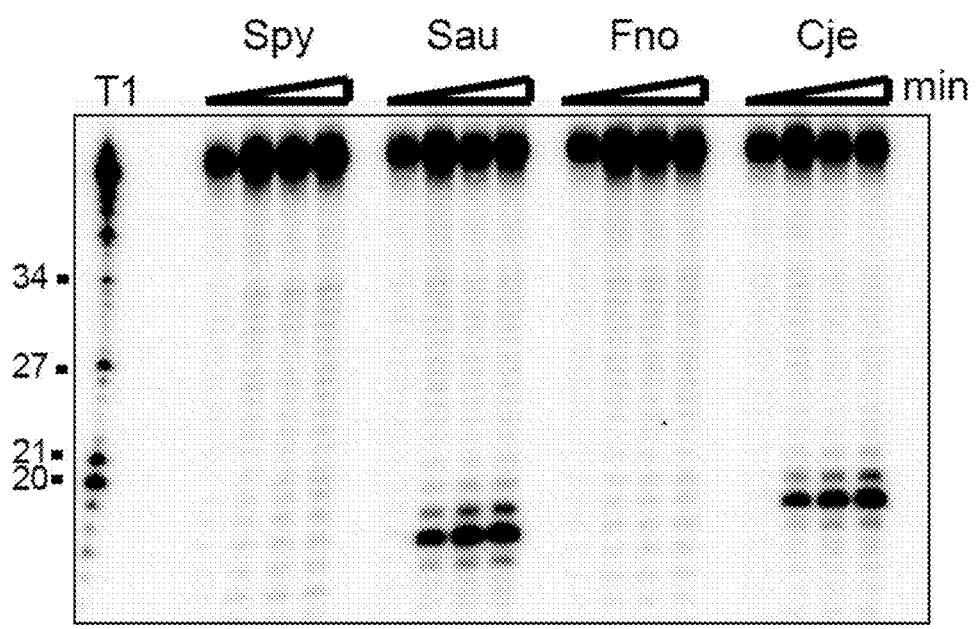
Figure 3C:
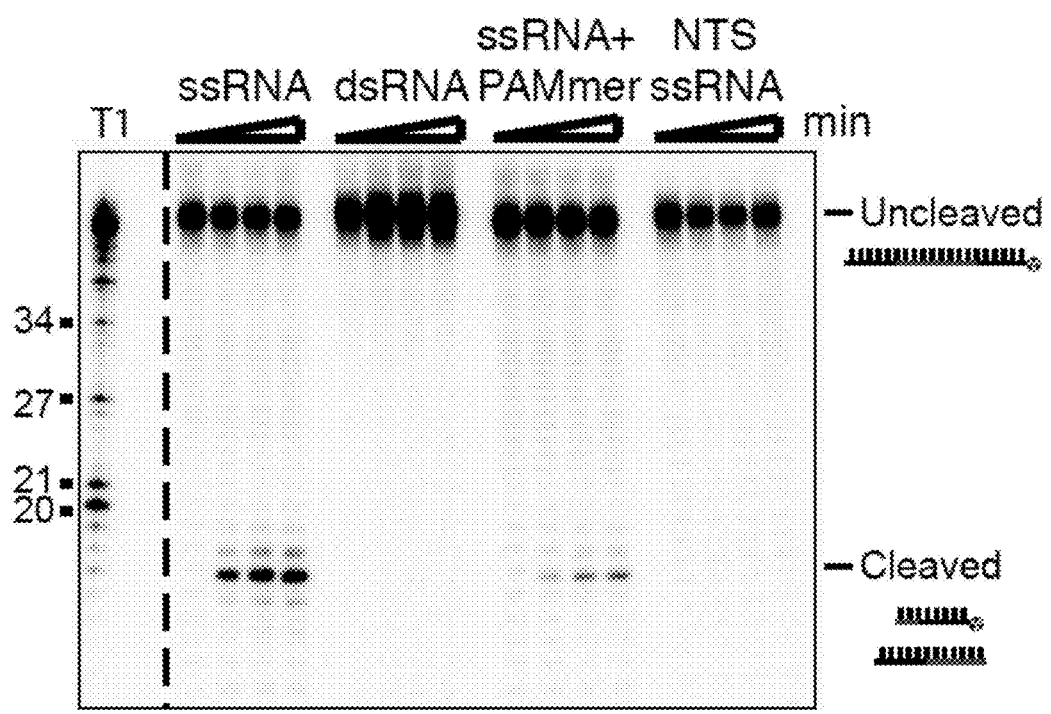
Figure 3D:
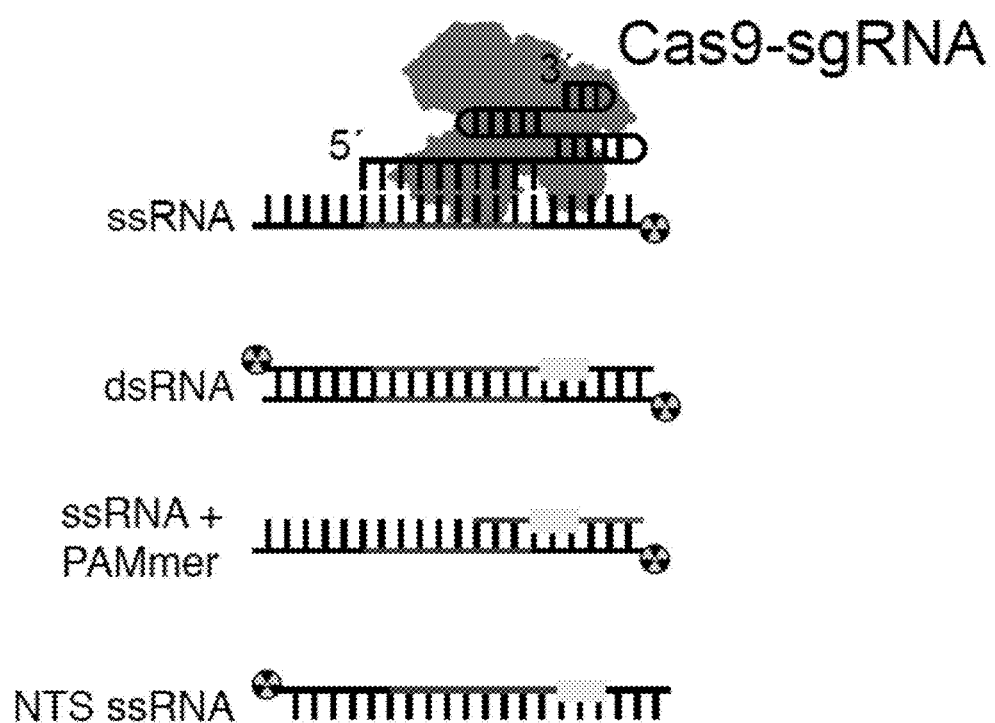
Figure 4A:
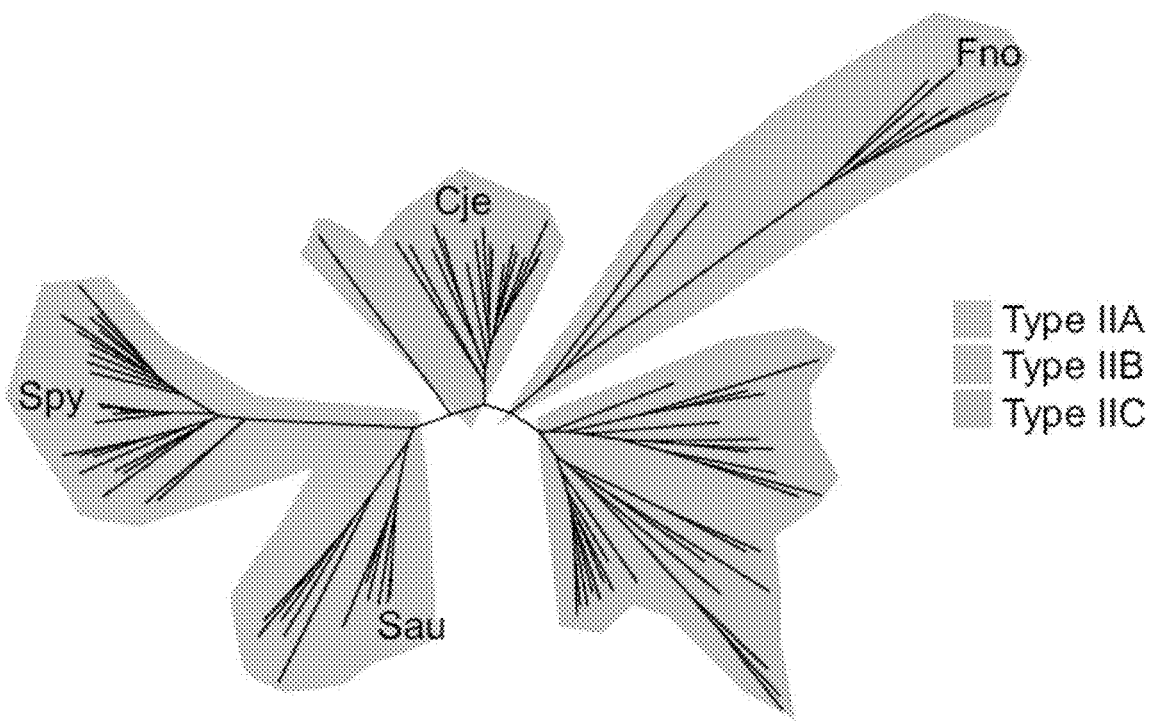
FIG. 4A-4D shows that RNA is cleaved by SauCas9 and CjeCas9. Phylogenetic tree of Cas9 homologs assayed for ssRNA cleavage activity (FIG. 4A). Tree was generated using homologs gathered from Chylinski K et al., *Nucleic Acids Res.* 2014; 42(10):6091-105. Only homologs tested for activity are highlighted as leaves on the tree, and clades are colored by Cas9 sub-type. Representative in vitro cleavage gel (FIG. 4B) for ssRNA targeting by various Cas9 homologs in FIG. 4A. Target used for cleavage was the pUC ssRNA. Time points are 0, 1, 2, 5, 10, 30, 60, and 120 mins. T1 RNase digest size fragments are given on the left. Quantification of fraction (FIG. 4C) cleaved in FIG. 4B. Fit was determined in Prism using a single-exponential decay model. Error bars represent the mean±S.D. (n=3). Apparent pseudo-first order fit parameters (FIG. 4D) of the data in FIG. 4C, where "% cleaved" indicates the fraction of substrate cleaved when the reaction plateaus (mean±S.D.).
Figure 4B:
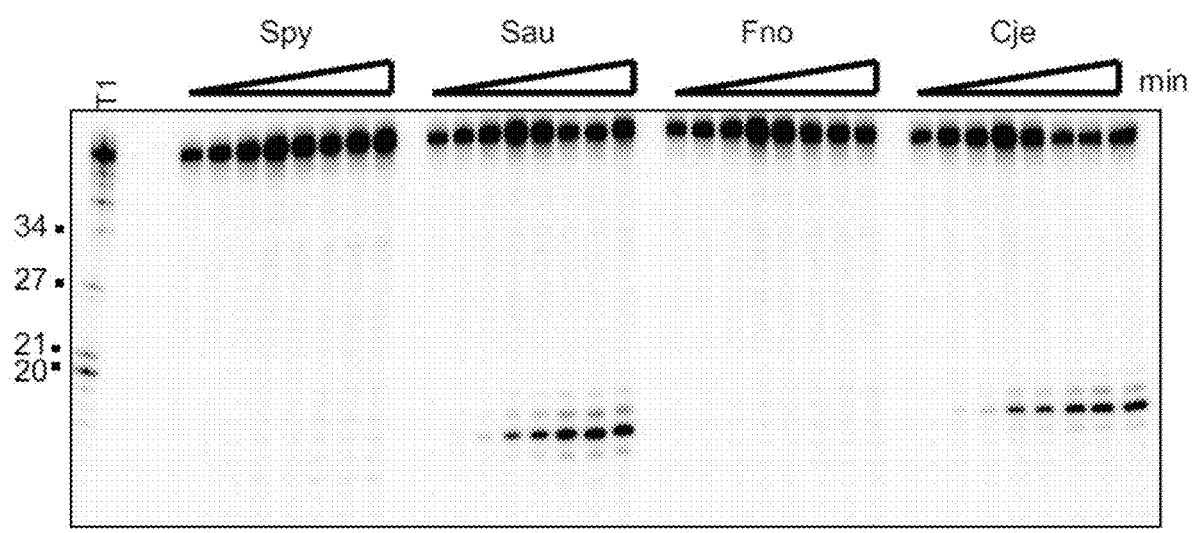
Figures 4C, 4D:
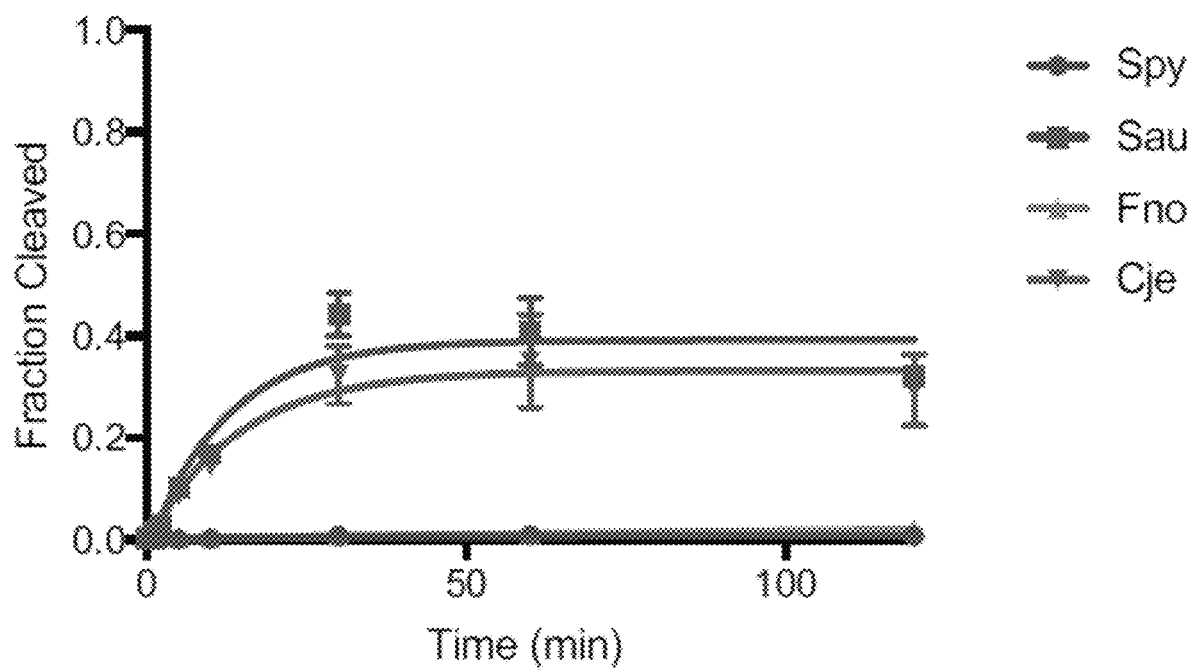

FIG. 2A shows an exemplary synthetic guiding component 200 interacting with the target sequence 212. The synthetic guiding component 200 binds to the target site 211 by way of a targeting portion 204 through non-covalent binding 221. In this manner, the targeting portion confers specificity to the guiding component, thereby allowing certain target sequences to be activated, inactivated, and/or modified.

The synthetic guiding component 200 also includes a first portion 201, a second portion 202, and a linker 205 that covalently links the first and second portions. These portions at the 3' end 207 are configured to recruit the nuclease (e.g., a Cas nuclease) in proximity to the site of the target sequence. Thus, these portions include nucleic acid sequences that provide preferential binding (e.g., specific binding) of the nuclease. Once in proximity, the nuclease can bind and/or cleave the target sequence or a sequence in proximity to the target sequence in a site-specific, programmable manner. In some embodiments, the first and second portions interact by way of non-covalent binding 222, thereby providing secondary structure that beneficially interacts with the nuclease.

The synthetic guiding component 200 can optionally include a third portion 203 at the 5' end 206. The sequence and/or the nucleic acid modifications of the third portion can be optimized to promote binding to the target site or to provide a more accessible substrate to ribonucleoprotein complex.

Figure 20A:
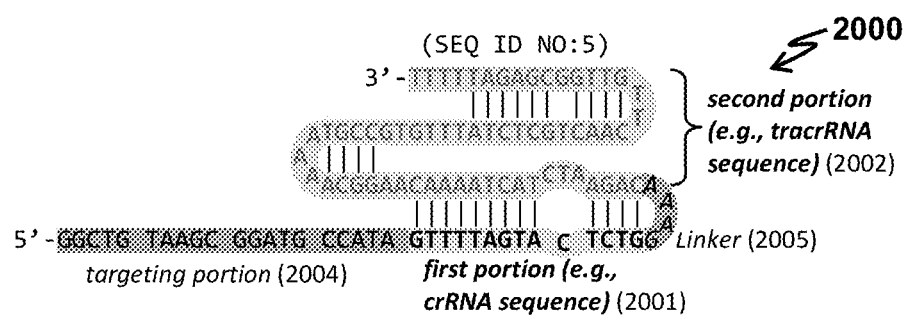
Figure 20B:
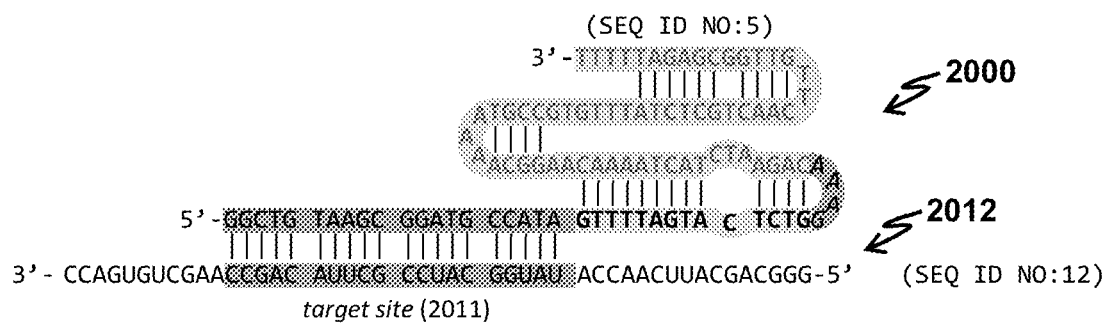

FIG. 20A-20B provides exemplary synthetic guiding components derived from crRNA and tracrRNA sequences. As can be seen, the exemplary synthetic guiding component 2000 includes a first portion 2001 (e.g., a crRNA sequence), a second portion 2002 (e.g., a tracrRNA sequence), a linker 2005 that covalently links the first and second portions, and a targeting portion 2004. Upon binding, the synthetic guiding component 2000 interacts with the target site 2011 of the target sequence 2012.

The first portion, second portion, and linker can be derived in any useful manner. In one instance, the first portion can include a crRNA sequence, a consensus sequence derived from known crRNA sequences, a modified crRNA sequence, or an entirely synthetic sequence known to bind a Cas nuclease or determined to competitively bind a Cas nuclease when compared to a known crRNA sequence. Exemplary sequences for a first portion are described in FIG. 20C-20J (SEQ ID NOs:150-155, 179-186, 213-225, 239-243, 251-253, 256, 257, 260, and 262-264). In some embodiments, the first portion is a crRNA sequence that exhibits at least 50%, 60%, 70%, 80%, 90%, 95%, or 99% of sequence complementarity to any one of SEQ ID NOs: 150-155, 179-186, 213-225, 239-243, 251-253, 256, 257, 260, and 262-264. In other embodiments, the first portion is a fragment (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides) of a crRNA sequence that exhibits at least 50%, 60%, 70%, 80%, 90%, 95%, or 99% of sequence complementarity to any one of SEQ ID NOs:150-155, 179-186, 213-225, 239-243, 251-253, 256, 257, 260, and 262-264.

In another instance, the second portion can include a tracrRNA sequence, a consensus sequence derived from known tracrRNA sequences, a modified tracrRNA sequence, or an entirely synthetic sequence known to bind a Cas nuclease or determined to competitively bind a Cas nuclease when compared to a known tracrRNA sequence. Exemplary sequences for a second portion are described in FIG. 20C-20J (SEQ ID NOs:162-178, 192-212, 232-238, 244-250, 254, 255, 258, 259, 261, and 270-273). In some embodiments, the second portion is a tracrRNA sequence that exhibits at least 50%, 60%, 70%, 80%, 90%, 95%, or 99% of sequence complementarity to any one of SEQ ID NOs: 162-178, 192-212, 232-238, 244-250, 254, 255, 258, 259, 261, and 270-273. In other embodiments, the second portion is a fragment (e.g., having a length of about 4, 5, 6, 7, 8, 9, 10, 11, 12, 13, 14, 15, 16, 17, 18, 19, 20, 22, 24, 26, 28, 30, 32, 34, 36, 38, 40, or more nucleotides) of a tracrRNA sequence that exhibits at least 50%, 60%, 70%, 80%, 90%, 95%, or 99% of sequence complementarity to any one of SEQ ID NOs:162-178, 192-212, 232-238, 244-250, 254, 255, 258, 259, 261, and 270-273.

The linker can be any useful linker (e.g., including one or more transcribable elements, such as a nucleotide or a nucleic acid, or including one or more chemical linkers). Further, the linker can be derived from a fragment of any useful tracrRNA sequence (e.g., any described herein). The first and second portions can interact in any useful manner. For example, the first portion can have a sequence portion that is sufficiently complementary to a sequence portion of the second portion, thereby facilitating duplex formation or non-covalent bonding between the first and second portion. In another example, the second portion can include a first sequence portion that is sufficiently complementary to a second sequence portion, thereby facilitating hairpin formation within the second portion. Exemplary sequences for a linker are described in FIG. 20C-20J (SEQ ID NOs:156-161, 187-191, 226-231, and 265-269). In some embodiments, the linker is a sequence that exhibits at least 50%, 60%, 70%, 80%, 90%, 95%, or 99% of sequence complementarity to any one of SEQ ID NOs:156-161, 187-191, 226-231, and 265-269.

In another embodiment, the guiding component has a structure of W—X—Y-L-Z, in which W includes a third portion (e.g., any third portions described herein), X includes a targeting portion, Y includes a first portion (e.g., any first portions or crRNA sequences described herein), L is a linker (e.g., a covalent bond, a nucleic acid sequence, or any other useful linker), and Z is a second portion (e.g., any second portions or tracrRNA sequences described herein). In yet another embodiment, the synthetic guiding component is a sequence that exhibits at least 50%, 60%, 70%, 80%, 90%, 95%, or 99% of sequence complementarity to any one SEQ ID NOs:274-293, or a fragment thereof (FIG. 21).

In addition, the CRISPR components can be formed from any useful combination of one or more nucleic acids (or a polymer of nucleic acids, such as a polynucleotide). Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids, chimeras, or modified forms thereof. Exemplary modifications include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof. Additional modifications are described herein.

Further exemplary synthetic guiding components and portions thereof (e.g., first portions, second portions, third portions, targeting portions, and linkers) are provided in FIGS. 18A-18E, 20A-20J, and 21. Such components and portions also include fragments of any sequence described therein, as well as substantially identical sequences of any described herein.

Nuclease

The nuclease may be a Cas9 homolog or ortholog. In some embodiments, the nuclease is codon-optimized for expression in a eukaryotic cell. In some embodiments, the nuclease directs cleavage of one or two strands at the location of the target sequence.

Any useful Cas protein or complex can be employed that binds to and/or cleaves a single-stranded sequence (e.g., a ss RNA sequence). Exemplary Cas proteins or complexes include those involved in Type I, Type II, or Type III CRISPR/Cas systems, including but not limited to the CRISPR-associated complex for antiviral defense (Cascade, including a RAMP protein), Cas3 and/or Cas 7 (e.g., for Type I systems, such as Type I-E systems), Cas9 (formerly known as Csn1 or Csx12, e.g., such as in Type II systems), Csm (e.g., in Type III-A systems), Cmr (e.g., in Type III-B systems), Cas10 (e.g., in Type III systems), as well as subassemblies or sub-components thereof and assemblies including such Cas proteins or complexes. Additional Cas proteins and complexes are described in Makarova K S et al., "Evolution and classification of the CRISPR-Cas systems," Nat. Rev. Microbiol. 2011; 9:467-77, which is incorporated herein by reference in its entirety. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In some instances, the nuclease can include one or more mutations, with respect to a corresponding wild-type enzyme, such that the mutated CRISPR enzyme lacks the ability to cleave one or both strands of a target polynucleotide containing a target sequence (e.g., including one or more mutations, such as D10A, N580A, H840A, N854A, and/or N863A in SEQ ID NO:101 or in an amino acid sequence sufficiently aligned with SEQ ID NO:101). Other examples of mutations that render Cas9 a nickase include, without limitation, H840A, N854A, and N863A. In aspects of the invention, nickases may be used for genome editing via homologous recombination. The nuclease can include a nuclear localization sequence (NLS).

Further exemplary nucleases are provided in FIGS. 17A-17E and 19A-19L. Such nucleases also include fragments of any sequence described therein, as well as substantially identical sequences of any described herein.

Complex

A synthetic guiding component and a nuclease can form a complex (i.e., bind via non-covalent interactions). The synthetic guiding component provides target specificity to the complex by comprising a nucleotide sequence that is complementary to a sequence of a target sequence. The nuclease of the complex provides the site-specific activity. In other words, the nuclease is guided to a target sequence (e.g., a target sequence in a chromosomal nucleic acid; a target sequence in a messenger ribonucleic acid; a target sequence in an extrachromosomal nucleic acid, e.g., an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment (e.g., the first and/or second portions) of the guiding component.

Such a complex can be assembled prior to administration to a subject (e.g., a host, a human, a mammal, a pathogen, a plant, etc.). Alternatively, the complex can be transcribed within the subject (e.g., by use of one or more vectors configured to encode the complex, the synthetic guiding component, and/or the nuclease), and administration can include delivering the platform that facilitates such transcription.

Target Sequences

The synthetic guiding component can be employed to target any useful nucleic acid sequence (e.g., present in the host's genomic sequence, host's non-coding sequence, and/or the pathogen's genomic sequence). In one instance, the target sequence can include a sequence present in the host's genomic or non-coding sequence in order, e.g., to activate, inactive, or modify expression of a target (e.g., a protein). In another instance, the target sequence can bind to one or more regulator proteins and enhance their transcription and expression. In yet another instance, one or more polypeptides may be up-regulated, as compared to the normal basal rate. Accordingly, the target sequence can be employed to bind to one or more up-regulated polypeptides in order to inactivate or repress transcription/expression of those polypeptides.

In yet another instance, the target sequence can be employed to activate, inhibit, and/or modify a target sequence (e.g., associated with the presence of a pathogen, etc.). For instance, the target sequence can be configured to activate one or more target sequences encoding proteins that promote programmed cell death or apoptosis (e.g., of the pathogen or of particular tissue types, etc.). For instance, the target sequence can be configured to inactivate or modify one or more target sequences encoding proteins that are suppressed by the pathogen. Exemplary target sequence (e.g., in a pathogen) includes, without limitation, a nucleic acid sequence encoding a virulence factor (e.g., a lipase, a protease, a nuclease (e.g., a DNAse or an RNase), a hemolysin, a hyaluronidase, an immunoglobulin protease, an endotoxin, or an exotoxin), a cell surface protein (e.g., an adhesion), an envelope protein (e.g., a phospholipid, a lipopolysaccharide, a lipoprotein, or a polysaccharide), a glycoprotein, a polysaccharide protein, a transmembrane protein (e.g., an invasin), or a regulatory protein.

The synthetic guiding component can be employed to activate the target sequence (e.g., the Cas polypeptide can include one or more transcriptional activation domains, which upon binding of the Cas polypeptide to the target sequence, results in enhanced transcription and/or expression of the target sequence), inactivate the target sequence (e.g., the Cas polypeptide can bind to the target sequence, thereby inhibiting expression of one or more proteins encoded by the target sequence; the Cas polypeptide can introduce single-stranded breaks in the target sequence, thereby inactivating the gene; or the Cas polypeptide can include one or more transcriptional repressor domains, which upon binding of the Cas polypeptide to the target sequence, results in reduced transcription and/or expression of the target sequence), and/or modify the target sequence (e.g., the Cas polypeptide can cleave the target sequence of the pathogen and optionally inserts a further nucleic acid sequence).

Methods and Uses

The components and complexes can be employed in any useful manner. The present components and complexes can be adapted to recognize the target and, if desired, cleave the target sequence. Alternatively, the components and complexes can be adapted to recognize the target and, if desired, provide a signal indicating presence of the target (e.g., by cleaving a reporter that provides a detectable signal once the reporter is cleaved).

Yet other uses include methods of treating a patient or a subject in need (e.g., for a particular disease state or infection). Such methods include administration (e.g., prophylactic administration) of an effective amount of a pharmaceutical composition including an effective amount of a component and/or a complex according to the present invention.

The present invention can also include diagnostic methods, which can include administering to a patient in need an effective amount of a population of a diagnostic component and/or complex, whereupon the recognition of the target is evidenced by a reporter component (moiety) that will enable a diagnosis of the existence of a disease state in the patient.

The components and complexes can be designed in any useful manner. In one embodiment, the component is designed to bind to one or more targets (e.g., target sequences) that are diagnostic for a disease state (e.g., an autoimmune disease, a blood disease, a brain and nervous system disease, a cancer, a childbirth-related or a pregnancy-related disease, an endocrine disease, an environmentally-acquired disease, an infection (e.g., a bacterial infection or a viral infection), an inherited disease, an immune system disease, or an organ disease).

In another embodiment, the component is designed to bind to one or more targets (e.g., target sequences) including a single nucleotide polymorphism (SNP), a point mutation (including a combination of point mutations at different locations), a somatic mutation, an aneuploidy, a microsatellite alteration, an epigenetic modification, etc.

The present invention can include detection methods (e.g., in a test sample), which can include designing a targeting portion of a synthetic guiding component, where the targeting portion is configured to bind to the single-stranded target sequence. Such methods can also include use of a label or a reporter, which can provide a detectable signal upon recognition of the target by the component. In one embodiment, the synthetic guiding component including one or more labels (e.g., any described herein). In another embodiment, the synthetic guiding component can be used in conjunction with a reporter (e.g., a reporter including a non-target strand that optionally includes a label or a combination of labels, such as a quencher and a fluorophore), in which recognition of the target results in the reporter emitting a detectable signal (e.g., in which cleavage of the target and/or non-target strand results in a detectable signal). Exemplary non-target strands can include, e.g., a nucleic acid substrate, such as a mismatched nucleic acid (e.g., including a mismatch between the non-target and target stands for contiguous residues over a region of 7, 8, 9, 10, 11, 12, 13, 14, 15, 16, 17, 18, 19, 20, 21, 22, 23, 24, 25, 30, 35, 40, 45, 50, or more nucleotides) or any described herein.

Such detection can be conducted in any useful manner, such as in a cleavage assay, a kit, or in a diagnostic device (e.g., a lateral flow assay, a microfluidic device, a flow strip, wells, tubes, droplets, combinations thereof, etc.) in combination with one or more optional labels. Exemplary labels can include one or more fluorescent labels, quencher labels, colorimetric labels, quantum dots, nanoparticles, microparticles, barcodes, radio labels (e.g., RF labels or barcodes), avidin, biotin, tags (e.g., affinity tags), dyes, an enzyme that can optionally include one or more linking agents and/or one or more dyes, aptamers, as well as combinations thereof etc.

A test sample can include any useful sample, such as a microorganism, a virus, a bacterium, a fungus, a parasite, a helminth, a protozoon, a cell, tissue, a fluid, a swab, a biological sample (e.g., blood, serum, plasma, cerebrospinal fluid, lymph fluid, interstitial fluid, mucus, saliva, sera, spinal fluid, sputum, stool, synovial fluid, urine, a swab from skin or a mucosal membrane, a combination thereof, etc.), a plant, an environmental sample (e.g., surfaces, fluids, air, soil, and/or water), etc. Samples can include one or more biomarkers, such as circulating cells (e.g., circulating tumor cells), cell types (e.g., lymphocytes), cell-free chromatin, cell-free nucleic acid (e.g., cell-free DNA), exosomes, a loss of heterozygosity marker, mutations (e.g., point mutations, aneuploidy, etc.), microRNA (miRNA) signatures, etc. A test sample can include any useful target or pathogen. Exemplary targets and pathogens include a bacterium, such as such as *Bacillus* (e.g., *B. anthracis*), Enterobacteriaceae (e.g., *Salmonella, Escherichia coli, Yersinia pestis, Klebsiella,* and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., L. monocytogenes), Brucella (e.g., B. abortus, B. melitensis, or B. suis), Vibrio (e.g., V. cholerae), Corynebacterium diphtheria, Pseudomonas (e.g., P. pseudomallei or P. aeruginosa), Burkholderia (e.g., B. mallei or B. pseudomallei), Shigella (e.g., S. dysenteriae), Rickettsia (e.g., R. rickettsii, R. prowazekii, or R. typhi), Francisella tularensis, Chlamydia psittaci, Coxiella burnetii, Mycoplasma (e.g., M mycoides), etc.; an allergen, such as mycotoxins, mold spores, or bacterial spores such as Clostridium botulinum and C. perfringens; a toxin, such as ricin, mycotoxin, tetrodotoxin, anthrax toxin, botulinum toxin, staphylococcal entertoxin B, or saxitoxin; a virus (e.g., an RNA virus or a DNA virus, including single-stranded or double-stranded forms thereof), such as Adenoviridae (e.g., adenovirus), Arenaviridae (e.g., Lassa virus or Machupo virus), Bunyaviridae (e.g., Hantavirus, Rift Valley fever virus, or Sin Nombre virus), Caliciviridae (e.g., norovirus), Coronaviridae, Filoviridae (e.g., Ebola virus, Sudan ebolavirus (SUDV), Zaire ebolavirus (EBOV), Bundibugyo virus (BDBV), and Marburg virus (MARV)), Flaviviridae (e.g., dengue virus (DENV), hepatitis C virus (HCV), Japanese encephalitis virus (JEV), St. Louis encephalitis virus (SLEV), West Nile virus (WNV), and yellow fever virus (YFV)), Hepadnaviridae (e.g., hepatitis B virus), Herpesviridae (e.g., herpes simplex viruses), Nairoviridae (e.g., Crimean-Congo hemorrhagic fever orthonairovirus and Crimean-Congo hemorrhagic fever virus), Orthomyxoviridae (e.g., influenza viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., Chikungunya virus (CHIKV), Eastern equine encephalitis virus (EEEV), encephalitis viruses, Ross River virus (RRV), rubella virus, Sindbis virus (SINV), Venezuelan equine encephalitis virus (VEEV), Western equine encephalitis virus (WEEV), and yellow fever virus)); a protozoon, such as Cryptosporidium parvum, Encephalitozoa, Plasmodium, Toxoplasma gondii, Acanthamoeba, Entamoeba histolytica, Giardia lamblia, Trichomonas vaginalis, Leishmania, or Trypanosoma (e.g., T. brucei and T. cruzi); a helminth, such as cestodes (tapeworms), trematodes (flukes), or nematodes (roundworms, e.g., Ascaris lumbricoides, Trichuris trichiura, Necator americanus, or Ancylostoma duodenale); a parasite (e.g., any protozoa or helminths described herein); a fungus, such as Aspergilli, Candidae, Coccidioides immitis, and Cryptococci; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene of any useful pathogen, such as those described herein); or a genetic modification (e.g., antibiotic resistance marker gene). Targets also include food-borne pathogens, such as Salmonella (e.g., Salmonella Typhimurium), pathogenic E. coli (e.g., O157:H7), Bacillus (e.g., B. cereus), Clostridium botulinum, Listeria monocytogenes, Yersinia (e.g., Y. enterocolitica), Norovirus (e.g., Norwalk virus), Shigella, Staphylococcus aureus, Toxoplasma gondii, Vibrio (e.g., V. vulnificus, V. cholera, V. parahaemolyticus), Campylobacter jejuni, and Clostridium perfringens; and weaponized pathogens, such as Bacillus anthracis, Yersinia pestis, Francisella tularensis, Brucella (e.g., B. suis), Burkholderia mallei, Burkholderia pseudomallei, Shigella, Clostridium botulinum, Variola (e.g., V. major), Filoviridae (e.g., Ebola virus and Marburg virus), Arenaviridae (e.g., Lassa virus and Machupo virus), Clostridium perfringens, any food-borne pathogen (e.g., Salmonella species, Escherichia coli O157: H7, or Shigella), Chlamydia psittaci, Coxiella burnetii, Staphylococcal aureus, Rickettsia (e.g., R. prowazekii or R. rickettsii), Alphavirus (e.g., Venezuelan equine encephalitis virus, eastern equine encephalitis virus, or western equine encephalitis virus), Vibrio cholerae, Cryptosporidium parvum, Henipavirus (e.g., Nipah virus), Bunyaviridae (e.g., Hantavirus or Rift Valley fever virus), Flaviviridae (e.g., Japanese encephalitis virus and Yellow fever virus), and Coccidioides spp.

In some embodiments, the sample or target includes an RNA virus (e.g., including a portion thereof). Exemplary, non-limiting RNA viruses include Arenaviridae (e.g., Guanarito virus, Junin virus, Lassa virus, Lujo virus, lymphocytic choriomeningitis virus, Machupo virus, Sabia virus, and Whitewater Arroyo virus), Arteriviridae (e.g., arterivirus and equine arteritis virus), Aspiviridae (e.g., citrus psorosis ophiovirus), Astroviridae (e.g., astrovirus), Bornaviridae (e.g., Borna disease virus), Bunyaviridae (e.g., California encephalitis virus and hantavirus), Bunyavirales (e.g., Cache Valley virus, California encephalitis virus, Crimean-Congo hemorrhagic fever, Hantaan virus, La Crosse encephalitis virus, Jamestown Canyon virus, Rift Valley fever virus, and Snowshoe hare virus), Caliciviridae (e.g., Norwalk virus), Coronaviridae (e.g., corona virus), Filoviridae (e.g., Ebola virus, Marburg virus, and Sudan virus), Fimoviridae, Flaviviridae (e.g., dengue virus, hepatitis C virus, Japanese encephalitis virus, St. Louis encephalitis virus, Usutu virus, West Nile virus, yellow fever virus, and Zika virus), Hepeviridae (e.g., hepatitis E virus), Jonviridae, Metaviridae, Nyamiviridae, Orthomyxoviridae (e.g., influenza virus A, influenza virus B, influenza virus C, influenza virus D, isavirus, quaranjavirus, and thogotovirus), Orthohantavirus (e.g., Sin Nombre virus), Orthonairovirus (e.g., Crimean-Congo hemorrhagic fever orthonairovirus, Dugbe virus, Kasokero virus, and Nairobi sheep disease virus), Orthotospovirus, Paramyxoviridae (e.g., avian paramyxovirus, canine distemper virus measles virus, Hendra virus, human parainfluenza viruses, mumps virus, Nipah virus, respiratory syncytial virus, Rinderpest virus, and Sendai virus), Peribunyaviridae, Phasmaviridae, Phenuiviridae (e.g., Rift Valley fever phlebovirus), Picornaviridae (e.g., aphthovirus, cardiovirus, coxsackie virus, enterovirus, erbovirus, hepatovirus, kobuvirus, parechovirus, poliovirus, rhinovirus, and teschovirus), Pseudoviridae, Reoviridae (e.g., Banna virus, cypovirus, reovirus, and rotavirus), Retroviridae (e.g., human immunodeficiency virus (HIV), hepatitis B virus, and cauliflower mosaic virus), Rhabdoviridae (e.g., rabies virus and vesicular stomatitis virus), and Togaviridae (e.g., alphavirus, Chikungunya virus, Eastern equine encephalitis virus, rubella virus, O'Nyong-nyong fever virus, Ross River fever virus, Semliki Forest virus, Sindbis fever virus, Venezuelan equine encephalitis virus, and Western equine encephalitis virus).

EXAMPLES

Example 1: RNA-Dependent RNA Targeting by CRISPR-Cas9

Double-stranded DNA (dsDNA) binding and cleavage by Cas9 is a hallmark of type II CRISPR-Cas bacterial adaptive immunity. All known Cas9 enzymes are thought to recognize DNA exclusively as a natural substrate, providing protection against DNA phage and plasmids. Here, we show that Cas9 enzymes from both subtypes II-A and II-C can recognize and cleave single-stranded RNA (ssRNA) by an RNA-guided mechanism that is independent of a protospacer-adjacent motif (PAM) sequence in the target RNA. RNA-guided RNA cleavage was programmable and site-specific, and we find that this activity can be exploited to reduce infection by single-stranded RNA phage in vivo. We also demonstrate that Cas9 can direct PAM-independent repression of protein synthesis in bacteria. These results indicate that a subset of Cas9 enzymes has the ability to act on both DNA and RNA target sequences, and suggest the potential for use in programmable RNA targeting applications.

Prokaryotic clustered regularly interspaced short palindromic repeat (CRISPR) systems provide immunity against plasmids and bacteriophage by using foreign DNA stored as CRISPR spacer sequences together with CRISPR-associated (Cas) nucleases to stop infection (see, e.g., Wright A V et al., "Biology and applications of CRISPR systems: harnessing nature's toolbox for genome engineering," *Cell* 2016; 164 (1-2):29-44; and Mohanraju P et al., "Diverse evolutionary roots and mechanistic variations of the CRISPR-Cas systems," *Science* 2016; 353(6299):aad5147 (14 pp.)). One such nuclease, Cas9 of the type II systems, employs a CRISPR RNA (crRNA) and a trans-activating crRNA (tracrRNA) to target spacer-complementary regions (protospacers) on the foreign genetic element to guide double-stranded DNA cleavage (see, e.g., Jinek M et al., "A programmable dual-RNA-guided DNA endonuclease in adaptive bacterial immunity," *Science* 2012; 337(6096):816-21). A protospacer adjacent motif (PAM) must also be present for the Cas9-RNA complex to bind and cleave DNA (see, e.g., Jinek M et al., *Science* 2012; 337(6096):816-21; Gasiunas G et al., "Cas9-crRNA ribonucleoprotein complex mediates specific DNA cleavage for adaptive immunity in bacteria," *Proc. Nat'l Acad. Sci. USA* 2012; 109(39):E2579-86; Anders C et al., "Structural basis of PAM-dependent target DNA recognition by the Cas9 endonuclease," *Nature* 2014; 513(7519):569-73; and Szczelkun M D et al., "Direct observation of R-loop formation by single RNA-guided Cas9 and Cascade effector complexes," *Proc. Nat'l Acad. Sci. USA* 2014; 111(27):9798-803). Combining the crRNA and tracrRNA into a chimeric, single-guide RNA (sgRNA) simplified the system for widespread adoption as a versatile genome editing technology (see, e.g., Jinek M et al., *Science* 2012; 337(6096):816-21).

To date, both genetic and biochemical data support the conclusion that in vivo, Cas9 is exclusively a DNA-targeting enzyme. Nonetheless, multiple studies have harnessed Cas9 for RNA targeting under specific circumstances. For example, *S. pyogenes* Cas9 (SpyCas9) can be supplied with a short DNA oligo containing the PAM sequence (a PAMmer) to induce single-stranded RNA (ssRNA) binding and cutting (see, e.g., O'Connell M R et al., "Programmable RNA recognition and cleavage by CRISPR/Cas9," *Nature* 2014; 516(7530):263-6; and Nelles D A et al., "Programmable RNA tracking in live cells with CRISPR/Cas9," *Cell* 2016; 165(2):488-96). More recently, it was demonstrated that SpyCas9 could be used to target repetitive RNAs and repress translation in certain mRNAs in the absence of a PAMmer (see, e.g., Liu Y et al., "Targeting cellular mRNAs translation by CRISPR-Cas9," *Sci. Rep.* 2016; 6:29652 (9 pp.); and Batra R et al., "Elimination of toxic microsatellite repeat expansion RNA by RNA-targeting Cas9," *Cell* 2017; 170(5):899-912).

A different Cas9 homolog from *Francisella novicida* (FnoCas9) has been implicated in degradation of a specific mRNA but through a mechanism independent of RNA-based cleavage (see, e.g., Sampson T R et al., "A CRISPR/Cas system mediates bacterial innate immune evasion and virulence," *Nature* 2013; 497(7448):254-7). Together with evidence that some Cas9 homologs can target single-stranded DNA substrates under some conditions (see, e.g., Ma E et al., "Single-stranded DNA cleavage by divergent CRISPR-Cas9 enzymes," Mol. *Cell* 2015 Nov. 5; 60(3):398-407; and Zhang Y et al., "DNase H activity of *Neisseria meningitidis* Cas9," *Mol. Cell.* 2015; 60(2):242-55), these studies raised the possibility that certain Cas9 enzymes might have intrinsic RNA-guided RNA cleavage activity.

To determine whether evolutionarily divergent Cas9 homologs have a native capacity for programmable RNA targeting, we compared biochemical behavior of enzymes from the three major Cas9 subtypes. This analysis revealed that certain type II-A and II-C Cas9s can bind and cleave single-stranded RNA sequences with no requirement for a PAM or PAMmer. Furthermore, we found that this activity can inhibit mRNA translation and protect cells from infection by ssRNA phage by a mechanism reminiscent of RNA-guided DNA targeting. These results establish the utility of Cas9 for facile RNA-guided RNA targeting and suggest that this activity may have biological relevance in bacteria. Additional details follow.

Example 2: Materials and Methods

The following materials and methods were employed for data provided herein. Such materials and methods are exemplary, as would be understood by a skilled artisan.

Phylogenetic tree construction and RNA folding: Cas9 homolog sequences were obtained from Chylinski and colleagues (see, e.g., Chylinski K et al., "Classification and evolution of type II CRISPR-Cas systems," *Nucleic Acids Res.* 2014; 42(10):6091-105). A structure-guided alignment was produced using PROMALS3D (see, e.g., Pei J et al., "PROMALS3D: a tool for multiple protein sequence and structure alignments," *Nucleic Acids Res.* 2008; 36(7):2295-300), and a maximum-likelihood tree was inferred using PHYML3.0 (see, e.g., Guindon S et al., "New algorithms and methods to estimate maximum-likelihood phylogenies: assessing the performance of PhyML 3.0," *Syst. Biol.* 2010; 59(3):307-21). The structure of the pUC ssRNA target was predicted using Mfold (see, e.g., Zuker M, "Mfold web server for nucleic acid folding and hybridization prediction," *Nucleic Acids Res.* 2003; 31(13):3406-15).

Protein purification: All proteins were expressed as His-Maltose-Binding Protein (MBP) fusions (Addgene vector #29706) in *E. coli* strain BL21 (DE3). Cells were grown to an $OD_{600}$ of 0.6-0.8, induced with 0.4 M isopropylthiogalactoside (IPTG), and then incubated overnight at 16° C. with shaking. Proteins were purified using Superflow Ni-NTA affinity resin (Qiagen, Valencia, Calif.), followed by a HiTrap HP Heparin column (GE Healthcare, Pittsburgh, Pa.) and gel filtration on a Superdex S200 (GE Healthcare, Pittsburgh, Pa.), as previously described (see, e.g., Jinek M et al., "A programmable dual-RNA-guided DNA endonuclease in adaptive bacterial immunity," *Science* 2012; 337 (6096):816-21). Cas9 protein sequences can be found in FIG. 17A-17E.

Oligonucleotide purification and radiolabeling: DNA oligonucleotides were synthesized by Integrated DNA Technologies, Inc. (Coralville, Iowa). Target RNAs and sgRNAs were transcribed in vitro as previously described (see, e.g., Sternberg S H et al., "Mechanism of substrate selection by a highly specific CRISPR endoribonuclease," RNA 2012; 18(4):661-72). DNA targets and in vitro transcribed RNAs were gel purified by 7 M urea denaturing PAGE. Target RNAs and DNAs were 5' end-labeled with [γ-P32-ATP] by treatment with PNK (New England Biolabs, Inc., Ipswich, Mass.). T1 sequencing and hydrolysis ladders were prepared according to manufacturer's directions (Ambion, Inc., Grand Island, N.Y.). A list of all sgRNAs and targets can be found in FIG. 18A-18E.

In vitro cleavage assays: Cas9 was reconstituted with equimolar sgRNA in 1× cleavage buffer (20 mM Tris-HCl-pH 7.5, 200 mM KCl, 1 mM tris(2-chloroethyl) phosphate (TCEP), 5% glycerol, 5 mM $MgCl_2$) for 10 min at 37° C., then immediately placed on ice. Cleavage reactions were conducted with 1 nM target and 10 nM reconstituted Cas9-sgRNA in 1× cleavage buffer unless otherwise noted. Structured RNA substrates were prepared by annealing the target strand with 10-fold excess of the non-target strand to ensure that all target is complexed prior to the cleavage reaction. Reactions were incubated at 37° C. for the indicated time and quenched in Heparin-EDTA buffer (10 μg/ml heparin, 25 mM EDTA) at 25° C. for 5 min. Reactions were diluted with 2× formamide loading buffer and incubated at 95° C. for 5 min prior to separation on a 15% denaturing 7 M urea PAGE gel. Gels were dried overnight and exposed to a phosphor imaging screen (Amersham/GE Healthcare, Pittsburgh, Pa.). Results were visualized on a Typhoon (GE Healthcare, Pittsburgh, Pa.) and quantified in ImageQuantTL (v8.1, GE Healthcare, Pittsburgh, Pa.). Cleavage reactions were fit with a one-phase exponential decay model in Prism7 (GraphPad Software, La Jolla, Calif.).

Filter binding and electrophoretic mobility shift assays: Binding reactions consisted of 750 nM catalytically inactive SauCas9 reconstituted with sgRNA to the final concentrations indicated. Radiolabeled target RNA was added to a final concentration of 1 nM and the reactions were incubated at 37° C. for one hour. Bound probe was separated from unbound using a three-filter system on a vacuum manifold (see, e.g., Rio D C, "Filter-binding assay for analysis of RNA-protein interactions," Cold Spring Harb. Protoc. 2012; 2012(10):1078-81). Membranes were allowed to dry prior to phosphor imaging and quantification. EMSAs were performed in the presence of 300 nM dSauCas9 and 1 nM radiolabeled target strand DNA pre-annealed in the presence of 10× non-target strand. Complexes were incubated at 37° C. for one hour prior to separation on 6% non-denaturing PAGE. Gels were dried prior to phosphor imaging. Binding isotherms were determined in Prism using a one-site binding model.

MS2 screen and plaque assay: All guides of length 20-23 nt antisense to the MS2 bacteriophage genome were synthesized (CustomArray Inc., Bothell, Wash.) and cloned into a guide expression vector (see, e.g., Oakes B L et al., "Profiling of engineering hotspots identifies an allosteric CRISPR-Cas9 switch," Nat. Biotechnol. 2016; 34(6):646-51) modified with the SauCas9 sgRNA scaffold. XL1-Blue E. coli cells with a vector containing a tetracycline-inducible wtSauCas9 construct were made electrocompetent and transformed with the MS2-guide plasmid library in triplicate. Approximately $1 \times 10^6$ transformants were grown for 30 min at 37° C. with shaking prior to addition of antibiotics and 10 nM anhydrotetracycline (aTc) (Sigma-Aldrich Corp., St. Louis, Mo.) for protein induction. After an additional 30 min of growth, cultures were split into three equal pools and treated with none, $3.3 \times 10^6$, or $3.3 \times 10^7$ MS2 bacteriophage. After three hours of infection, cells were plated on LB-agar supplemented with antibiotics and incubated at 37° C. for 16 hours. Plates were scraped with LB and plasmids were isolated using a MidiPrep kit (Qiagen, Valencia, Calif.), according to the manufacturer's protocol.

High-throughput sequencing libraries were prepared by PCR amplification of the variable region of the guide plasmid. Dual unique-molecular identifiers (UMIs), included to separate true single-nucleotide mismatches, as well as duplicates, from PCR artifacts (see, e.g., Kou R et al., "Benefits and challenges with applying unique molecular identifiers in next generation sequencing to detect low frequency mutations," PLoS One 2016; 11(1):e0146638 (15 pp.)), were incorporated during a single round of PCR. Excess UMIs were removed by ExoI digestion (Thermo Scientific, Waltham, Mass.) prior to library amplification and barcoding. Individual guides (FIG. 18C) were cloned using oligonucleotides synthesized by IDT and co-transformed into XL1-Blue E. coli cells with the SauCas9 vector. Resistance to MS2 bacteriophage was conducted using a soft-agar overlay method (see, e.g., Abudayyeh O O et al., "C2c2 is a single-component programmable RNA-guided RNA-targeting CRISPR effector," Science 2016; 353(6299): aaf5573 (9 pp.)), and plaque forming units (PFUs) were calculated. To minimize variability in plaquing efficiency, the same phage dilutions were used for all experiments.

MS2 survival and mismatch analysis: After applying a low-pass filter, reads were trimmed using cutadapt v. 1.14 (see, e.g., Martin M, "Cutadapt removes adapter sequences from high-throughput sequencing reads," EMBnet.journal 2011; 17(1):10-2); and paired-end overlapping reads were merged using pandaseq for error correction (see, e.g., Masella A P et al., "PANDAseq: PAired-eND Assembler for Illumina sequences," BMC Bioinformatics 2012; 13:31 (7 pp.)). Reads were mapped to the MS2 genome with bowtie2 v2.3.0 (see, e.g., Langmead B et al., "Fast gapped-read alignment with Bowtie 2," Nat. Methods 2012; 9(4):357-9) using the "very-sensitive" option and de-duplicated based on the dual-UMI (see, e.g., Smith T et al., "UMI-tools: modeling sequencing errors in Unique Molecular Identifiers to improve quantification accuracy," Genome Res. 2017; 27(3): 491-499). Feature counts were obtained using HTSeq—count (see, e.g., Anders S et al., "HTSeq—a Python framework to work with high-throughput sequencing data," Bioinformatics 2015; 31(2):166-9). Differential expression was calculated using standard pipelines implemented in "edgeR" (see, e.g., Robinson M D et al., "edgeR: a Bioconductor package for differential expression analysis of digital gene expression data," Bioinformatics 2010; 26(1):139-40; and McCarthy D J et al., "Differential expression analysis of multifactor RNA-Seq experiments with respect to biological variation," Nucleic Acids Res. 2012; 40(10):4288-97).

Significantly enriched guides were defined as those with an FDR-corrected p-value <0.05. Guides with a positive fold-change compared to the control were mapped to the MS2 genome and visualized using the "Sushi" package (see, e.g., Phanstiel D H et al., "Sushi®: flexible, quantitative and integrative genomic visualizations for publication-quality multi-panel figures," Bioinformatics 2014; 30(19):2808-10). To examine for nucleotide composition bias, sequences of guides with a significant positive enrichment were aligned at the 3' end (PAM-proximal) and motifs were analyzed using the WebLogo server (see, e.g., Crooks G E et al., "WebLogo: a sequence logo generator," Genome Res. 2004; 14(6):1188-90). The distribution of $log_2$ fold-change values of significantly enriched guides were plotted as box and whisker plots in Prism.

The secondary structure of the MS2 genome was obtained from Dai X et al., "In situ structures of the genome and genome-delivery apparatus in a single-stranded RNA virus," Nature 2017; 541(7635):112-6; and reads were mapped and visualized in Forna (see, e.g., Kerpedjiev P et al., "Forna (force-directed RNA): simple and effective online RNA secondary structure diagrams," Bioinformatics 2015; 31(20):3377-9. $Log_2$ fold-change values of single-nucleotide mismatch (SNP) guides for each treatment were partitioned by length and averaged at each position. Some of the high-throughput sequencing data are available through the Sequencing Read Archive under the BioProject accession number PRJNA413805.

E. coli in vivo GFP repression: Based on the system outlined previously, SauCas9 was cloned into a tetracycline-inducible vector, while individual guides are under control of a constitutive promoter (see, e.g., Oakes B L et al., Nat. Biotechnol. 2016; 34(6):646-51). Plasmids were transformed into an E. coli strain with a GFP reporter gene integrated into the chromosome (see, e.g., Qi L S et al., Cell 2013; 152(5):1173-83). Cultures were grown in M9 medium supplemented with 0.4% w/v glucose to mid-log phase and diluted to an $OD_{600}$ of 0.05 prior to transfer to a Tecan Microplate reader (Tecan Systems, San Jose, Calif.). Protein expression was induced with 10 nM anhydrotetracycline (aTc). GFP and $OD_{600}$ were measured every ten minutes for at least 18 hours. Curves of GFP expression over time were fit with a logistic growth model in Prism. At 80% of the maximum value, or at least after 16 hours of growth, the GFP signal was normalized by cell density at $OD_{600}$.

To account for effects of guide and protein expression, $GFP/OD_{600}$ was normalized to a null guide or null protein culture, respectively. As expression of different guides change GFP expression levels, the ratio between normalized RNP and guide values was taken to allow comparison of RNP-based repression across different guides. All experiments were conducted in triplicate, and all graphing and quantitative analyses were conducted in Prism. Guide and target sequences can be found in FIG. 18D-18E.

Example 3: Cas9 Catalyzes PAM-Independent RNA-Guided RNA Cleavage

To assess whether divergent Cas9 enzymes can catalyze binding to and cleavage of RNA substrates by a mechanism distinct from that of double-stranded DNA cleavage, we tested homologs from the three major subtypes of Cas9 proteins for their ability to cleave single-stranded RNA in vitro (FIG. 3A-3B and FIG. 4A-4D). When programmed with a cognate sgRNA, S. aureus Cas9 (SauCas9) and C. jejuni Cas9 (CjeCas9) directed cleavage of RNA in the absence of a PAMmer (FIG. 3A-3D and FIG. 4B-4D). No RNA cleavage was detected using SpyCas9, which requires a PAMmer for efficient RNA cleavage in vitro (see, e.g., O'Connell M R et al., Nature 2014; 516(7530):263-6), or using F. novicida Cas9 (FnoCas9). While the cleavage efficiencies for both SauCas9 and CjeCas9 were indistinguishable (FIG. 4D), we initially focused on the activity of SauCas9 due to the abundance of mechanistic and structural data for this enzyme (see, e.g., Nishimasu H et al., "Crystal structure of Staphylococcus aureus Cas9," Cell 2015; 162 (5):1113-26; Friedland A E et al., "Characterization of Staphylococcus aureus Cas9: a smaller Cas9 for all-in-one adeno-associated virus delivery and paired nickase applications," Genome Biol. 2015; 16:257 (10 pp.); Ran F A et al., "In vivo genome editing using Staphylococcus aureus Cas9," Nature 2015; 520(7546):186-91; and Kleinstiver B P et al., "Broadening the targeting range of Staphylococcus aureus CRISPR-Cas9 by modifying PAM recognition," Nat. Biotechnol. 2015; 33(12):1293-8).

Figure 5A:
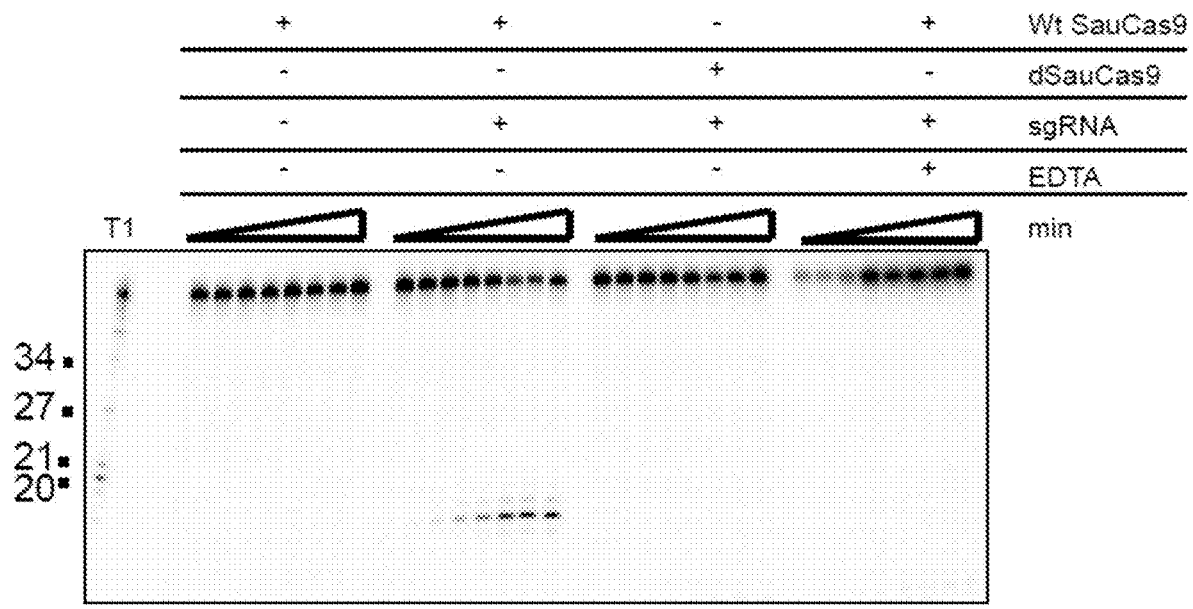
FIG. 5A-5E shows that ssRNA cleavage is similar to canonical dsDNA cleavage by Cas9. In vitro SauCas9 cleavage assay of ssRNA (FIG. 5A). Reactions were incubated with wild-type SauCas9 (Wt SauCas9) or catalytically-inactive SauCas9 (dSauCas9; D10A and N580A) in the presence or absence of sgRNA as indicated above the reactions. EDTA was included at 25 mM where applicable. Under tested conditions, SauCas9 ssRNA cleavage was single-turnover (FIG. 5B). SauCas9 RNP was incubated with the RNA target in the various ratios indicated. Time points are 0, 1, 2, 5, 10, 30, 60, and 120 mins in FIG. 5A-5B. T1 RNase digest size fragments are given on the left. Target used for cleavage was the pUC ssRNA. Graphical representation of ssRNA fraction cleaved (FIG. 5C) of reactions in FIG. 5B. Fit was determined in Prism using a single-exponential decay model. Error bars represent the mean±S.D. (n=3). Mapping of SauCas9 ssRNA cleavage site (FIG. 5D). Reaction products from a 2-hr incubation of SauCas9 RNP with the pUC ssRNA target were separated on a 15% denaturing PAGE gel with a hydrolysis and T1 digest ladder to determine exact site of the major cleavage product. Diagram of canonical DNA cleavage position and ssRNA cleavage position (FIG. 5E) as determined in FIG. 5D for the target (SEQ ID NO:12) in reference to the exemplary sgRNA (SEQ ID NO:303).
Figure 5B:
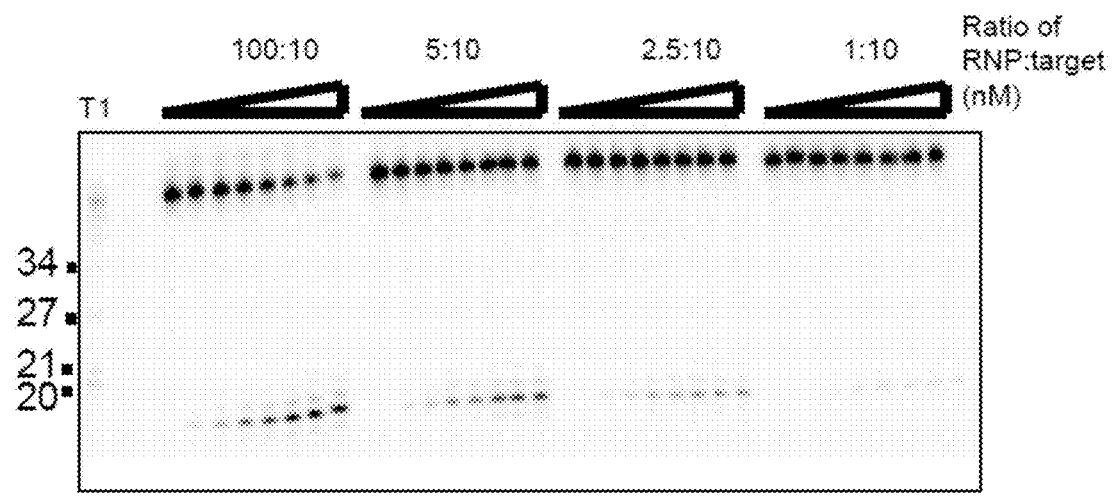
Figure 5C:
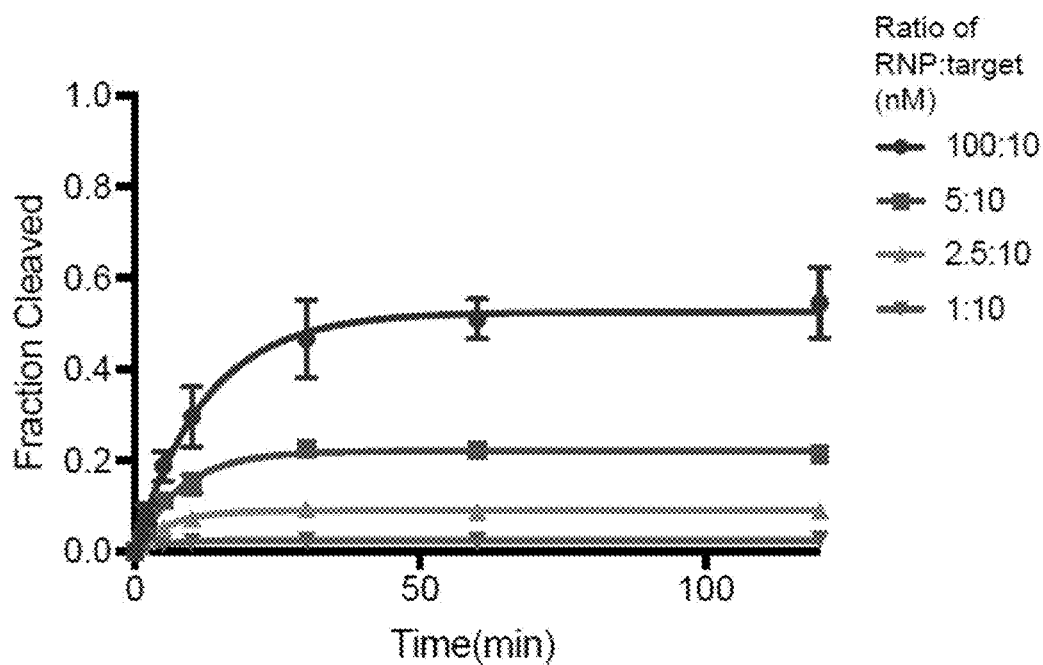

RNA cleavage activity and products were similar to those of canonical Cas9- mediated DNA cleavage activity in vitro. RNA targeting by SauCas9 requires the presence of a guide RNA and a catalytically-active protein, as both apo protein lacking the guide RNA and a catalytically inactive mutant (D10A and N580A) do not cleave RNA (FIG. 5A). Furthermore, addition of EDTA to chelate divalent metal ions abolished RNA cleavage, verifying that divalent metal ions are necessary for catalysis. As with DNA substrates (see, e.g., Sternberg S H et al., "DNA interrogation by the CRISPR RNA-guided endonuclease Cas9," Nature 2014; 507(7490):62-7), incubation of SauCas9 with an excess of RNA target demonstrated that cleavage is single-turnover (FIG. 5B-5C).

Figure 5D:
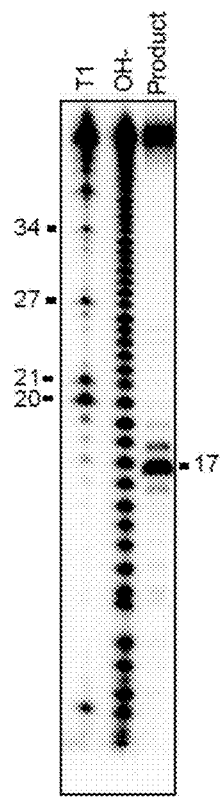
Figure 5E:
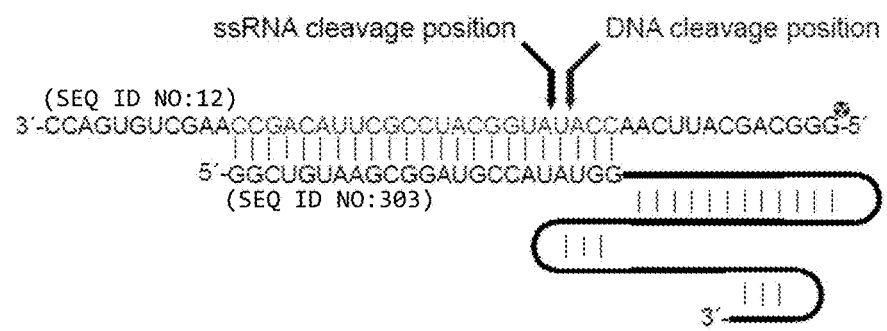
Figure 6A:
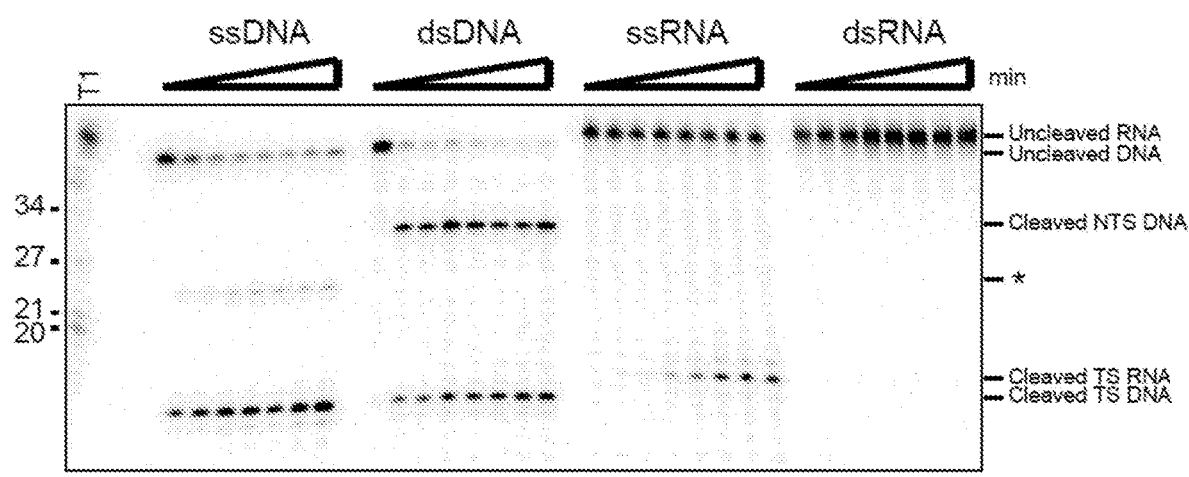
FIG. 6A-6D shows SauCas9 cleavage of different nucleic acid substrates. Representative cleavage assay of nucleic acid substrates (FIG. 6A, 6D) diagramed in FIG. 6B by SauCas9. Asterisk denotes an off-target cleavage site. Time points are 0, 1, 2, 5, 10, 30, 60, and 120 mins. T1 RNase digest size fragments are given on the left. Quantification (FIG. 6C) of results in FIG. 6A, 6D. Fit was determined in Prism using a single-exponential decay model. Error bars represent the mean±S.D. (n=3). Apparent pseudo-first order rate constant ($k_{cleave}$±S.D.) is given to the right of the substrate legend. "N.D." indicates that an accurate rate cannot be determined due to the reaction reaching completion before the second time point; and "n.s." indicates not significant.
Figure 6D:
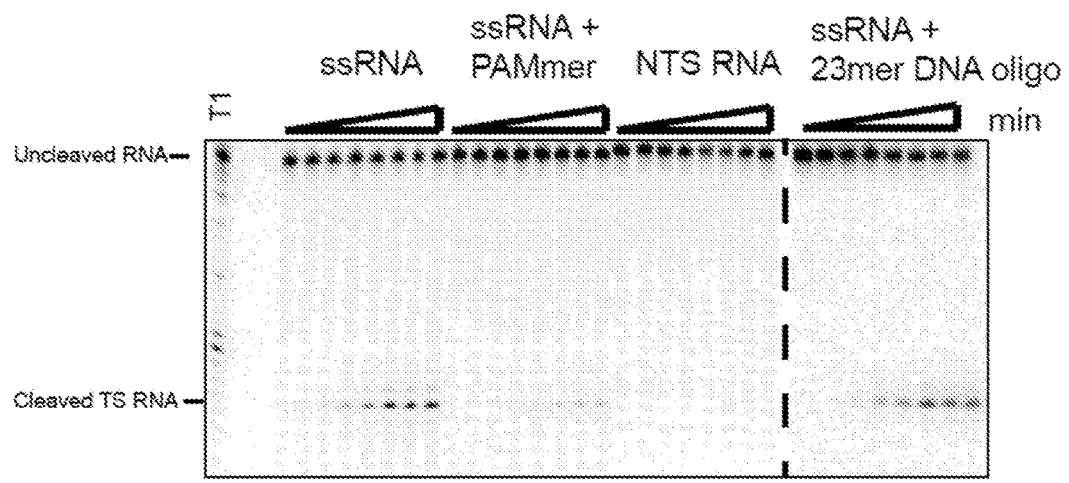
Figure 6B:
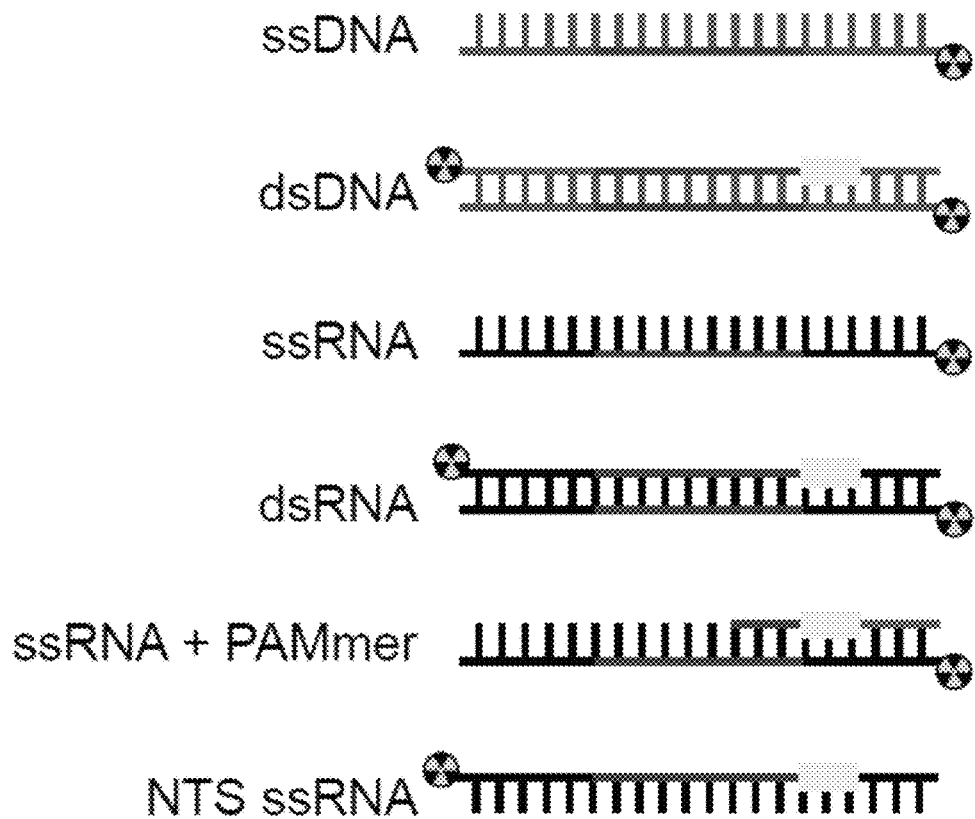
Figure 6C:
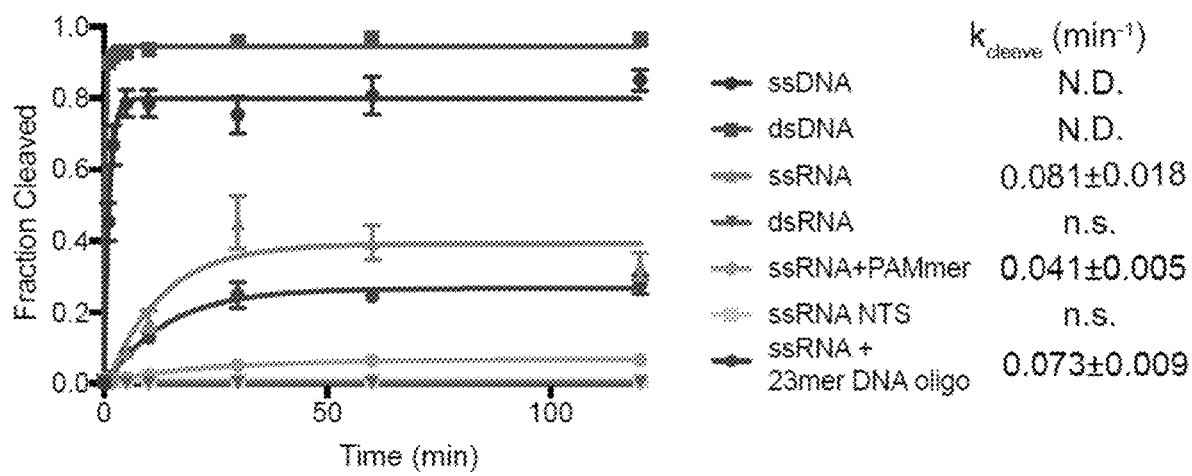

Hydrolysis mapping of the cleavage product revealed that the predominant RNA cleavage site is shifted by one nucleotide compared to the site of DNA cleavage (see, e.g., Garneau J E et al., "The CRISPR/Cas bacterial immune system cleaves bacteriophage and plasmid DNA," Nature 2010; 468(7320):67-71; Jinek M et al., Science 2012; 337 (6096):816-21; and Gasiunas G et al., Proc. Nat'l Acad. Sci. USA 2012; 109(39):E2579-86) (FIG. 5D-5E). The shift is consistent with that observed for PAM-dependent SpyCas9 RNA-cleavage. Without wishing to be limited by mechanism, this shift is likely due to the more compact geometry of an RNA-RNA helix relative to an RNA-DNA hybrid helix (see, e.g., O'Connell M R et al., Nature 2014; 516(7530): 263-6; and Wang A H et al., "Molecular structure of r(GCG) d(TATACGC): a DNA-RNA hybrid helix joined to double helical DNA," Nature 1982; 299(5884):601-4).

SauCas9 targets ssRNA in the absence of a PAMmer, a contrast to SpyCas9 targeting of ssRNA (see, e.g., O'Connell M R et al., Nature 2014; 516(7530):263-6). Testing SauCas9 in vitro ssRNA cleavage in the presence of a PAMmer (30× molar excess over ssRNA target) revealed that turnover was two-fold slower than the reaction with only target ssRNA (FIG. 3C and FIG. 6A-6D). SauCas9 ssRNA cleavage conducted in the presence of a non-complementary, control DNA oligo did not yield a similar reduction in cleavage rate (FIG. 6C), indicating that the complementary PAMmer impairs RNA cleavage activity. Consistent with cleavage being guide-dependent, single-stranded RNA that is not complementary to the sgRNA was not cleaved (FIG. 3C-3D and FIG. 6A-6D). Double-stranded RNA (dsRNA) was also not a substrate for SauCas9.

Figure 7D:
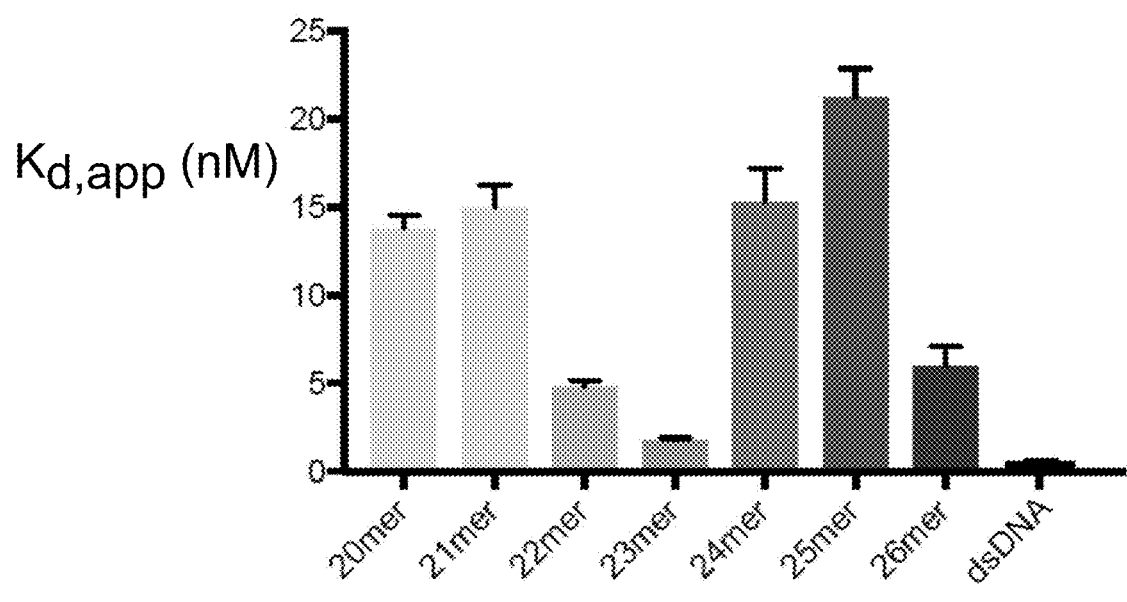

Given that Cas9 proteins are active with different length guide RNA segments (~20-24 nt) (see, e.g., Chylinski K et al., "The tracrRNA and Cas9 families of type II CRISPR-Cas immunity systems," RNA Biol. 2013; 10(5):726-37; Ran F A et al., Nature 2015; 520(7546):186-91; Friedland A E et al., Genome Biol. 2015; 16:257 (10 pp.); and Kim E et al., "In vivo genome editing with a small Cas9 orthologue derived from Campylobacter jejuni," Nat. Commun. 2017; 8:14500 (12 pp.)), we tested whether longer guide segments might enhance ssRNA targeting activity. Increasing the length of the targeting region of the guide up to 23 nt results in tighter binding and more efficient cleavage (FIG. 7A-7D), mirroring the preference for longer guides for DNA cleavage (see, e.g., Ran F A et al., Nature 2015; 520(7546):186-91; Friedland A E et al., Genome Biol. 2015; 16:257 (10 pp.)). Extending the guide strand complementarity to the target beyond 23 nt did not increase RNA target binding or cleavage efficiency, indicating that 23 nt is the optimal length for in vitro binding and targeting applications. The apparent dissociation constant ($K_{d,app}$) of the SauCas9-sgRNA complex (23 nt targeting region) for the ssRNA target was 1.8±0.09 nM (FIG. 7D), which is ~5× weaker than the 0.34±0.03 nM binding affinity measured for a dsDNA substrate of the same sequence.

Example 4: Cleavage Efficiency is Impaired by Duplex Regions in Target RNA

We noted that SauCas9-catalyzed ssRNA cleavage is limited to ~30% fraction cleaved (see FIG. 6A-6D), compared to >80% fraction cleaved for ssDNA and dsDNA targets. Greater thermodynamic stability of RNA secondary structures, relative to those in ssDNA (see, e.g., Bercy M et al., "Hairpins under tension: RNA versus DNA," *Nucleic Acids Res.* 2015; 43(20):9928-36) might occlude SauCas9-sgRNA binding to an ssRNA target sequence, a possibility that we tested using a panel of partially duplexed RNA substrates (FIG. 8A-8D).

Figure 8A:
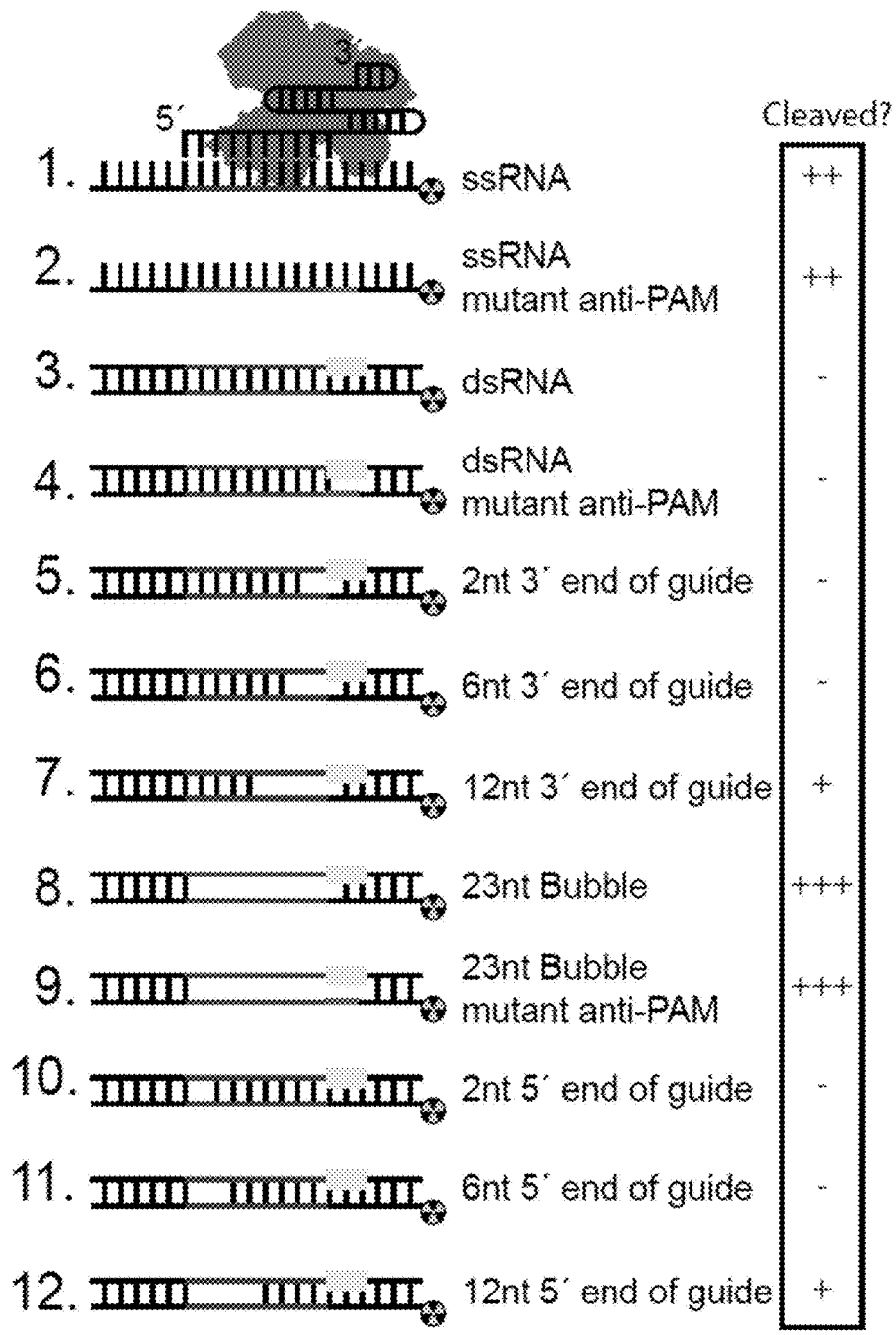
FIG. 8A-8D shows that in vitro RNA cleavage is impaired by strong secondary structure. Schematic representation of structured RNA targets (substrates 1 to 12) for in vitro cleavage assays (FIG. 8A). Symbols on right indicate relative level of cleavage activity for each substrate: no cleavage (−); low level of cleavage (+); medium level of cleavage (++); and high level of cleavage (+++). Representative cleavage assay (FIG. 8B) of partially-duplexed RNA targets diagrammed in FIG. 8A. T1 indicates size markers generated by RNase T1 digestion of ssRNA target. Size in nucleotides is indicated on the left. Fraction of target cleaved (FIG. 8C) and $K_{d,app}$ (FIG. 8D) for substrates diagrammed in FIG. 8A. Fits were determined in Prism using a single-exponential decay and a one-site binding model, respectively. Bars represent mean±S.D. (n=3); and "n.s." denotes no significant cleavage or binding.
Figure 8B:
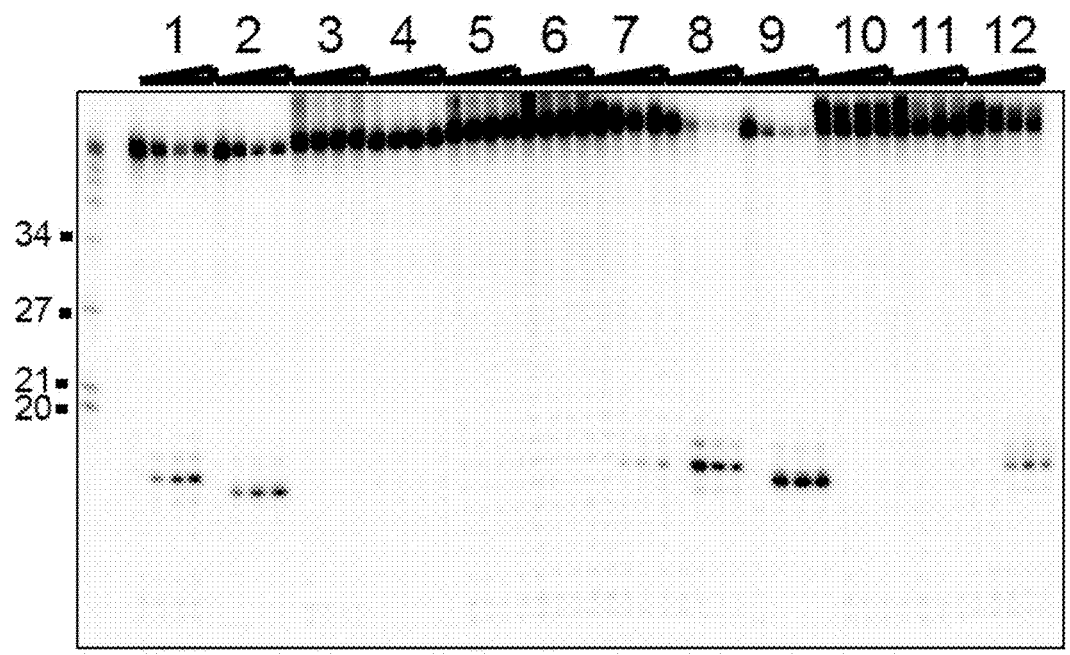

Previously, introduction of a short segment of mismatched base pairs to mimic partially unwound dsDNA substrates was shown to enhance the ability of type II-C Cas9s (including CjeCas9) to unwind and cleave dsDNA (see, e.g., Ma E et al., *Mol. Cell* 2015 Nov. 5; 60(3):398-407). Here, we found that RNA substrates containing a 2- or 6-base pair mismatched segment located near the 5' or 3' end of the 23 nt guide RNA region of the sgRNA could not be cleaved (FIG. 8A-8C, data for substrates 5, 6, 10, and 11). However, when the unpaired region was increased to 12-base pairs, SauCas9 was able to cleave the target strand. There was a slight cleavage preference for RNA substrates in which the 12-base pair mismatched segment is located near the 5' end of the guide sequence of the sgRNA (FIG. 8A-8C, data for substrates 7 and 12).

Figure 8C:
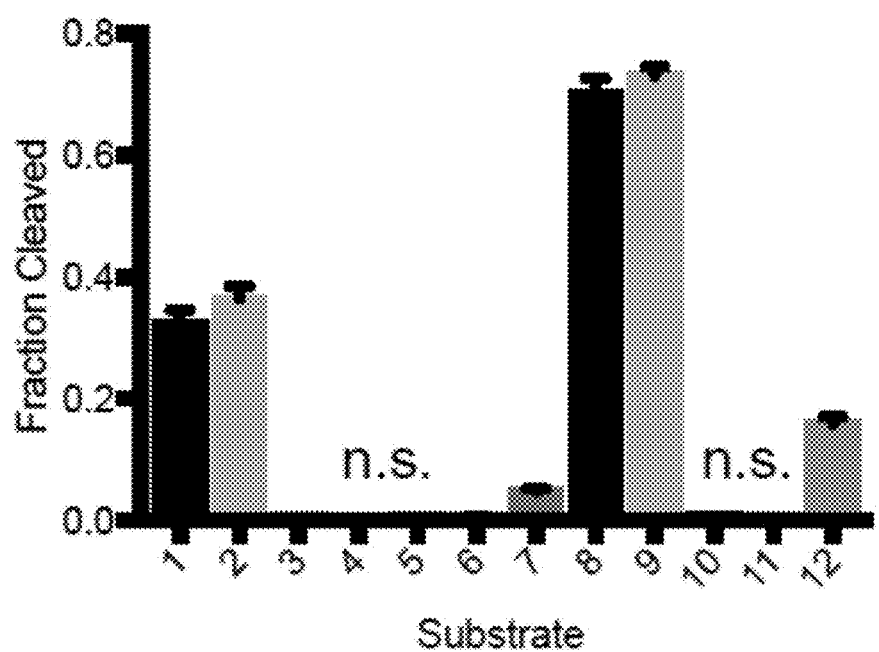
Figure 8D:
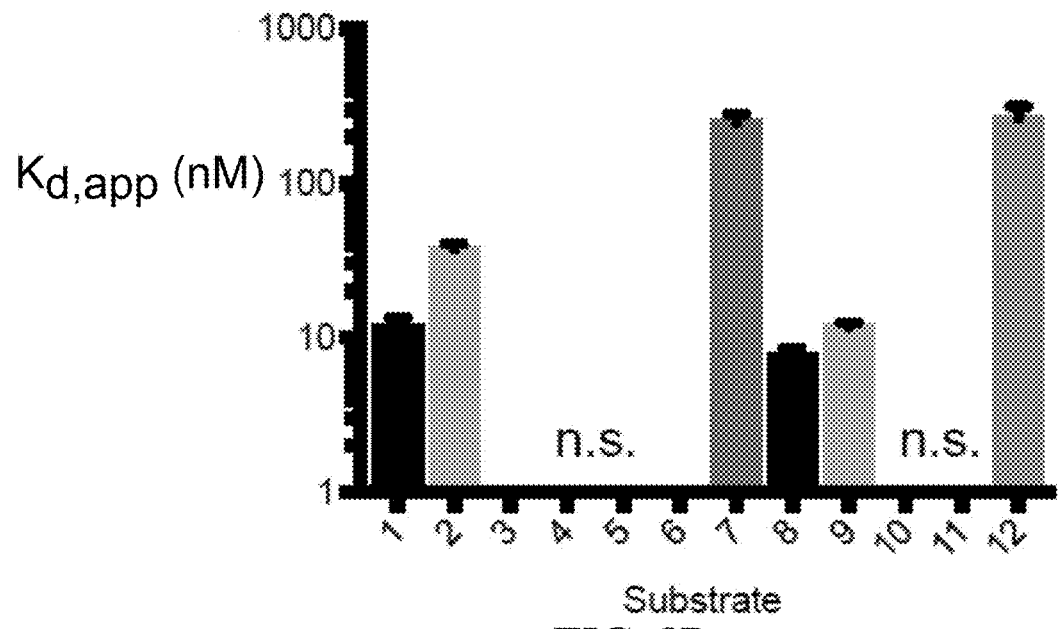
Figure 9A:
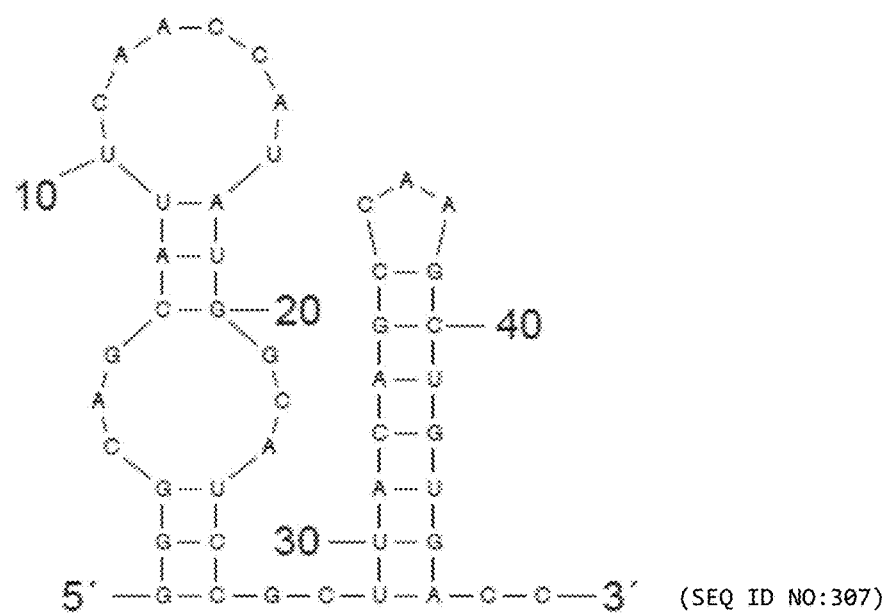
FIG. 9A-9E shows that RNA cleavage can be limited by the RNA target. Predicted secondary structure of target RNA used in this study (SEQ ID NO:307) (FIG. 9A). In vitro cleavage assay of ssRNA with SauCas9 was conducted for 2 hr (time points: 0, 1, 2, 5, 10, 30, 60, 120 mins) (FIG. 9B). The reaction was split, and SauCas9-sgRNA RNP or apo SauCas9 were added. The reaction was further incubated at 37° C., and data at additional time points were taken to check for additional cleavage of the target. Time points were taken at 0, 1, 2, 5, 10, 30, 60, and 120 mins post-RNP/apo SauCas9 addition. Fit (FIG. 9C) for data in FIG. 9B was determined in Prism using a single-exponential decay model. Error bars represent the mean±S.D. (n=3). In vitro cleavage assay of two ssRNA targets added sequentially (FIG. 9D). After 60 min incubation of SauCas9 with the pUC target, another target containing either the same recognition sequence (ON target—Reaction 1) or an unrelated sequence (OFF target—Reaction 2) were added to the reaction. Cleavage was assayed for an additional 60 mins (time points: 0, 10, 30, 60 min). Reactions containing only the second target (Reactions 3 and 4) were conducted with SauCas9 RNP that was incubated for 60 min at 37° C. prior to addition to the cleavage reaction. Quantification (FIG. 9E) of cleavage of second target in FIG. 9D for time points after addition. Fit was determined in Prism using a single-exponential decay model. Error bars represent the mean±S.D. (n=3).

Interestingly, the 23-base pair mismatched segment RNA substrates ('Bubble' substrates 8 and 9) are targeted more efficiently than their ssRNA counterparts (substrates 1 and 2) (FIG. 8C). We measured the binding affinity of all substrates and found that both the 23-base pair mismatched segment RNA and ssRNA substrates are bound with similar affinity (FIG. 8D). Furthermore, the apparent difference in cleavage efficiency was not due to the presence of a double-stranded PAM sequence, as mutating the PAM region does not impair cleavage (FIG. 8C, compare substrates 8 and 9). We hypothesize that RNA containing a mismatched segment presents a more accessible substrate to the Cas9-sgRNA complex due to stable annealing between the ends of the non-target and target strands, whereas the ssRNA substrate alone has ends that are predicted to stabilize a conformation that is partially structured and therefore inaccessible (FIG. 9A).

Figure 9B:
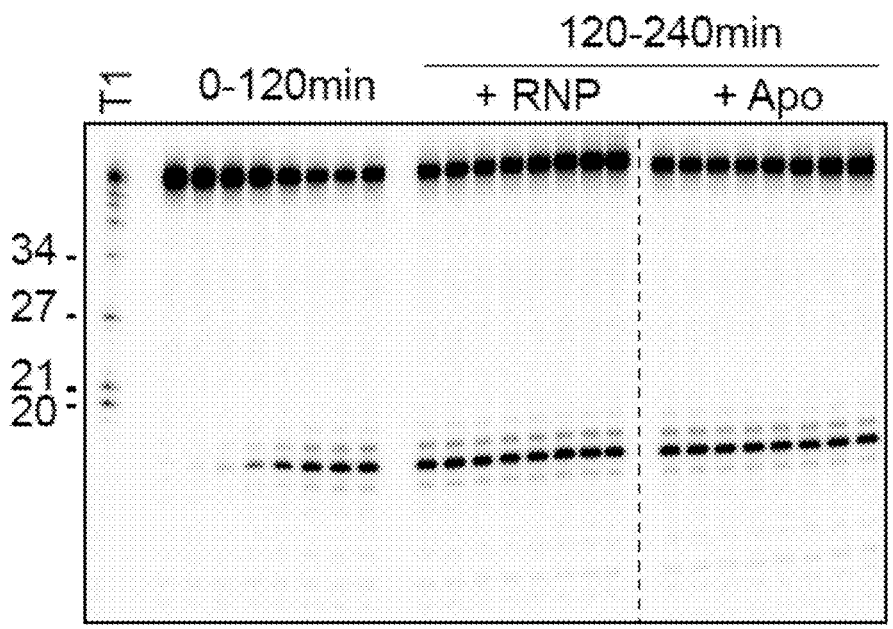
Figure 9C:
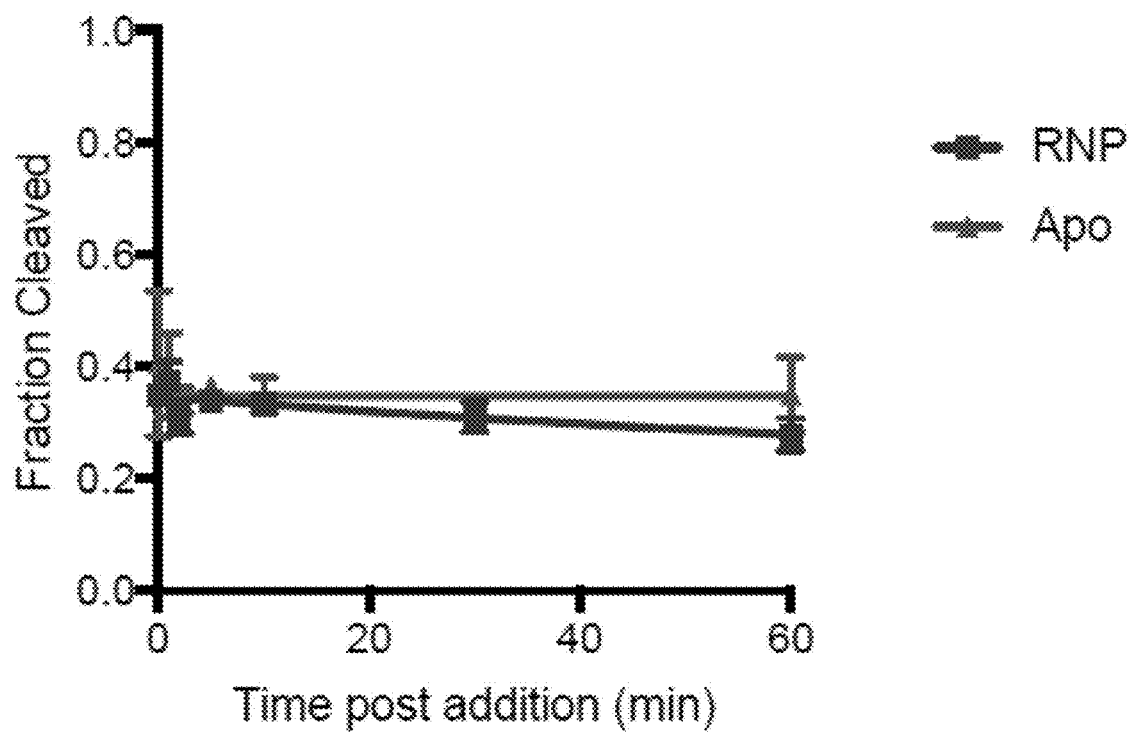
Figure 9D:
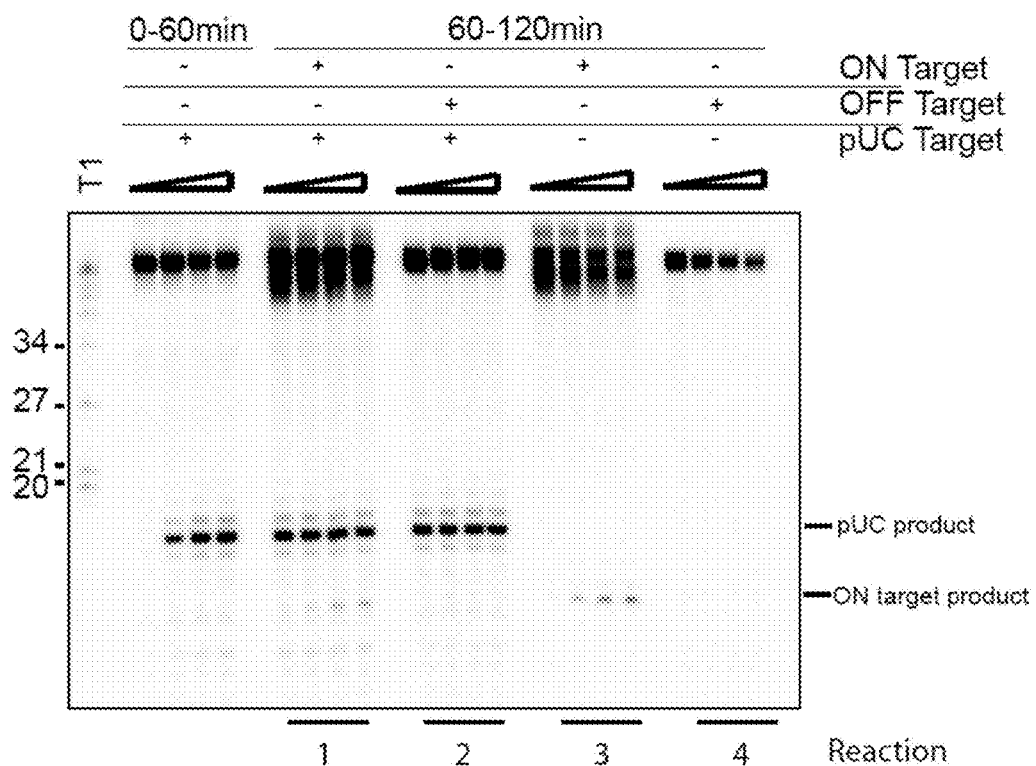
Figure 9E:
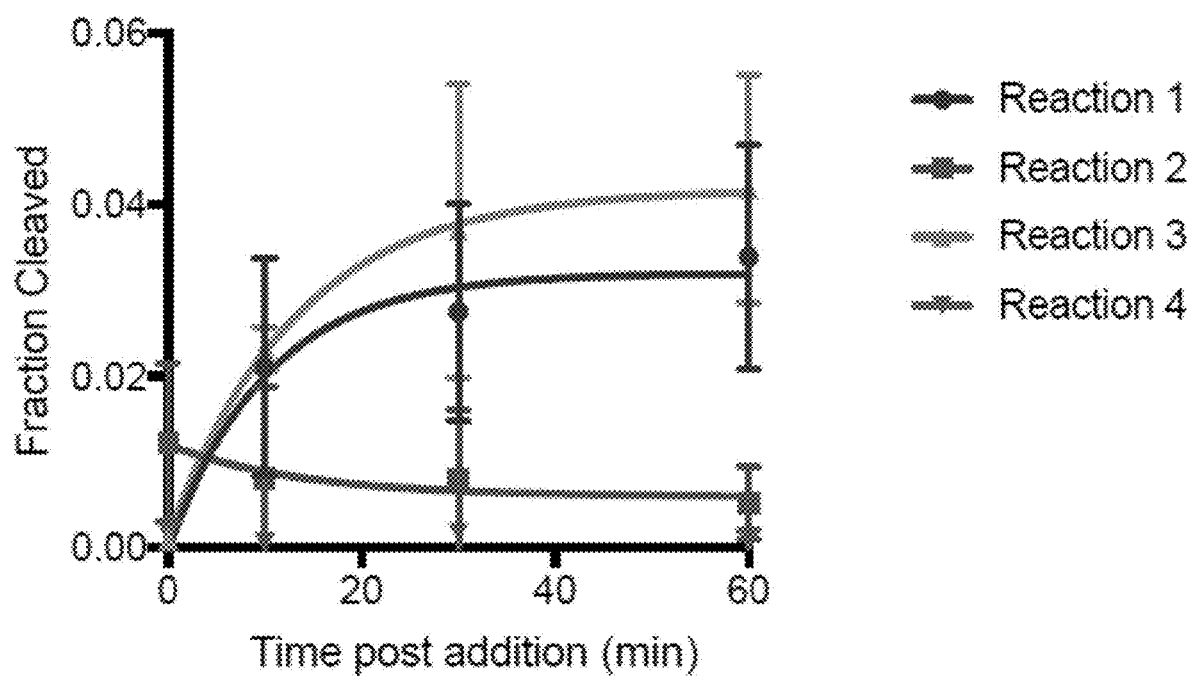

An alternative hypothesis to explain the limited cleavage of ssRNA substrates is that SauCas9 enzyme inactivation occurs over the course of the reaction, even with SauCas9 protein-sgRNA (ribonucleoprotein, RNP) present in 10-fold excess relative to the ssRNA substrate. To test this, we spiked reactions with fresh SauCas9 protein alone or SauCas9 RNP after reactions reached equilibrium; however, we did not observe an increase in the amount of ssRNA cleavage (FIG. 9B-9C). We also tested whether the SauCas9 RNP was able to cleave a second ssRNA substrate that was added to the reaction after it reached completion (FIG. 9D-9E). After 1 hr of incubation, the addition of a second target ssRNA complementary to the guide RNA resulted in a burst of cleavage activity, whereas a non-complementary ssRNA substrate did not stimulate cleavage. The second target ssRNA was cleaved to a comparable extent to that observed when this second target was the only substrate in the reaction (FIG. 9D-9E, compare reactions 1 and 3).

These observations suggest that SauCas9 RNP is still competent and available for cleavage at the end of the reaction and that a property intrinsic to the ssRNA substrate is the limiting factor. We propose that the observed difference in cleavage extents for various RNA substrates reflects the fraction of molecules that are structurally accessible for cleavage by the SauCas9 RNP.

Example 5: SauCas9 Confers In Vivo Protection Against RNA Phage

Figure 10A:
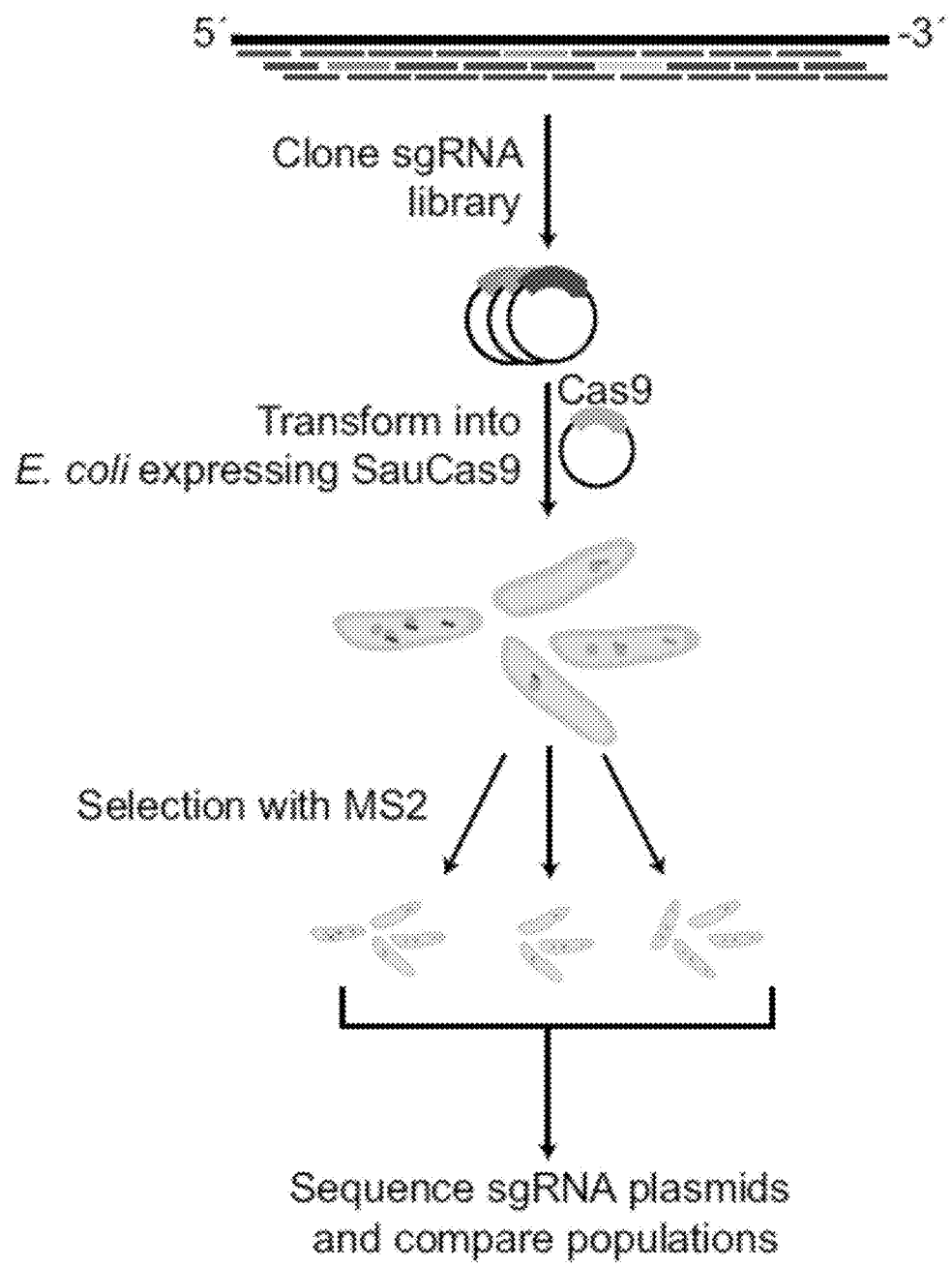
FIG. 10A-10F shows that SauCas9 confers in vivo protection against an RNA phage. Overview of MS2 targeting screen (FIG. 10A). Guides tiled against the library were cloned into sgRNA expression plasmids and co-transformed into E. coli with a plasmid containing wild-type SauCas9 under inducible control. Plasmids from surviving colonies after MS2 selection were recovered and sequenced. For more detail, see Example 2 herein. Number of guides with significant positive enrichment from three biological experiments (FIG. 10B), in which guides included those that were control (Control), perfect complementarity matches (Perfect), or guides with a single-nucleotide (SNP) mismatch. Box and whiskers plot of average $\log_2$ fold-change of perfect MS2 guides by length (FIG. 10C). Whiskers represent 5% and 95% values with outliers graphed as points. *p<0.05, p<0.01, **p<0.0001, by one-way ANOVA. $\log_2$ fold-change plot of guides with an FDR-corrected p-value <0.05 mapped to the MS2 genome for multiplicities of infection (MOI) of 100 (MOI-100) treatment, in which a schematic of MS2 genome is provided above the plot (FIG. 10D, upper). Individual guides mapped to highlighted regions of MS2 genome (FIG. 10D, lower). Other graphs for MOI-10 and MOI-100 treatments are presented FIG. 11A-11D. Representative plaque assay of SauCas9 in vivo protection (FIG. 10E). E. coli containing constructs on the right are spotted with various phage dilutions as indicated. Scr signifies that the targeting portion of the guide has been scrambled to serve as a non-targeting control. Relative plaque forming units (PFU) (mean±S.D., n=3) (FIG. 10F) from results in FIG. 10E. More guides and controls are presented in FIG. 13A-13E.

Based on the biochemical ability of SauCas9 RNP to bind and cleave ssRNA substrates, we wondered whether this activity might provide protection against RNA phage infection in bacteria. To test this, we generated a plasmid library encoding sgRNAs containing guide sequences complementary to the genome of MS2, a single-stranded RNA phage that can infect *E. coli*. A subset of these sgRNAs contained scrambled guide sequences that should not target MS2, providing negative controls. Another sgRNA subset included single-nucleotide mismatches introduced at each position of a target sequence to test for mismatch sensitivity in ssRNA recognition. This plasmid library, comprising 18,114 sgRNAs (SEQ ID NOs:334-18447), was co-transformed into *E. coli* along with a vector encoding a catalytically active version of SauCas9, and the population of transformants was subjected to infection by bacteriophage MS2 (FIG. 10A). The experiment was performed in biological triplicate and included an untreated control population and two experimental conditions (multiplicities of infection (MOIs) of 10 and 100). After selection, plasmids were recovered from surviving colonies and sequenced (FIG. 10A).

Figure 10B:
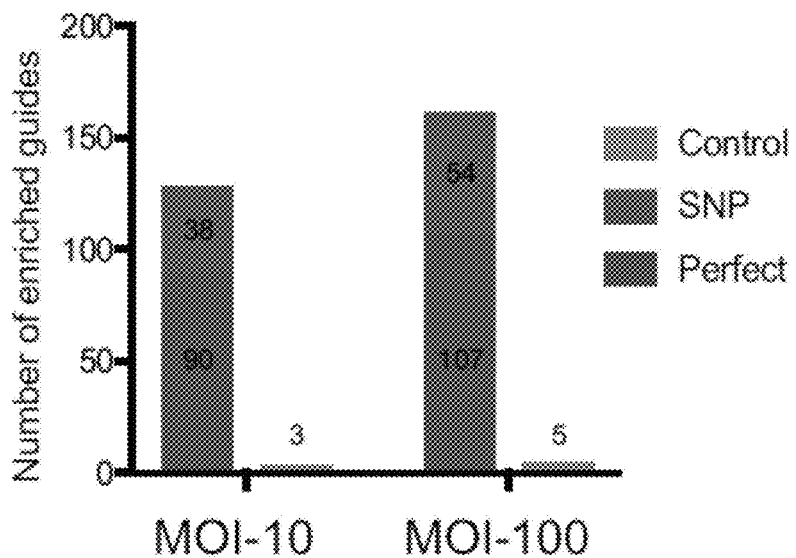

We identified between 131 and 166 sgRNAs that were significantly enriched (false discovery rate (FDR)-adjusted p-value <0.05) in the two different MS2 infection conditions (FIG. 10B). The majority of these sgRNAs were perfectly complementary to the MS2 genome, and only three and five control sgRNAs (out of 708 total control sgRNAs) for the MOI-10 and MOI-100 conditions, respectively, were enriched (FIG. 10B).

The lengths of enriched guide sequences were skewed towards shorter targeting lengths (FIG. 11A, left); however, this likely reflects bias in the cloned input library since the ratio between the enriched guide sequences and those of the library without phage selection are similar (FIG. 11A, right).

Figure 10C:
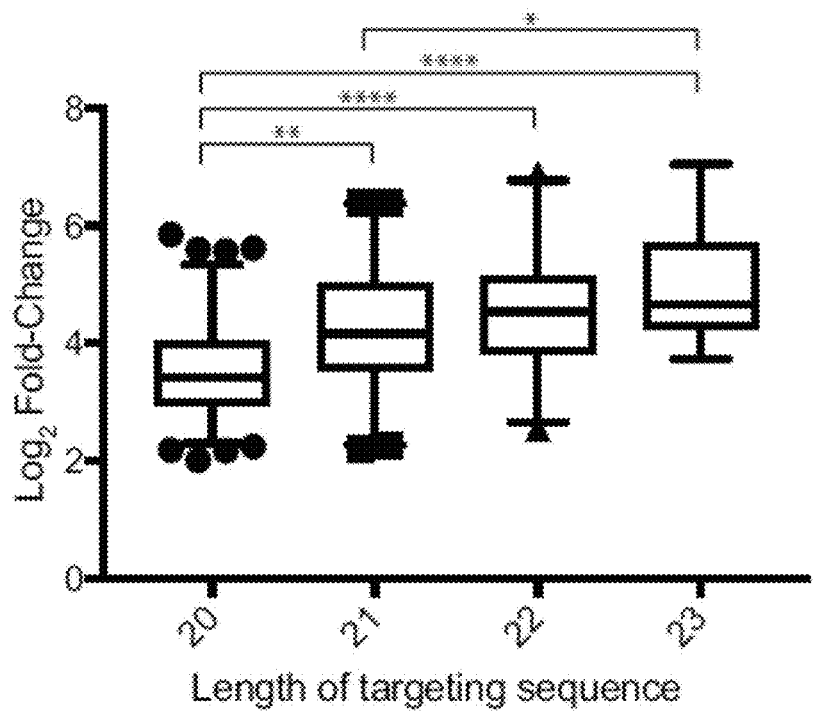

When comparing the degree of enrichment between the different guide lengths, the 23-nt guide segment sgRNAs were preferentially enriched over those of shorter length (FIG. 10C), consistent with the in vitro observation that longer guides are more efficient for directing ssRNA cleavage (see, e.g., FIG. 7C). To assess whether there was any sequence bias within the enriched guides, we aligned guide sequences of all lengths at their 3' end. These alignments showed no specific sequence bias in the enriched guides relative to those in the unselected library (FIG. 11B). This is consistent with the crystal structure of an SauCas9-sgRNA-DNA bound complex which revealed the absence of base-specific contacts of Cas9 to the target strand (see, Nishimasu H et al., *Cell* 2015; 162(5):1113-26; and Nishimasu H et al., "Crystal structure of Cas9 in complex with guide RNA and target DNA," *Cell* 2014; 156(5):935-49).

Figure 10D:
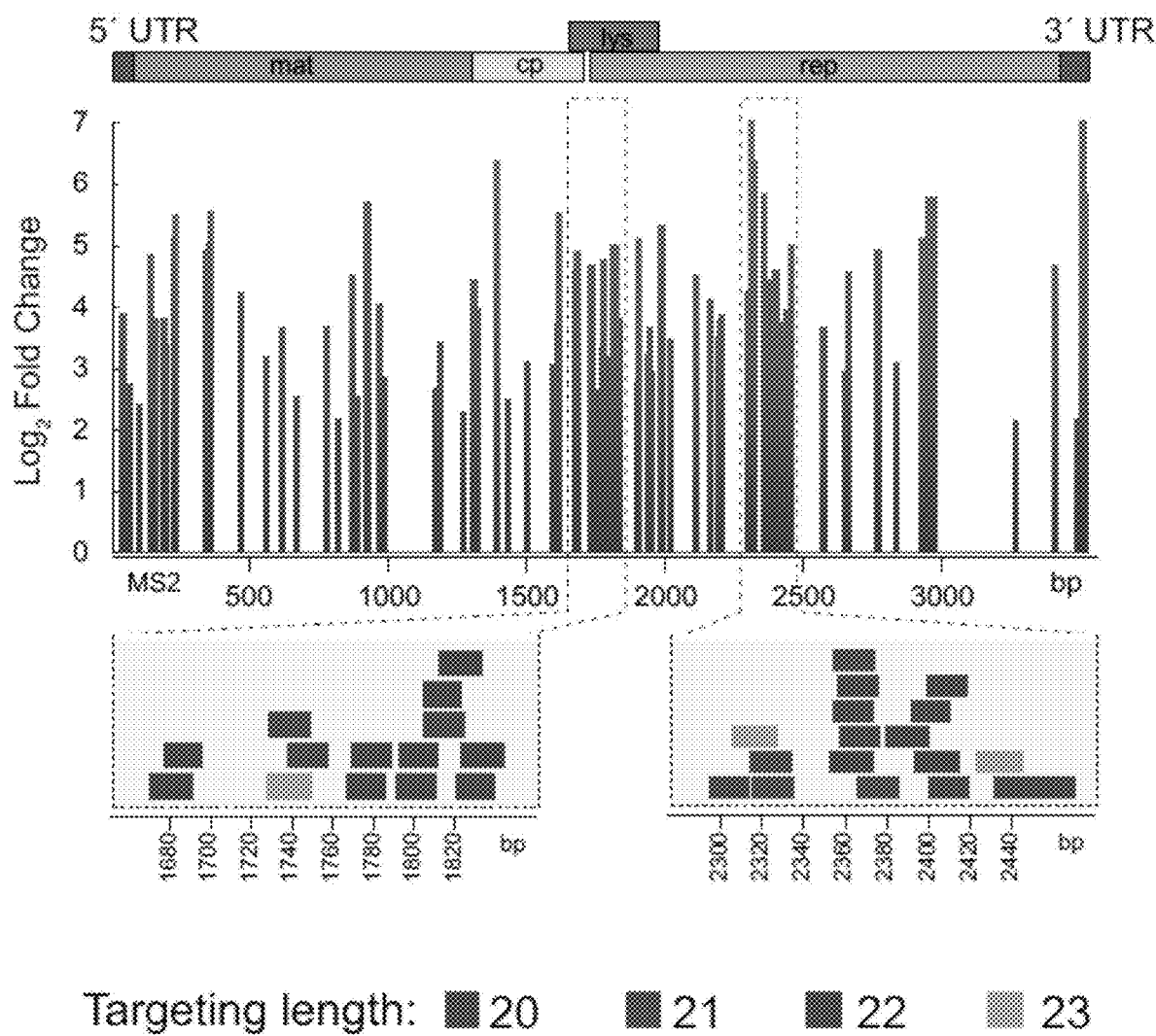

Strikingly, mapping enriched guide sequences onto the MS2 genome showed that enriched sgRNAs were clustered at specific regions, which were consistent across both experimental conditions (FIG. 10D and FIG. 11C-11D). Together with our biochemical data suggesting that SauCas9 cannot bind or cleave structured RNAs (see, FIG. 10A-10F), we interpret these targeting "hotspots" to be regions of low structural complexity. It is important to note that sgRNAs containing different guide segment lengths overlap at these regions, possibly indicating that increases in targeting efficiency due to guide length are secondary to target accessibility to the Cas9 RNP. We mapped the enriched guide sequences onto the published secondary structure of the MS2 genome determined through cryoelectron microscopy (see, e.g., Dai X et al., *Nature* 2017; 541(7635):112-6) (FIG. 12). Guides targeted not only single-stranded, accessible regions but also those that form apparently stable secondary structures. The structure of the MS2 genome was determined on the intact phage particle, however, and may not represent the RNA structure(s) relevant to the infection stage during which SauCas9-mediated protection is crucial.

Figure 10E:
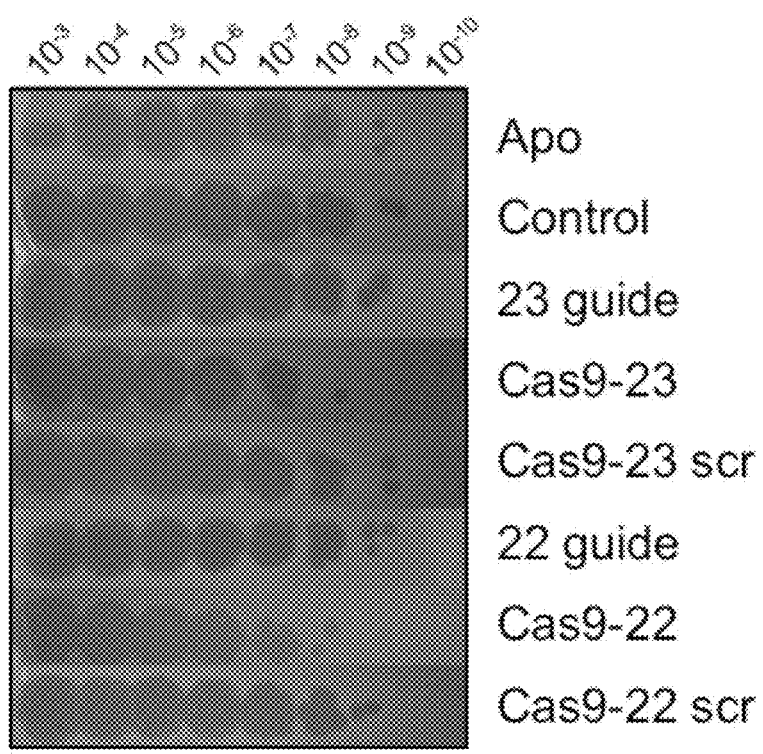
Figure 10F:
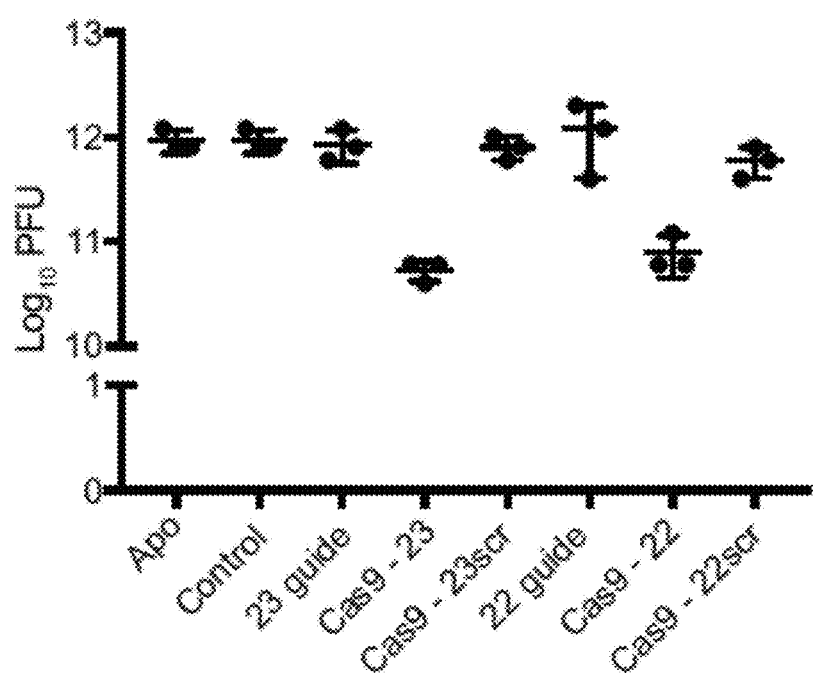

Highly enriched sgRNAs from the screen were confirmed for their ability to confer protection against MS2 phage infection through a soft-agar plaque assay. Reconstitution of SauCas9 with a targeting guide confers approximately a ten-fold protection against the RNA phage (FIG. 10E-10F). No protection was observed in the absence of an sgRNA or SauCas9 protein. Scrambling the sequence of the guide also abrogates protection, confirming that sequence complementary is necessary for phage elimination.

Guide segments of all lengths tested (20-23 nts) conferred protection to a similar level (FIG. 13A,13C), consistent with the result from the MS2 screen that guide segments of all lengths were enriched in 'hotspot' regions (FIG. 10D). Two 'control' guides were enriched in both the MOI-10 and MOI-100 treatments. Interestingly, both guides conferred protection but their scrambled counterparts did not (FIG. 13B,13D). Whereas a possible off-target binding site was found for one guide (#14238, SEQ ID NOs:308, 309, and 14571) within the MS2 genome (FIG. 13E), it remains unclear how guide #14210 (SEQ ID NO:14543) confers protection. Without wishing to be limited by theory, possibly this sgRNA acts by targeting an *E. coli* host factor that is necessary for infection.

Screening against the MS2 genome was also used to test the effect of single-nucleotide mismatches on SauCas9's targeting ability. We computed an average fold change (between phage treated and untreated samples) for all sgRNAs that contained a mismatch at the same position, and obtained average values for mismatches at each position across the guide. We observed a pronounced gradient of increasing guide stringency with length. On average, short guides were less sensitive to mismatches, while mismatches in longer sgRNAs led to decreased recovery compared to control samples (FIG. 14A-14B).

Previous work and models suggest that shorter guide segments should be more sensitive to mismatches and lead to higher fidelity Cas9 targeting (Fu Y et al., "Improving CRISPR-Cas nuclease specificity using truncated guide RNAs," *Nat. Biotechnol.* 2014; 32(3):279-84; and Bisaria N et al., "Lessons from enzyme kinetics reveal specificity principles for RNA-guided nucleases in RNA interference and CRISPR-based genome editing," *Cell Syst.* 2017; 4(1): 21-9). Further study could elucidate further insights into this unexpected pattern of RNA-targeting stringency, as one shortcoming of this experiment is that mismatched guides were not designed a priori to recognize accessible parts of the MS2 genome.

Figure 14D:
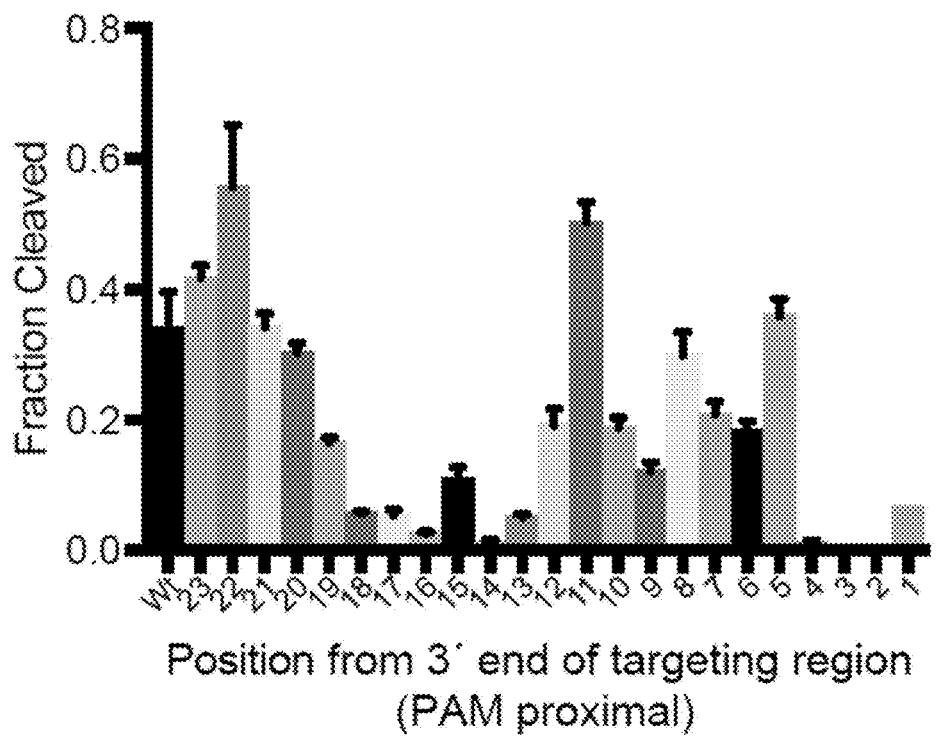

Nevertheless, despite potential noise introduced in this analysis due to guide segments that target inaccessible MS2 regions, we observe an interesting correlation between mismatches in the MS2 screen and in vitro biochemical cleavage assays for the sgRNA with a 23 nt guide segment sequence (FIG. 14C-14D). The first few nucleotides in the 'seed' region (guide 3' end proximal) are sensitive to mismatches, while a central region of sensitivity is also observed, similar to previously demonstrated regions of sensitivity for SpyCas9 DNA cleavage (Cong L et al., "Multiplex genome engineering using CRISPR/Cas systems," *Science* 2013; 339(6121):819-23; Jiang W et al., "RNA-guided editing of bacterial genomes using CRISPR-Cas systems," *Nat. Biotechnol.* 2013; 31(3):233-9; Fu B X et al., "Distinct patterns of Cas9 mismatch tolerance in vitro and in vivo," *Nucleic Acids Res.* 2016; 44(11):5365-77; and Gorski S A et al., "RNA-based recognition and targeting: sowing the seeds of specificity," Nat. Rev. *Mol. Cell Biol.*

Example 6: SauCas9 Represses mRNA Translation in *E. coli*

An efficient RNA-targeting Cas9 could serve as an important tool in regulating gene expression in vivo. To test the ability of SauCas9 to mediate repression of host gene translation, we targeted dSauCas9 and dSpyCas9 RNPs to a GFP reporter sequence encoded in the *E. coli* chromosome (see, e.g., Qi L S et al., "Repurposing CRISPR as an RNA-guided platform for sequence-specific control of gene expression," *Cell* 2013; 152(5):1173-83). Catalytically inactive versions of Cas9 were used to prevent cleavage of the bacterial chromosome when targeting a site adjacent to a PAM. As expression of Cas9 and sgRNA exerts metabolic stress on *E. coli*, GFP fluorescence values were normalized by the $OD_{600}$ value to account for differences in cell growth between cultures (see, e.g., Oakes B L et al., "Profiling of engineering hotspots identifies an allosteric CRISPR-Cas9 switch," *Nat. Biotechnol.* 2016; 34(6):646-51).

When using sgRNAs designed to recognize a sequence in the GFP gene adjacent to the appropriate PAM for SauCas9 (NNGRRT) or SpyCas9 (NGG), GFP expression was significantly reduced (FIG. 15A) consistent with CRISPR-interference (CRISPRi) (see, e.g., Qi L S et al., *Cell* 2013; 152(5):1173-83; and Gilbert L A et al., "Genome-scale CRISPR-mediated control of gene repression and activation," *Cell* 2014; 159(3):647-61). When sgRNAs were designed to recognize GFP sequences not flanked by a PAM, dSauCas9 but not dSpyCas9 was able to repress GFP expression. The SauCas9-mediated GFP repression was dependent on sgRNAs that target the coding strand; sgRNAs that recognize the non-coding strand did not result in reduced GFP expression (FIG. 16A). The length of the targeting sequence in vivo corroborates in vitro data, with longer guides working more efficiently (FIG. 15B).

Different guide sequences displayed variable efficiencies of targeting. We tiled sgRNAs across the GFP mRNA sequence to test the robustness of dSauCas9 to repress GFP expression (FIG. 15C). As no sites were adjacent to PAM sequences, all repression should occur on the translational level. The efficiency of dSauCas9-mediated GFP repression varied according to the target sequence, with some dSauCas9 RNPs reducing GFP signal to 15-30% of that observed in the presence of the sgRNA alone (FIG. 15C, data for substrates GFP2 and GFP6) and others showing no ability to repress GFP expression (FIG. 15C, data for substrates GFP7 and GFP9).

Electrophoretic mobility shift assays support the conclusion that repression was not occurring at the dsDNA level by promiscuous PAM binding (FIG. 16B). Repression was largely equivalent between catalytically active and inactive forms of SauCas9 (FIG. 16C), suggesting that binding of the Cas9-sgRNA complex to the mRNA was sufficient for repression. This understanding is consistent with in vitro data showing that the enzyme does not catalyze multiple-turnover RNA cleavage.

Together our biochemical and in vivo data support a model in which SauCas9 can readily bind and cleave bacteriophage RNA and mRNA sequences that are exposed and unstructured (FIG. 15D). Regions that form strong structures are relatively inaccessible to SauCas9 RNP binding, thereby preventing cleavage or repression activity in the studies described herein. Without wishing to be limited by theory, as Cas9 cleavage activity can be limited by target accessibility, we expect that RNA occluded by RNA-binding proteins may also be recalcitrant to cleavage.

Example 7: Potential Applications for RNA-Targeting CRISPR-Cas Systems

Prior investigations of CRISPR-Cas9 has generally focused on its function as a double-stranded DNA endonuclease, while the ability of diverse homologs to cleave natural RNA substrates has remained unexplored. Here, we present evidence that type II-A and type II-C Cas9 enzymes can catalyze programmable and PAM-independent single-stranded RNA cleavage. Focusing on SauCas9, we show that this enzyme can be employed both biochemically and in cells to cleave RNA and to regulate genes on both the transcriptional and translational level in parallel by accounting for target site PAM proximity.

Importantly, SauCas9 ssRNA scission requires only a sgRNA and does not need a PAMmer, thereby simplifying applications (see, e.g., Nelles D A et al., "Applications of Cas9 as an RNA-programmed RNA-binding protein," *Bioessays* 2015; 37(7):732-9) and facilitating delivery to cells as a pre-assembled RNP (see, e.g., Zuris J A et al., "Cationic lipid-mediated delivery of proteins enables efficient protein-based genome editing in vitro and in vivo," *Nat. Biotechnol.* 2015; 33(1):73-80; and Mout R et al., "Direct cytosolic delivery of CRISPR/Cas9-ribonucleoprotein for efficient gene editing," *ACS Nano* 2017; 11(3):2452-8).

The RNA-targeting capability of SauCas9 and related Cas9 enzymes offers the advantage of repressing viruses whose lifecycles do not involve a DNA genome or intermediate, thereby rendering them inaccessible to Cas9-mediated DNA cleavage. We demonstrated that SauCas9 could be programmed to confer protection to *E. coli* against MS2, an RNA bacteriophage with no DNA intermediate. Whether RNA-based viral repression by Cas9 occurs in natural systems is not known, but seems possible based on our results.

Intriguingly, 'hotspots' of preferential targeting emerged when tiling guides across the genome, but these sites were devoid of sequence bias. In conjunction with in vitro cleavage data of partially structured RNAs, we suggest that SauCas9 cleavage efficiency is inversely related to structural complexity of the RNA target. As an alternative to the current approach of screening multiple sgRNAs for activity, experimental knowledge about RNA structure, such as SHAPE-seq data (see, e.g., Loughrey D et al., "SHAPE-Seq 2.0: systematic optimization and extension of high-throughput chemical probing of RNA secondary structure with next generation sequencing," *Nucleic Acids Res.* 2014; 42(21): e165 (10 pp.)), could simplify target identification for viral targeting and repression experiments. Nevertheless, future work could concentrate on understanding the structural constraints on RNA targeting and methods to improve Cas9 access to duplex RNA regions.

SauCas9 holds promise for a range of RNA targeting applications. We showed that SauCas9 could repress mRNA translation in *E. coli*. Repression of the reporter occurred in the absence of the PAM and was specific for targeting of the coding strand. A programmable Cas9 capable of repressing genes on the RNA level has potential advantages over CRISPRi DNA-based techniques (see, e.g., Qi L S et al., *Cell* 2013; 152(5):1173-83; and Gilbert L A et al., *Cell* 2014; 159(3):647-61). For example, isoform-specific targeting of different transcripts originating from the same transcription start site or resulting from alternative splicing events might be possible. More broadly, due to its intrinsic ssRNA-binding activity, SauCas9 may have utility as a platform for directing other effector proteins to specific RNA molecules, such as proteins or domains that up-regulate translation or RNA base-modifying enzymes for site-specific epigenetic modification of RNAs.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11661599B1). An electronic copy of the sequence listing will also be available from the USPTO upon request and payment of the fee set forth in 37 CFR 1.19(b)(3).

The invention claimed is:

1. A method of conducting a cleavage assay, the method comprising:
   incubating a synthetic guiding component with a nuclease and a single-stranded target sequence, the synthetic guiding component including a targeting portion configured to bind and/or cleave the single-stranded target sequence; and
   cleaving the single-stranded target sequence without a short DNA oligomer containing a proto-spacer adjacent motif (PAM) sequence (PAMmer);
   wherein the synthetic guiding component comprises a structure having the formula (I):

W—X—Y-L-Z or a salt thereof, wherein:

W is an optional third portion comprising a nucleic acid sequence of from about 1 to 20 nucleic acids;
   X is the targeting portion comprising a nucleic acid sequence configured to bind to a target site of the single-stranded target sequence;
   Y is a first portion comprising a nucleic acid sequence configured to interact with a nuclease configured to cleave the single-stranded target sequence;
   L is a linker; and
   Z is a second portion comprising a nucleic acid sequence configured to interact with the nuclease and the first portion;
   wherein the nuclease is a SauCas9 protein.

2. The method of claim 1, wherein:
   Y comprises a nucleic acid sequence having at least 80% sequence identity to any one of SEQ ID NOs:150-155 or a complement of any of these; and
   Z comprises a nucleic acid sequence having at least 80% sequence identity to any one of SEQ ID NOs:162-178 or a complement of any of these.

3. The method of claim 1, wherein:
   L comprises a bond or a nucleic acid sequence having at least 80% sequence identity to any one of SEQ ID NOs:156-161, 187-191, 226-231, and 265-269, or a complement of any of these.

4. The method of claim 1, wherein W and/or Y comprises one or more modified nucleic acids or bulges.

5. The method of claim 1, wherein the single stranded target sequence recited for X is a single-stranded human mRNA target sequence or a single-stranded pathogen target sequence.

6. The method of claim 5, X has a length of from about 15 to about 30 nucleotides.

7. The method of claim 1, wherein the single-stranded target sequence is a single-stranded ribonucleic acid sequence.

8. The method of claim 1, wherein the nuclease comprises an amino acid sequence having at least 80% sequence identity to any one of SEQ ID NOs:100, 101, and 110.

9. The method of claim 1, wherein:
   Y comprises a nucleic acid sequence having at least 80% sequence identity to any one of SEQ ID NOs:179-186, or a complement of any of these, or a fragment thereof;
   L is a bond or comprises a nucleic acid sequence having at least 80% sequence identity to any one of SEQ ID NOs:187-191, or a complement of any of these, or a fragment thereof; and
   Z comprises a nucleic acid sequence having at least 80% sequence identity to any one of SEQ ID NOs:192-212, or a complement of any of these, or a fragment thereof.

10. The method of claim 1, wherein W has a length of from 0 to about 20 nucleotides, X has a length of from about 10 to about 30 nucleotides, Y has a length of from about 10 to about 40 nucleotides, L has a length of from 0 to about 10 nucleotides, and Z has a length of from about 10 to about 90 nucleotides.

11. The method of claim 1, wherein the structure has a length of from about 100 to about 200 nucleotides.

12. The method of claim 1, further comprising detecting a label on the synthetic guiding component or a reporter on a nucleic acid substrate, wherein a detectable signal is provided upon recognition of the single-stranded target sequence by the synthetic guiding component.

13. The method of claim 12, wherein the nuclease comprises an amino acid sequence corresponding to SEQ ID NOs: 100 or 101.

14. The method of claim 13, wherein the nuclease comprises an amino acid sequence corresponding to SEQ ID NO: 101.

15. The method of claim 13, wherein the nuclease comprises an amino acid sequence corresponding to SEQ ID NO: 100.

16. The method of claim 1, wherein the single-stranded target sequence comprises an RNA sequence of a virus, the virus having a lifecycle consisting of solely RNA molecules.

17. A method of conducting a cleavage assay, the method comprising:
   incubating a synthetic guiding component with a nuclease and a single-stranded target sequence, the synthetic guiding component including a targeting portion configured to bind and/or cleave the single-stranded target sequence; and
   cleaving the single-stranded target sequence without a short DNA oligomer containing a proto-spacer adjacent motif (PAM) sequence (PAMmer);
   wherein the synthetic guiding component comprises a structure having the formula (I):

W—X—Y-L-Z or a salt thereof, wherein:
   W is an optional third portion comprising a nucleic acid sequence of from about 1 to 20 nucleic acids;
   X is the targeting portion comprising a nucleic acid sequence configured to bind to a target site of the single-stranded target sequence;
   Y comprises a nucleic acid sequence having at least 80% sequence identity to any one of SEQ ID NOs:150-155, or a complement of any of these;
   L is a bond or comprises a nucleic acid sequence having at least 80% sequence identity to any one of SEQ ID NOs:156-161, or a complement of any of these;
   Z comprises a nucleic acid sequence having at least 80% sequence identity to any one of SEQ ID NOs:162-178, or a complement of any of these; and
   the nuclease comprises an amino acid sequence having at least 80% sequence identity to any one of SEQ ID NOs:100, 101, and 110.

18. A method of conducting a cleavage assay, the method comprising:
   incubating a synthetic guiding component with a nuclease and a single-stranded target sequence, the synthetic guiding component including a targeting portion configured to bind and/or cleave the single-stranded target sequence; and
   cleaving the single-stranded target sequence without a short DNA oligomer containing a proto-spacer adjacent motif (PAM) sequence (PAMmer);

wherein the synthetic guiding component comprises a structure having the formula (I):

W—X—Y-L-Z or a salt thereof, wherein:

W is an optional third portion comprising a nucleic acid sequence of from about 1 to 20 nucleic acids;

X is the targeting portion comprising a nucleic acid sequence configured to bind to a target site of the single-stranded target sequence;

Y is a first portion comprising a nucleic acid sequence configured to interact with a nuclease configured to cleave the single-stranded target sequence;

L is a linker; and

Z is a second portion comprising a nucleic acid sequence configured to interact with the nuclease and the first portion;

wherein the nuclease is a SauCas9 or CjeCas9 protein and the single-stranded target sequence is a single-stranded ribonucleic acid sequence.

19. The method of claim 18, wherein the nuclease is a CjeCas9 protein.

20. The method of claim 18, wherein the nuclease is a SauCas9 protein.

21. The method of claim 18, wherein:

Y comprises a nucleic acid sequence having at least 80% sequence identity to any one of SEQ ID NOs:150-155, 179-186, or a complement of any of these; and Z comprises a nucleic acid sequence having at least 80% sequence identity to any one of SEQ ID NOs:162-178, 192-212 or a complement of any of these.

22. The method of claim 18, wherein:

L comprises a bond or a nucleic acid sequence having at least 80% sequence identity to any one of SEQ ID NOs:156-161, 187-191, 226-231, and 265-269, or a complement of any of these.

23. The method of claim 18, wherein W and/or Y comprises one or more modified nucleic acids or bulges.

24. The method of claim 18, wherein the single stranded target sequence recited for X is a single-stranded human mRNA target sequence or a single-stranded pathogen target sequence.

25. The method of claim 18, X has a length of from about 15 to about 30 nucleotides.

26. The method of claim 18 wherein the nuclease comprises an amino acid sequence having at least 80% sequence identity to any one of SEQ ID NOs:100, 101, 104, 110, and 111.

27. The method of claim 26, wherein the nuclease comprises an amino acid sequence having at least 80% sequence identity to any one of SEQ ID NOs: 104, and 111.

28. The method of claim 18, wherein W has a length of from 0 to about 20 nucleotides, X has a length of from about 10 to about 30 nucleotides, Y has a length of from about 10 to about 40 nucleotides, L has a length of from 0 to about 10 nucleotides, and Z has a length of from about 10 to about 90 nucleotides.

29. The method of claim 18, wherein the synthetic guiding component has a length of from about 100 to about 200 nucleotides.

30. The method of claim 18, further comprising detecting a label on the synthetic guiding component or a reporter on a nucleic acid substrate, wherein a detectable signal is provided upon recognition of the single-stranded target sequence by the synthetic guiding component.

31. The method of claim 18, wherein the single-stranded ribonucleic acid sequence is the RNA sequence of a virus, the virus having a lifecycle consisting of solely RNA molecules.

32. The method of claim 18, wherein the nuclease comprises an amino acid sequence having at least 98% sequence identity to any one of SEQ ID NOs: 100, 101, 104, 110, and 111.

33. The method of claim 18, wherein Y comprises a nucleic acid sequence having at least 90% sequence identity to any one of SEQ ID NOs:150-155, 179-186, or a complement of any of these; and Z comprises a nucleic acid sequence having at least 90% sequence identity to any one of SEQ ID NOs:162-178, 192-212 or a complement of any of these.

* * * * *